United States Patent
Li et al.

(10) Patent No.: US 11,078,227 B2
(45) Date of Patent: Aug. 3, 2021

(54) 5'-CYCLO-PHOSPHONATE MODIFIED NUCLEOTIDES

(71) Applicant: Arrowhead Pharmaceuticals, Inc., Pasadena, CA (US)

(72) Inventors: Zhen Li, Monona, WI (US); Tao Pei, Middleton, WI (US); Michael Lawler, Waunakee, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 18 days.

(21) Appl. No.: 16/207,870

(22) Filed: Dec. 3, 2018

(65) Prior Publication Data

US 2019/0085012 A1 Mar. 21, 2019

Related U.S. Application Data

(63) Continuation of application No. PCT/US2017/036108, filed on Jun. 6, 2017.

(60) Provisional application No. 62/346,304, filed on Jun. 6, 2016.

(51) Int. Cl.
| | |
|---|---|
| *C07H 19/10* | (2006.01) |
| *C07H 21/02* | (2006.01) |
| *C07H 19/16* | (2006.01) |
| *C07H 19/06* | (2006.01) |
| *C07H 19/207* | (2006.01) |
| *C12N 15/113* | (2010.01) |

(52) U.S. Cl.
CPC ............ *C07H 19/10* (2013.01); *C07H 19/06* (2013.01); *C07H 19/16* (2013.01); *C07H 19/207* (2013.01); *C07H 21/02* (2013.01); *C12N 15/113* (2013.01); *C12N 2310/14* (2013.01); *C12N 2310/31* (2013.01); *C12N 2310/312* (2013.01); *C12N 2310/323* (2013.01); *C12N 2310/3231* (2013.01); *C12N 2310/3233* (2013.01); *C12N 2310/3519* (2013.01)

(58) Field of Classification Search
CPC ........ C07H 19/06; C07H 19/16; C07H 19/10; C07H 19/207; C07H 21/02; C12N 15/113; C12N 2310/3233; C12N 2310/3231; C12N 2310/323; C12N 2310/31; C12N 2310/14; C12N 2310/312; C12N 2310/3519
See application file for complete search history.

(56) References Cited

U.S. PATENT DOCUMENTS

| | | | |
|---|---|---|---|
| 5,567,811 A | 10/1996 | Misiura et al. | |
| 5,864,032 A * | 1/1999 | Misiura ................. | C07F 9/2408 435/6.12 |
| 8,314,227 B2 | 11/2012 | Wengel | |
| 8,993,738 B2 | 3/2015 | Prakash et al. | |
| 9,051,570 B2 * | 6/2015 | Wengel ................ | C12N 15/113 |
| 9,127,033 B2 * | 9/2015 | Prakash ............... | C07H 19/067 |
| 9,293,009 B2 * | 3/2016 | Asher ................. | G07F 17/3288 |
| 9,303,260 B2 * | 4/2016 | Wengel ................. | C07H 21/00 |
| 9,321,799 B2 | 4/2016 | Prakash et al. | |
| 9,944,929 B2 * | 4/2018 | Wengel ................ | C12N 15/113 |
| 10,450,565 B2 * | 10/2019 | Li ............................ | A61P 1/16 |
| 10,457,945 B2 * | 10/2019 | Wengel ................ | C12N 15/111 |
| 2011/0196141 A1 | 8/2011 | Vaijayanti et al. | |
| 2013/0116420 A1 | 5/2013 | Prakash et al. | |
| 2016/0068837 A1 | 3/2016 | Wonsuk et al. | |

FOREIGN PATENT DOCUMENTS

| | | |
|---|---|---|
| WO | 1994017093 A1 | 8/1994 |
| WO | 1994022890 A1 | 10/1994 |
| WO | 1999014226 A2 | 3/1999 |
| WO | 2000053722 A2 | 9/2000 |
| WO | 2007134181 A2 | 11/2007 |
| WO | 2008022309 A2 | 2/2008 |
| WO | 2008101157 A1 | 8/2008 |

(Continued)

OTHER PUBLICATIONS

Abbas, S. et al.; "Commercially Available 5'-DMT Phosphoramidites as Reagents for the Synthesis of Vinylphosphonate-Linked Oligonucleic Acids"; Organic Letters; vol. 3, No. 21; 3365-3367; 2001.

(Continued)

*Primary Examiner* — Lawrence E Crane

(74) *Attorney, Agent, or Firm* — Robert M. Teigen; Paul VanderVelde

(57) ABSTRACT

Described are 5'-cyclo-phosphonate modified nucleotides, and oligonucleotides, such as interference (RNAi) agents, containing 5'-cyclo-phosphonate modified nucleotides. The RNAi agents having either double-stranded or single-stranded oligonucleotides described herein comprising 5'cyclo-phosphonate modified nucleotides are useful in modulating gene expression as well as therapeutic, diagnostic, target validation, and genomic discovery applications. The RNAi agents and single-stranded antisense oligonucleotides comprising 5'-cyclo-phosphonate modified nucleotides are useful in the treatment of diseases or conditions that respond to inhibition of gene expression or activity in a cell, tissue, or organism.

(Formula A)

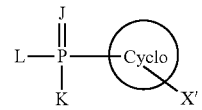

19 Claims, 2 Drawing Sheets

Specification includes a Sequence Listing.

(56) References Cited

FOREIGN PATENT DOCUMENTS

| WO | 2008154401 | A2 | 12/2008 |
|---|---|---|---|
| WO | 2011005860 | A2 | 1/2011 |
| WO | 2011104169 | A1 | 9/2011 |
| WO | 2011133871 | A2 | 10/2011 |
| WO | 2011139702 | A2 | 11/2011 |
| WO | 2012083185 | A2 | 6/2012 |
| WO | 2013032829 | A1 | 3/2013 |
| WO | 2013158141 | A1 | 10/2013 |
| WO | 2014130607 | A1 | 8/2014 |
| WO | 2016028649 | A1 | 2/2016 |

OTHER PUBLICATIONS

Baenziger et al.; "Galactose and N-Acetylgalactosamine-Specific Endocytosis of Glycopeptides by Isolated Rat Hepatocytes"; Cell; vol. 22; 611-620; 1980.

Bohringer e al.; "Synthesis of 5'-deoxy-5'-methylphosphonate Linked Thymidine Oligonucleotides"; Tetrahedron Lett.; 1993; 12(17):2723-2726.

Chen et al.; "Strand-specific 5'-O-methylation of siRNA duplexes controls guide strand selection and targeting specificity"; RNA; 2008; 14:263-274.

Connolly et al.; "Binding and Endocytosis of Cluster Glycosides by Rabbit Hepatocytes"; J. Biol. Chem; 257(2):939-45; (1982).

Elbashir et al.; Duplexes of 21-nucleotide RNAs mediate RNA interference in cultured mammalian cells; Nature; 2001; 411: 494-498.

Elbashir et al.; "RNA interference is mediated by 21- and 22-nucleotide RNAs"; Genes & Devel.; 2001; 15:188-200.

Eppacher et al.; "Synthesis and Incorporation of C (5')-Ethynylated Uracil-Derived Phosphoramidites into RNA"; Helvetica Chimica Acta; 2004; 87(12):3004-3020.

Frazer, K. et al.; "The apolipoprotein(a) gene is regulated by sex hormones and acute-phase inducers in YAC transgenic mice"; Nature Genetics; vol. 9; 424-431; 1995.

Guidotti LG et al.; "High-Level Hepatitis B Virus Replication in Transgenic Mice"; Journal of Virology; vol. 69, No. 10; p. 6158-6169; 1995.

Iobst ST et al.; "Selective Sugar Binding to the Carbohydrate Recognition Domains of the Rat Hepatic and Macrophage Asialoglycoprotein Receptors." Journal of Biological Chemistry (1996) 271(12), p. 6686-6693.

Matulic-Ademic et aL; "Synthesis and incorporation of 5'amino-and 5'-mercapto-5'-deoxy-2'-O-methyl nucleosides into hammerhead ribozymes"; Nucleosides & Nucleotides; 1997; 16:1922-1950.

Mikhailov et al.; "Substrate Properties of C'-Methylnucleoside and C'-Methyl-2'-Deoxynucleoside 5' Triphosphates in RNA and DNA Synthesis Reactions Catalysed by RNA and DNA Polymerases"; Nucleosides & Nucleotides; 1991; 10(1-3):339-343.

Saha et al.; "5'-Me-DNA—A New Oligonucleotide Analog: Synthesis and Biochemical Properties"; J. Org. Chem.; 1995; 60:788-789.

Wang et al.; "Biophysical and Biochemical Properties of Oligodeoxynucleotides Containing 4'C- and 5'C-Substituted Thymidines"; Bioorg. Med. Chem. Lett.; 1999; 9:885-890.

Whittaker, B. et al.; "Stereoselective synthesis of highly functionalized P-stereogenic nucleosides via palladium-catalysed P—C cross-coupling reactions"; Tetrahedron Letters 49; 6984-6987; 2008.

Wu et al.; "Functionalization of the Sugar Moiety of Oligoribonucleotides on Solid Support"; Bioconjugate Chem.; 1999; 10:921-924.

Wu et al; "Synthesis of 5'C- and 2'O-(Bromoalkyl)-Substituted Ribonucleoside Phosphoramidites for the Post-synthetic Functionalization of Oligonucleotides on Solid Support"; Helvetica Chimica Acta; 2000; 83:1127-1143.

Yang PL et al.; "Hydrodynamic injection of viral DNA: A mouse model of acute hepatitis B virus infection"; PNAS USA; vol. 99: p. 13825-13830; 2002.

Zhang G et al.; "High Levels of Foreign Gene Expression in Hepatocytes after Tail Vein Injections of Naked Plasmid DNA"; Human Gene Therapy; vol. 10; 1735-1737; 1999.

Zhao Z et al.; "Synthesis and Preliminary Biochemical Studies with 5'-Deoxy-5'-methylidyne Phosphonate Linked Thymidine Oligonucleotides"; Tetrahedron Letters; vol. 37, No. 35; 6239-6242; 1996.

International Search Report and Written Opinion for corresponding Application PCT/US17/36108 dated Aug. 3, 2017.

* cited by examiner

SEQUENCE LISTING

<160> NUMBER OF SEQ ID NOS: 12

<210> SEQ ID NO 1
<211> LENGTH: 21
<212> TYPE: RNA
<213> ORGANISM: artificial sequence
<220> FEATURE:
<223> OTHER INFORMATION: RNAi agent sense strand

<400> SEQUENCE: 1
gccccuuauu guuauacgau u                                              21

<210> SEQ ID NO 2
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 2
ucguauaaca auaaggggcu u                                              21

<210> SEQ ID NO 3
<211> LENGTH: 21
<212> TYPE: RNA
<213> ORGANISM: artificial sequence
<220> FEATURE:
<223> OTHER INFORMATION: RNAi agent sense strand

<400> SEQUENCE: 3
gccccuuauu guuauacgau u                                              21

<210> SEQ ID NO 4
<211> LENGTH: 21
<212> TYPE: DNA
<213> ORGANISM: artificial sequence
<220> FEATURE:
<223> OTHER INFORMATION: RNAi agent antisense strand with 5'-cyclopropyl
      phosphonate modified nucleotide
<220> FEATURE:
<221> NAME/KEY: modified_base
<222> LOCATION: 1
<223> OTHER INFORMATION: /mod_base = "2'-MOE-5'-cyclopropyl phosphonate
      nucleoside"

<400> SEQUENCE: 4
tcguauaaca auaaggggcu u                                              21

<210> SEQ ID NO 5
<211> LENGTH: 21
<212> TYPE: RNA
<213> ORGANISM: artificial sequence
<220> FEATURE:
<223> OTHER INFORMATION: RNAi agent sense strand

<400> SEQUENCE: 5
acucaauaaa gugcuuugaa a                                              21

<210> SEQ ID NO 6
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 6
uuucaaagca cuuuauugag u                                              21

<210> SEQ ID NO 7
<211> LENGTH: 21
<212> TYPE: RNA
<213> ORGANISM: artificial sequence
<220> FEATURE:
<223> OTHER INFORMATION: RNAi agent sense strand

<400> SEQUENCE: 7
acucaauaaa gugcuuugaa a                                              21

<210> SEQ ID NO 8
<211> LENGTH: 21
<212> TYPE: RNA
<213> ORGANISM: artificial sequence
<220> FEATURE:
<223> OTHER INFORMATION: RNAi agent antisense strand with 5'-cyclopropyl
      phosphonate modified nucleotide
<220> FEATURE:
<221> NAME/KEY: modified_base
<222> LOCATION: 1
<223> OTHER INFORMATION: /mod_base = "2'-O-methyl-5'-cyclopropyl
      phosphonate nucleoside"

<400> SEQUENCE: 8
uuucaaagca cuuuauugag u                                              21

<210> SEQ ID NO 9
<211> LENGTH: 21
<212> TYPE: RNA
<213> ORGANISM: artificial sequence
<220> FEATURE:
<223> OTHER INFORMATION: RNAi agent sense strand

<400> SEQUENCE: 9
aacucaauaa agugcuuuga a                                              21

<210> SEQ ID NO 10
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 10
uucaaagcac uuuauugagu u                                              21

<210> SEQ ID NO 11
<211> LENGTH: 21
<212> TYPE: RNA
<213> ORGANISM: artificial sequence
<220> FEATURE:
<223> OTHER INFORMATION: RNAi agent sense strand

<400> SEQUENCE: 11
aacucaauaa agugcuuuga a                                              21

<210> SEQ ID NO 12
<211> LENGTH: 21
<212> TYPE: RNA
<213> ORGANISM: artificial sequence
<220> FEATURE:
<223> OTHER INFORMATION: RNAi agent antisense strand with 5'-cyclopropyl
      phosphonate modified nucleotide
<220> FEATURE:
<221> NAME/KEY: modified_base
<222> LOCATION: 1
<223> OTHER INFORMATION: /mod_base = "2'-deoxy-5'-cyclopropyl -continued

```
phosphonate nucleoside"

<400> SEQUENCE: 12
uucaaagcac uuuauugagu u                                    21
```

5'-CYCLO-PHOSPHONATE MODIFIED NUCLEOTIDES

CROSS REFERENCE TO RELATED APPLICATIONS

This application is a continuation of International Patent Application Serial No. PCT/US17/36108, filed Jun. 6, 2017, which claims priority to U.S. Provisional Patent Application Ser. No. 62/346,304, filed on Jun. 6, 2016, the contents of each which are incorporated herein by reference in their entirety.

FIELD OF THE INVENTION

Disclosed herein are 5'-cyclo-phosphonate modified nucleotides useful for incorporating into oligomeric compounds, such as RNAi agents.

BACKGROUND

Oligomeric compounds that include nucleotide sequences at least partially complementary to a target nucleic acid have been shown to alter the function and activity of the target both in vitro and in vivo. When delivered to a cell containing a target nucleic acid (such as messenger RNA (mRNA)), oligomeric compounds have been shown to modulate the expression of the target resulting in altered transcription or translation of the target nucleic acid. In certain instances, the oligomeric compounds can reduce the expression of the gene by inhibiting the nucleic acid target and/or triggering the degradation of the target nucleic acid.

If the target nucleic acid is mRNA, one mechanism by which an expression-inhibiting oligomeric compound can modulate the expression of the mRNA target is through RNA interference (RNAi). RNAi is a biological process by which RNA or RNA-like molecules (such as chemically modified RNA molecules) are able to silence gene expression through degradation. The process of post-transcriptional gene silencing is thought to be an evolutionary-conserved cellular defense mechanism used to prevent the expression of foreign genes.

The RNAi response mechanism is believed to feature an endonuclease complex, commonly referred to as an RNA-induced silencing complex (RISC), which incorporates in its structure a single strand of an RNA or RNA-like molecule that is complementary to its target. The RISC is understood to mediate cleavage of single-stranded RNA (i.e., mRNA) by virtue of the complementarity of the single stranded RNA or RNA-like molecule that is incorporated into RISC with the mRNA.

Synthetic RNA and RNA-like molecules have been shown to elicit RNA interference in vitro and in vivo. For example, Elbashir et al. (*Nature* 2000, 411, 494-98) describes RNAi induced by introduction of duplexes of synthetic 21-nucleotide RNA molecules in cultured mammalian cells. The types of synthetic RNA or RNA-like molecules that can interact with RISC and trigger the RNAi response mechanism may be comprised of modified nucleotides and/or one or more non-phosphodiester linkages.

Additionally, single-stranded RNA and RNA-like molecules, which can also include modified nucleotides and have one or more non-phosphodiester linkages, can also alter the expression of a targeted mRNA.

Certain known modified nucleotides when incorporated into oligomeric compounds have been shown to enhance the duration and/or activity of expression-inhibiting oligomeric compounds when administered in vivo.

SUMMARY

There is a need for novel modified nucleotides that can provide improved or enhanced stability and/or potency to oligomeric compounds, such as RNAi agents. For example, there is a need for novel modified nucleotides that can provide enhanced stabilization of the phosphate moiety on the terminal nucleotide on the 5' terminal end of an RNAi agent.

Described herein are novel 5'-cyclo-phosphonate modified nucleotides, and oligomeric compounds, such as RNAi agents, that include 5'-cyclo-phosphonate modified nucleotides. The described 5'-cyclo-phosphonate modified nucleotides may be incorporated into double-stranded oligonucleotides (such as a short interfering RNA) or single-stranded oligonucleotides (such as antisense oligonucleotides). The oligomeric compounds, such as RNAi agents, that include one or more 5'-cyclo-phosphonate modified nucleotides, may also have targeting ligands, such as n-acetyl-galactosamine clusters or peptides, linked to the RNAi agents. The oligomeric compounds, such as RNAi agents, that include one or more 5'-cyclo-phosphonate modified nucleotides, may also have pharmacokinetic modulators, such as polyethylene glycol (PEG) moieties or lipids, linked to the RNAi agents.

The 5'-cyclo-phosphonate nucleotides described herein can provide improved stability and/or potency of RNAi agents. In some embodiments, the 5'-cyclo-phosphonate nucleotides disclosed herein provide for increased stability and resistance to endonucleases and exonucleases that in vivo may cleave the phosphodiester bond of an oligonucleotide chain. Additionally, while not wishing to be bound by theory, it is believed that the 5'-phosphorylation status of the terminal end of an RNAi agent is a factor for strand incorporation into RISC. Thus, a 5'-cyclo-phosphonate modified nucleotide positioned at the 5' terminal end of the antisense strand can increase the likelihood that the 5' terminal end of an oligonucleotide is and remains phosphorylated. This can increase the likelihood of loading that particular strand into RISC, and thereby allowing the RNAi agent to enter the RNAi pathway, resulting in improved and enhanced knockdown and gene silencing activity.

The 5'-cyclo-phosphonate modified nucleotides disclosed herein have a cyclic group or cyclic moiety located at the 5' carbon of the sugar (or at a comparable position of a sugar surrogate replacement moiety) of the nucleotide. The 5'-cyclo-phosphonate modified nucleotides disclosed herein form a phosphonate group (or, as described herein, a phosphonate mimic group by incorporating, for example, a 5'-C-malonyl group) at the 5' end of the oligonucleotide.

In some embodiments, the disclosed 5'-cyclo-phosphonate modified nucleotide compounds have the structure represented by Formula A:

(Formula A)

wherein:

Cyclo is an optionally substituted divalent cyclic moiety having 2, 3, 4, 5, 6, 7, 8, 9, or 10 carbon atoms, such as cycloalkyl (e.g., cyclopropyl, cyclobutyl, cyclopentyl, cyclohexyl, or cycloheptyl), cycloalkenyl (e.g., cyclopentenyl, cyclobutenyl, cyclopentenyl, cyclohexenyl, or cycloheptenyl), aryl (e.g., phenyl), heteroaryl (e.g., pyridyl, pyrimidinyl, pyridazinyl, pyrrole, pyrazole, imidazole, thiophene, benzothiophene, thiazole, benzothiazole, furan, oxazole, isoxazole, benzofuran, indole, indazole, benzimidazole, oxadiazole, 1,2,3-triazole, 1,2,4-triazole, tetrazole, quinolinyl, isoquinolinyl, or quinoxalinyl), or heterocyclyl (e.g., tetrahydrofuran, tetrahydropyran, piperidine, pyrrolidine, dioxane, or dioxolane);

X' is

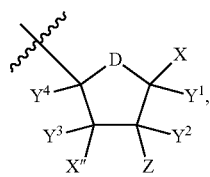
(s-i)

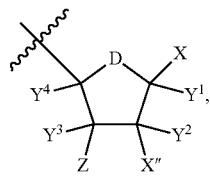
(s-ii)

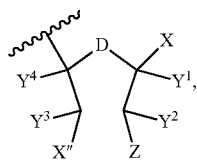
(s-iii)

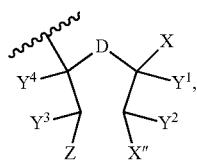
(s-iv)

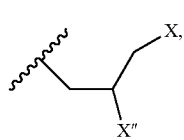
(s-v)

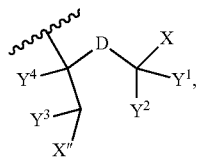
(s-vi)

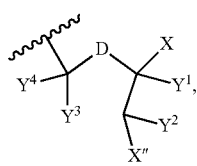
(s-vii)

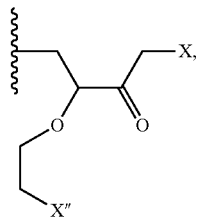
(s-viii)

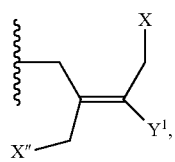
(s-ix)

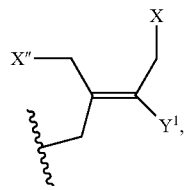
(s-x)

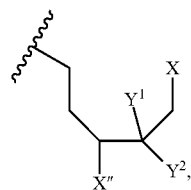
(s-xi)

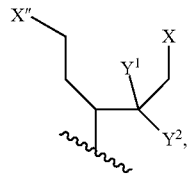
(s-xii)

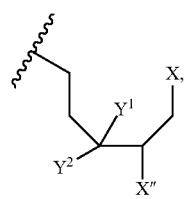
(s-xiii)

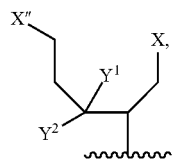
(s-xiv)

or includes a sugar surrogate replacement moiety;

X" is (i) an internucleoside linkage that links the 5'-cyclophosphonate modified nucleotide to the remainder of the RNAi agent, or (ii) a phosphoramidite group;

D is O, S, $CH_2$—$CH_2$, CH=CH, $OCH_2$, $N(R^2)$, $C(R^2)(R^3)$, $C(R^2)(R^3)C(R^4)(R^2)$, $C(R^2)$=$C(R^4)$, $OC(R^2)(R^3)$, $OC(H)(X^3)$ or $OC(R^2)(X^3)$;

$R^1$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

$R^2$, $R^3$, and $R^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

when D is O, S, $CH_2$—$CH_2$, CH=CH, $OCH_2$, $N(R^1)$, $C(R^2)(R^3)$, $C(R^2)(R^3)C(R^4)(R^2)$, $C(R^2)$=$C(R^4)$, $OC(R^2)(R^3)$, then X is a heterocyclic base moiety; when D is $OC(H)(X^3)$ or $OC(R^2)(X^3)$, X is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl and $X^3$ is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C(=O)$—$N(H)CH_3$, —$OCH_2C(=O)$—N(H)—$(CH_2)_2$—$N(CH_3)_2$, —$O(CH_2)_2$—N(H)—C(=NH)($NH_2$), —$O(CH_2)_3$—$N(R^5)(R^6)$, —$O(CH_2)_2$—$ON(R^5)(R^6)$, —$O(CH_2)_2$—O$(CH_2)_2$—$N(R^5)(R^6)$, —$OCH_2C(=O)$—$N(R^5)(R^6)$, —$OCH_2C(=O)$—$N(R^7)$—$(CH_2)_2$—$N(R^5)(R^6)$, —$O(CH_2)_2$—$N(R^7)$—C(=$R^8$)[$N(R^5)(R^6)$], optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

$Y^1$, $Y^2$, $Y^3$, and $Y^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl; or, alternatively, $Y^4$ is linked to one of $Y^1$ or $Y^2$, wherein the linkage comprises a divalent group selected from O, S, $NR^9$, $C(R^{10})(R^{11})$, $C(R^{10})$=$C(R^{11})$, C[=$C(R^{10})(R^{11})$] and C(=O), and the other two of $Y^1$, $Y^2$, and $Y^3$, are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein each $R^9$, $R^{10}$ and $R^{11}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

J is O, S, $NR^{12}$, N—$N(R^{13})_2$, or N—$OR^{13}$, wherein:

$R^{12}$ is H, OH, halogen, $C_1$-$C_{10}$ alkyl, $C_2$-$C_6$ alkenyl, $C_2$-$C_6$ alkynyl, aryl, or

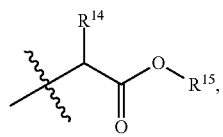

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)$NH_2$, wherein $R^{15}$ is selected from H, $C_1$-$C_{18}$ alkyl, or aryl;

wherein $R^{13}$ is H, $C_1$-$C_{10}$ alkyl, $C_2$-$C_6$ alkenyl, $C_2$-$C_6$ alkynyl, aryl, or

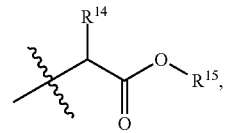

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)$NH_2$, and wherein $R^{15}$ is selected from H, $C_1$-$C_{18}$ alkyl, or aryl; and K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

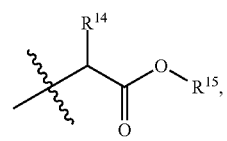

wherein $R^{14}$ is selected from H or $C_1$-$C_4$ alkyl optionally substituted with one to three substituents independently selected from SH, S—(C1-C4 alkyl), aryl optionally substituted with hydroxyl, heteroaryl optionally substituted with hydroxyl, amino, hydroxyl, oxo or —NH—C=(NH)$NH_2$, and $R^{15}$ is selected from H, $C_1$-$C_{18}$ alkyl, or aryl.

In some embodiments, Cyclo in the structure of Formula A is selected from the group consisting of:

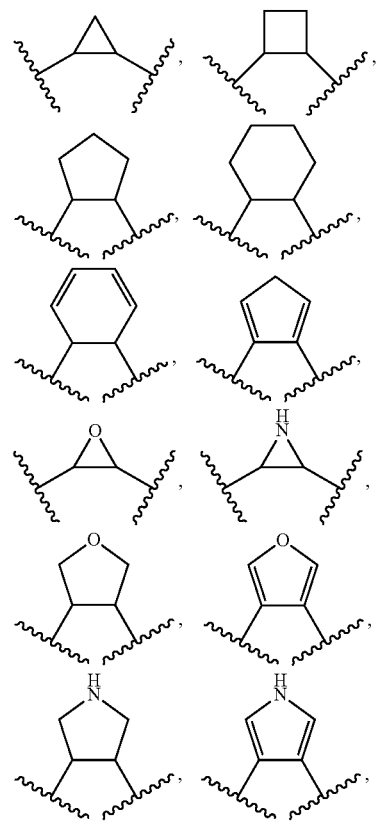

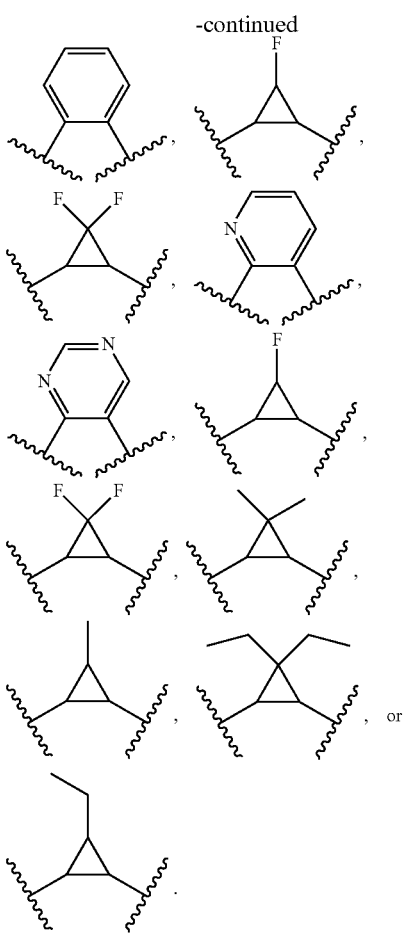

In some embodiments, Cyclo in the structure of Formula A is a cyclic functional group in which the cyclic functional group is linked to the phosphonate moiety and X' of Formula A at the following positions of the cyclic functional group, denoted using standard IUPAC nomenclature: 1,2; 1,3; 1,4; 1,5; 1,6; 1,7; 2,3; 2,4; 2,5; 2,6; 2,7; 3,4; 3,5; 3,6; 3,7; 4,5; 4,6; 4,7; 5,6; 5,7; or 6,7.

In some embodiments, Cyclo in the structure of Formula A is substituted. In some embodiments, Cyclo in the structure of Formula A is a substituted cyclic moiety linked to the phosphonate moiety and X' of Formula A at the following positions of the substituted cyclic functional group, denoted using standard IUPAC nomenclature: 1,2; 1,3; 1,4; 1,5; 1,6; 1,7; 2,3; 2,4; 2,5; 2,6; 2,7; 3,4; 3,5; 3,6; 3,7; 4,5; 4,6; 4,7; 5,6; 5,7; or 6,7.

In some embodiments, X' of Formula A is or includes a sugar surrogate replacement moiety. In some embodiments, X' of Formula A is or includes a sugar surrogate replacement moiety, wherein the sugar surrogate replacement moiety is a morpholino. In some embodiments, X' of Formula A is or includes a sugar surrogate replacement moiety wherein the sugar surrogate replacement moiety is a cyclohexenyl. In some embodiments, X' of Formula A is or includes a sugar surrogate replacement moiety wherein the sugar surrogate replacement moiety is a cyclohexitol.

In some embodiments, X' of Formula A is or includes a sugar surrogate replacement moiety, wherein the sugar surrogate replacement moiety is acyclic. In some embodiments, X' of Formula A is or includes an unlocked nucleobase analogue (UNA) as a sugar surrogate replacement moiety (see, e.g., U.S. Pat. No. 8,314,227). In some embodiments, X' of Formula A is or includes a glycerol nucleic acid structure as a sugar surrogate replacement moiety (see, e.g., WO 2016/028649).

In some embodiments, X' of Formula A is or includes a locked nucleic acid.

In some embodiments, the compounds disclosed herein have a 5'-cyclopropyl phosphonate group having Formula I-b or Formula II-b:

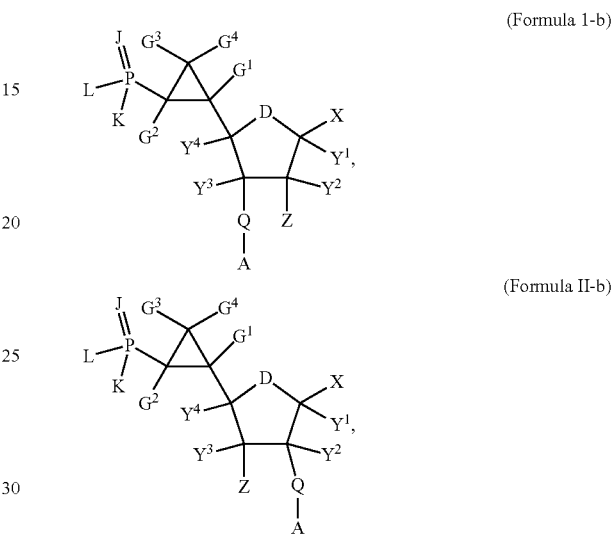

wherein,

D is O, S, $CH_2$—$CH_2$, CH=CH, $OCH_2$, $N(R^1)$, $C(R^2)(R^3)$, $C(R^2)(R^3)C(R^4)(R^2)$, $C(R^2)$=$C(R^4)$, $OC(R^2)(R^3)$, $OC(H)(X^3)$ or $OC(R^2)(X^3)$;

$R^1$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

$R^2$, $R^3$, and $R^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

when D is O, S, $CH_2$—$CH_2$, CH=CH, $OCH_2$, $N(R^2)$, $C(R^2)(R^3)$, $C(R^2)(R^3)C(R^4)(R^2)$, $C(R^2)$=$C(R^4)$, $OC(R^2)(R^3)$, then X is a heterocyclic base moiety;

when D is $OC(H)(X^3)$ or $OC(R^2)(X^3)$, X is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl and $X^3$ is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C$(=O)—N(H)$CH_3$, —$OCH_2C$(=O)—N(H)—$(CH_2)_2$—N$(CH_3)_2$, —$O(CH_2)_2$—N(H)—C(=NH)($NH_2$), —$O(CH_2)_3$—$N(R^5)(R^6)$, —$O(CH_2)_2$—$ON(R^5)(R^6)$, —$O(CH_2)_2$—$O$$(CH_2)_2$—$N(R^5)(R^6)$, —$OCH_2C$(=O)—$N(R^5)(R^6)$, —$OCH_2C$(=O)—$N(R^7)$—$(CH_2)_2$—$N(R^5)(R^6)$, —$O(CH_2)_2$—$N(R^7)$—C(=$R^8$)[$N(R^5)(R^6)$], optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

$Y^1$, $Y^2$, $Y^3$, and $Y^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl; or, alternatively, $Y^4$ is linked to one of $Y^1$ or $Y^2$, wherein the linkage comprises a divalent group selected from O, S, $NR^9$, $C(R^{10})(R^{11})$, $C(R^{10})$—$C(R^{11})$, $C[=C(R^{10})(R^{11})]$ and $C(=O)$, and the other two of $Y^1$, $Y^2$, and $Y^3$, are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein each $R^9$, $R^{10}$ and $R^{11}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

J is O, S, $NR^{12}$, N—$N(R^{13})_2$, or N—$OR^{13}$, wherein:

$R^{12}$ is H, OH, halogen, $C_1$-$C_{10}$ alkyl, $C_2$-$C_6$ alkenyl, $C_2$-$C_6$ alkynyl, aryl, or

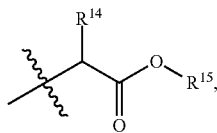

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)NH$_2$, wherein $R^{15}$ is selected from H, $C_1$-$C_{18}$ alkyl, or aryl;

wherein $R^{13}$ is H, $C_1$-$C_{10}$ alkyl, $C_2$-$C_6$ alkenyl, $C_2$-$C_6$ alkynyl, aryl, or

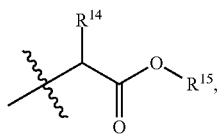

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)NH$_2$, and wherein $R^{15}$ is selected from H, $C_1$-$C_{18}$ alkyl, or aryl;

K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

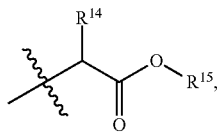

wherein $R^{14}$ is selected from H or $C_1$-$C_4$ alkyl optionally substituted with one to three substituents independently selected from SH, S—(C1-C4 alkyl), aryl optionally substituted with hydroxyl, heteroaryl optionally substituted with hydroxyl, amino, hydroxyl, oxo or —NH—C=(NH)NH$_2$, and $R^{15}$ is selected from H, $C_1$-$C_{18}$ alkyl, or aryl;

Q is a divalent moiety selected from O, S, $N(R^{30})$, or $C(R^{31})(R^{32})$, wherein $R^{30}$ is H, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, and $R^{31}$ and $R^{32}$ are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl; and A is (i) an internucleoside linkage that links the 5'-cyclophosphonate modified nucleotide of Formula I to the remainder of the RNAi agent, or (ii) a phosphoramidite group; and $G^1$, $G^2$, $G^3$ and $G^4$ are each independently selected from the group consisting of H, F, halogen, $C_1$-$C_6$ alkyl, CN, $CH_2(R^{33})$, $CH_2$—O—$(R^{33})$, $C(=O)(R^{33})$, $C(=S)(R^{33})$, or $(R^{34})(R^{33})$, wherein $R^{33}$ is $O(R^{35})$, $S(R^{35})$, $N(R^{35})(R^{36})$, wherein $R^{34}$, $R^{35}$, and $R^{36}$ are each independently selected from H, halogen, or $C_1$-$C_6$ alkyl.

In some embodiments, the compounds disclosed herein include a 5-cyclopropyl phosphonate group and are linked to an RNAi agent, having the following Formula III or Formula IV:

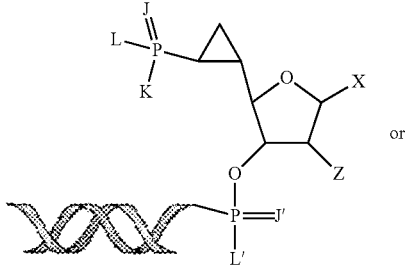

(Formula III)

or

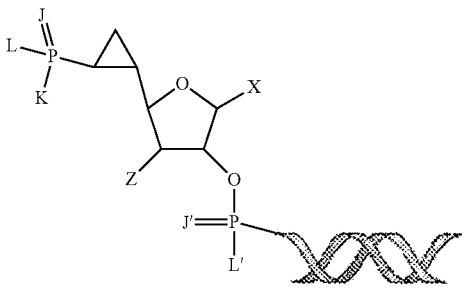

(Formula IV)

wherein:

X is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C(=O)$—$N(H)CH_3$, —$OCH_2C(=O)$—$N(H)$—$(CH_2)_2$—$N(CH_3)_2$, —$O(CH_2)_2$—$N(H)$—$C(=NH)(NH_2)$, —$O(CH_2)_3$—$N(R^5)(R^6)$, —$O(CH_2)_2$—$ON(R^5)(R^6)$, —$O(CH_2)_2$—$O(CH_2)_2$—$N(R^5)(R^6)$, —$OCH_2C(=O)$—$N(R^5)(R^6)$, —$OCH_2C(=O)$—$N(R^7)$—$(CH_2)_2$—$N(R^5)(R^6)$—$O(CH_2)_2$—$N(R^7)$—$C(=R^8)[N(R^5)(R^6)]$, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

J and J' are each independently, O or S;

L, L', and K are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

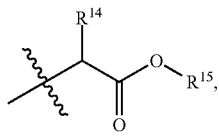

wherein $R^{14}$ is selected from H or $C_1$-$C_4$ alkyl optionally substituted with one to three substituents independently selected from SH, S—(C1-C4 alkyl), aryl optionally substituted with hydroxyl, heteroaryl optionally substituted with hydroxyl, amino, hydroxyl, oxo or —NH—C=(NH)NH$_2$, and $R^{15}$ is selected from H, $C_1$-$C_{18}$ alkyl, or aryl; and
⌇⌇⌇ includes the remainder of the RNAi agent.

In some embodiments, the disclosed 5-cyclo-phosphonate modified nucleotide compounds are phosphoramidite compounds.

In some embodiments, the disclosed 5-cyclo-phosphonate modified nucleotide compounds are phosphoramidite compounds having Formula I-b-5 or Formula II-b-5:

(Formula I-b-5)

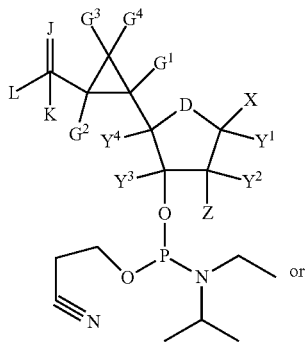

(Formula II-b-5)

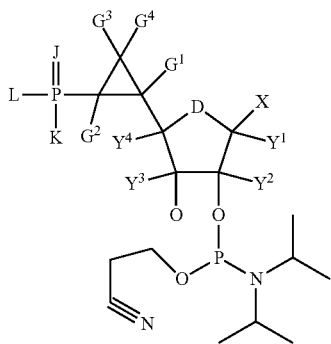

wherein,

D is O, S, $CH_2$—$CH_2$, CH=CH, $OCH_2$, $N(R^2)$, $C(R^2)(R^3)$, $C(R^2)(R^3)C(R^4)(R^2)$, $C(R^2)$=$C(R^4)$, $OC(R^2)(R^3)$, $OC(H)(X^3)$ or $OC(R^2)(X^3)$;

$R^1$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

$R^2$, $R^3$, and $R^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

when D is O, S, $CH_2$—$CH_2$, CH=CH, $OCH_2$, $N(R^1)$, $C(R^2)(R^3)$, $C(R^2)(R^3)C(R^4)(R^2)$, $C(R^2)$=$C(R^4)$, $OC(R^2)(R^3)$, then X is a heterocyclic base moiety;

when D is $OC(H)(X^3)$ or $OC(R^2)(X^3)$, X is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl and $X^3$ is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C(=O)$—$N(H)CH_3$, —$OCH_2C(=O)$—$N(H)$—$(CH_2)_2$—$N(CH_3)_2$, —$O(CH_2)_2$—$N(H)$—$C(=NH)(NH_2)$, —$O(CH_2)_3$—$N(R^5)(R^6)$, —$O(CH_2)_2$—$ON(R^5)(R^6)$, —$O(CH_2)_2$—$O(CH_2)_2$—$N(R^5)(R^6)$, —$OCH_2C(=O)$—$N(R^5)(R^6)$, —$OCH_2C(=O)$—$N(R^7)$—$(CH_2)_2$—$N(R^5)(R^6)$—$O(CH_2)_2$—$N(R^7)$—$C(=R^8)[N(R^5)(R^6)]$, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

$Y^1$, $Y^2$, $Y^3$, and $Y^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl; or, alternatively, $Y^4$ is linked to one of $Y^1$ or $Y^2$, wherein the linkage comprises a divalent group selected from O, S, $NR^9$, $C(R^{10})(R^{11})$, $C(R^{10})$=$C(R^{11})$, $C[=C(R^{10}(R^{11})]$ and $C(=O)$, and the other two of $Y^1$, $Y^2$, and $Y^3$, are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein each $R^9$, $R^{10}$ and $R^{11}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

J is O, S, $NR^{12}$, N—$N(R^{13})_2$, or N—$OR^{13}$, wherein:
$R^{12}$ is H, OH, halogen, $C_1$-$C_{10}$ alkyl, $C_2$-$C_6$ alkenyl, $C_2$-$C_6$ alkynyl, aryl, or

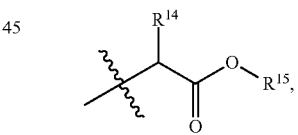

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)NH$_2$, wherein $R^{15}$ is selected from H, $C_1$-$C_{18}$ alkyl, or aryl;

wherein $R^{13}$ is H, $C_1$-$C_{10}$ alkyl, $C_2$-$C_6$ alkenyl, $C_2$-$C_6$ alkynyl, aryl, or

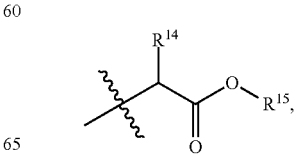

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)$NH_2$, and wherein $R^{15}$ is selected from H, $C_1$-$C_{18}$ alkyl, or aryl;

K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

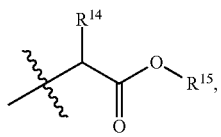

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo or —NH—C=(NH)$NH_2$, and $R^{15}$ is selected from H, $C_1$-$C_{18}$ alkyl, or aryl; and $G^1$, $G^2$, $G^3$ and $G^4$ are each independently selected from the group consisting of H, F, halogen, $C_1$-$C_6$ alkyl, CN, $CH_2(R^{33})$, $CH_2$—O—$(R^{33})$, C(=O)$(R^{33})$, C(=S)$(R^{33})$, or $(R^{34})(R^{33})$, wherein $R^{33}$ is $O(R^{35})$, $S(R^{35})$, $N(R^{35})(R^{36})$, wherein $R^{34}$, $R^{35}$, and $R^{36}$ are each independently selected from H, halogen, or $C_1$-$C_6$ alkyl.

In some embodiments, the phosphoramidite-containing compounds that include 5'-cyclopropyl phosphonate modified nucleotides have the following structures:

(Structure xi)

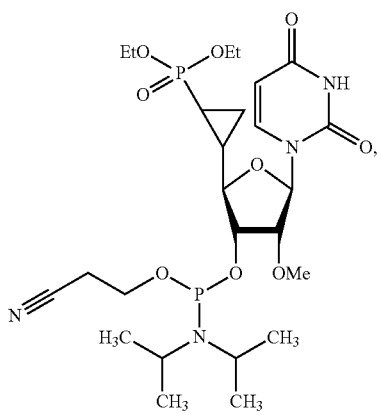

(Structure xii)

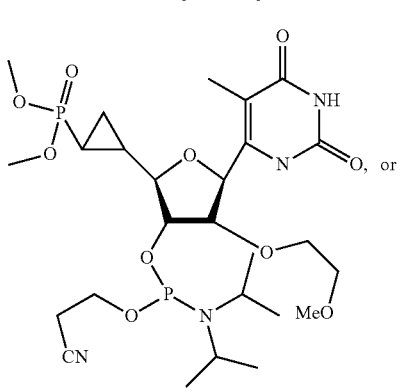

(Structure xiii)

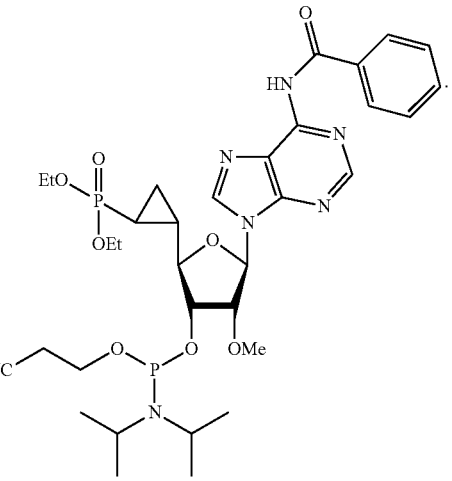

In some embodiments, the disclosed 5'-cyclo-phosphonate modified nucleotide compounds have the structure represented by Formula B:

(Formula B)

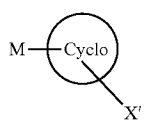

wherein:

Cyclo and X' are each as defined in connection with Formula A, above; and

M of Formula B is or includes a 5'-phosphonate mimic group. In some embodiments, M of Formula B is a 5'-C-malonyl group. In some embodiments, M of Formula B is a carboxic, sulfonic, or boronic acid. In some embodiments, M of Formula B is a di-carboxic, di-sulfonic, or di-boronic acid. In some embodiments, M of Formula B is a di-acid selected from a mixture of carboxic, sulfonic, boronic, and phosphoric acid. In some embodiments, the phosphonate mimic group (i.e., M of Formula B) is attached to Cyclo of Formula B through a single bond. In some embodiments, the phosphonate mimic group is attached to Cyclo of Formula B through more than one bond.

In some embodiments, the disclosed compounds of Formula B have the structure represented by the following structures:

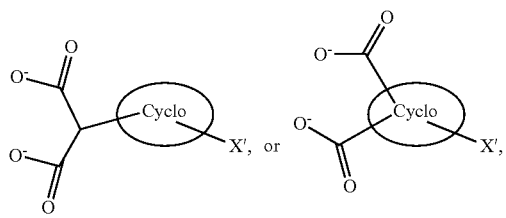

wherein, Cyclo and X' are each as defined in connection with Formula A, above.

In some embodiments, the disclosed compounds of Formula B have the structure represented by the following structures:

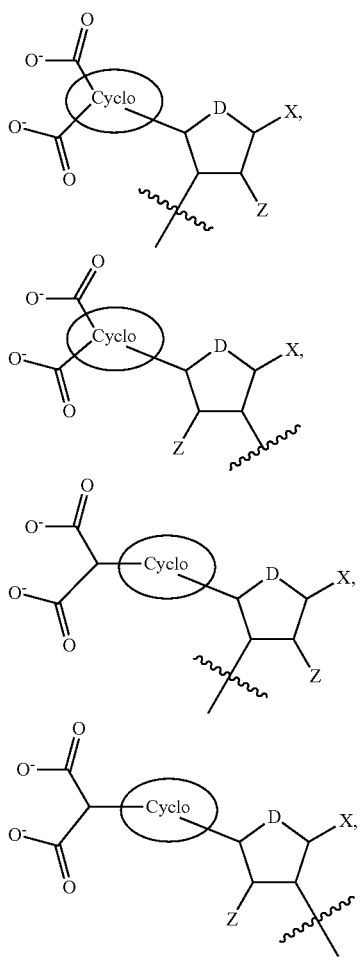

wherein, Cyclo, D, X, and Z are each as defined in connection with Formula A, above.

As used herein, the term "linked" when referring to the connection between two molecules means that the two molecules are joined by a covalent bond or that the two molecules are associated via intermolecular forces (e.g., hydrogen bonds, van der Waals forces, or ionic bonds). In some embodiments, where the term "linked" refers to the association between two molecules via intermolecular forces, the association between the two different molecules has a $K_D$ of less than $1\times10^{-4}$ M (e.g., less than $1\times10^{-5}$ M, less than $1\times10^{-6}$ M, or less than $1\times10^{-7}$ M) in a physiologically acceptable buffer (e.g., phosphate buffered saline).

As used herein, the term "directly linked" refers to a first compound or group being linked to a second compound or group without any intervening atoms or groups of atoms. As used herein, the term "indirectly linked" refers to a first compound being linked to a second compound or group through an intermediary atom, group, compound, or molecule, such as, for example, a linking group. Unless otherwise stated, the term "linked" as used herein includes both "directly linked" and "indirectly linked" as defined herein.

As used herein, an "oligomeric compound" is a nucleotide sequence containing about 10-50 nucleotides or nucleotide base pairs. In some embodiments, an oligomeric compound has a nucleobase sequence that is at least partially complementary to a coding sequence in an expressed target nucleic acid or target gene within a cell. In some embodiments, the oligomeric compounds, upon delivery to a cell expressing a gene, are able to inhibit the expression of the underlying gene, and are referred to herein as "expression-inhibiting oligomeric compounds." The gene expression can be inhibited in vitro or in vivo. "Oligomeric compounds" include, but are not limited to: oligonucleotides, single-stranded oligonucleotides, single-stranded antisense oligonucleotides, short interfering RNAs (siRNAs), double-strand RNAs (dsRNA), micro RNAs (miRNAs), short hairpin RNAs (shRNA), ribozymes, interfering RNA molecules, and dicer substrates.

As used herein, the terms "oligonucleotide" and "polynucleotide" mean a polymer of linked nucleosides each of which can be independently modified or unmodified.

As used herein, the term "single-stranded oligonucleotide" means a single-stranded oligomeric compound having a sequence at least partially complementary to a target mRNA, that is capable of hybridizing to a target mRNA through hydrogen bonding under mammalian physiological conditions (or similar conditions in vitro). In some embodiments, a single-stranded oligonucleotide is a single stranded antisense oligonucleotide. The 5'-cyclo-phosphonate modified nucleotides disclosed herein may be incorporated into single-stranded antisense oligonucleotides. In some embodiments, the 5'-cyclo-phosphonate modified nucleotides are positioned as the terminal nucleotide on the 5' end of the single-stranded oligonucleotide.

As used herein, an "RNAi agent" means an agent that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents include, but are not limited to: single-stranded oligonucleotides, single-stranded antisense oligonucleotides, short interfering RNAs (siRNAs), double-stranded RNAs (dsRNA), micro RNAs (miRNAs), short hairpin RNAs (shRNA), and dicer substrates. The RNAi agents described herein are comprised of an oligonucleotide having a strand that is at least partially complementary to the mRNA being targeted. In some embodiments, the RNAi agents described herein are double-stranded, and are comprised of an antisense strand and a sense strand that is at least partially complementary to the antisense strand. RNAi agents may be comprised of modified nucleotides and/or one or more non-phosphodiester linkages. In some embodiments, the RNAi agents described herein are single-stranded.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein or protein subunit translated from the mRNA in a cell, group of cells, tissue, organ, or subject in which the gene is transcribed, is reduced when the cell, group of cells, tissue, organ, or subject is treated with oligomeric compounds, such as RNAi agents, described herein as compared to a second cell, group of cells, tissue, organ, or subject that has not or have not been so treated.

As used herein, the term "sequence" or "nucleotide sequence" mean a succession or order of nucleobases or nucleotides, described with a succession of letters using the standard nucleotide nomenclature.

As used herein, a "nucleotide base," or "nucleobase" is a heterocyclic pyrimidine or purine compound, which is a standard constituent of all nucleic acids, and includes the bases that form the nucleotides adenine (A), guanine (G), cytosine (C), thymine (T), and uracil (U). A nucleobase may further be modified to include, without limitation, universal bases, hydrophobic bases, promiscuous bases, size-expanded bases, and fluorinated bases.

As used herein, the term "heterocyclic base moiety" is a nucleobase or a modified nucleobase as defined herein. In some embodiments, the heterocyclic base moiety is a pyrimidine, substituted pyrimidine, purine, or substituted purine. In some embodiments, the heterocyclic base moiety is a naturally occurring purine or substituted purine. In some embodiments, the heterocyclic base moiety is a non-naturally occurring purine or substituted purine. In some embodiments, the heterocyclic base moiety is a naturally occurring pyrimidine or substituted pyrimidine. In some embodiments, the heterocyclic base moiety is a non-naturally occurring pyrimidine or substituted pyrimidine. In some embodiments, particularly when the 5'-cyclo-phosphonate modified nucleotides disclosed herein are phosphoramidite compounds, the heterocyclic base moiety includes one or more protecting groups.

As used herein, a "sugar surrogate replacement moiety" refers to a structure capable of replacing the 5-membered furanose ring of a naturally occurring ribonucleotide.

As used herein, and unless otherwise indicated, the term "complementary," when used to describe a first nucleotide sequence (e.g., RNAi agent sense strand or targeted mRNA) in relation to a second nucleotide sequence (e.g., single-stranded antisense oligonucleotide or a double-stranded RNAi agent antisense strand), means the ability of an oligonucleotide or polynucleotide including the first nucleotide sequence to hybridize (form base pair hydrogen bonds under mammalian physiological conditions (or similar conditions in vitro)) and form a duplex or double helical structure under certain conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af are complementary to U (or T) and identical to A for the purposes of determining identity or complementarity.

As used herein, "perfectly complementary" or "fully complementary" means that all (100%) of the bases in a contiguous sequence of a first polynucleotide will hybridize with the same number of bases in a contiguous sequence of a second polynucleotide. The contiguous sequence may comprise all or a part of a first or second nucleotide sequence.

As used herein, "partially complementary" means that in a hybridized pair of nudeobase sequences, at least 70%, but not all, of the bases in a contiguous sequence of a first polynucleotide will hybridize with the same number of bases in a contiguous sequence of a second polynucleotide.

As used herein, "substantially complementary" means that in a hybridized pair of nucleobase sequences, at least 85%, but not all, of the bases in a contiguous sequence of a first polynucleotide will hybridize with the same number of bases in a contiguous sequence of a second polynucleotide. The terms "complementary," "fully complementary," and "substantially complementary" herein may be used with respect to the base matching between the sense strand and the antisense strand of a double-stranded RNAi agent, between the antisense strand of a double-stranded RNAi agent and a sequence of a target mRNA, or between a single-stranded anti sense oligonucleotide and a sequence of a target mRNA.

As used herein, the terms "treat," "treatment," and the like, mean the methods or steps taken to provide relief from or alleviation of the number, severity, and/or frequency of one or more symptoms of a disease or condition in a subject.

As used herein, the phrase "introducing into a cell," when referring to an RNAi agent comprising a 5'-cyclo-phosphonate modified nucleotide, means functionally delivering the RNAi agent into a cell. The phrase "functional delivery," means that delivering the RNAi agent to the cell in a manner that enables the RNAi agent to have the expected biological activity, e.g., sequence-specific inhibition of gene expression.

Unless stated otherwise, use of the symbol

as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers. The 5'-cyclo-phosphonate modified nucleotides described herein contain one or more asymmetric centers and thus give rise to enantiomers, diastereomers, and other stereoisomeric configurations that may be defined, in terms of absolute stereochemistry, as (R) or (S), as α or β (such as for sugar anomers), or as (D) or (L) (such as for amino acids). Included in the 5'-cyclo-phosphonate modified nucleotides described herein are all such possible isomers, including their racemic and optically pure forms. Unless specified otherwise, when the compounds described herein contain double bonds (in, e.g., alkenes or imines), it is intended that the compounds include both E and Z geometric isomers or cis- and trans-isomers. Likewise, all tautomeric forms are also intended to be included. The configuration of any bonds appearing herein are selected solely for convenience and are not intended to limit a particular configuration, unless the text so states otherwise.

The term "substituted," as used herein, means that any one or more hydrogens on the designated atom, usually a carbon, oxygen, or nitrogen atom, is replaced with any group as defined herein, provided that the designated atom's normal valency is not exceeded, and that the substitution results in a stable compound. When a substituent is keto or oxo (i.e., =O), then two (2) hydrogens on the atom are replaced. Ring double bonds, as used herein, are double bonds that are formed between two adjacent ring atoms (e.g., C=C, C=N, N=N, etc.). In some embodiments, a substituent group of a cyclic functional group is an additional cyclic or aryl group. As used herein, a bicyclic group is considered a substituted cyclic functional group. Examples of organic functional groups include, but are not limited to, hydrogen; halo (e.g., F, Cl, Br, I); cyano; —$CO_2R^a$; —$CONR^aR^a$; $C_{1-6}$ alkyl optionally substituted with from 1-2 independently selected $R^a$; $C_{1-4}$ haloalkyl; $C_{1-4}$ alkoxy; $C_{1-4}$ haloalkoxy; cycloalkyl, wherein the cycloalkyl is optionally substituted with from 1-4 independently selected $R^a$, heterocyclyl including from 5-8 ring atoms, wherein from 1-3 ring atoms are each independently selected from the group consisting of $N(R^a)$, O, and S, and wherein the heterocyclyl is optionally substituted with from 1-4 independently selected $R^a$; $C_{6-10}$ aryl optionally substituted with from 1-4 $R^a$; heteroaryl including from 5-10 ring atoms, wherein from 1-4 ring atoms are each independently selected from the group consisting of N, $N(R^a)$, O, and S, wherein the heteroaryl is optionally substituted with from 1-3 $R^a$; —$N_3$; —$CO_2H$; —OH; —$SO_{1-2}$($R^a$); —$NR^aR^a$; —$SO_{1-2}(NR^aR^a)$; and thioalkoxy; wherein each $R^a$ is independently selected from $C_{1-6}$ alkyl, —OH, -halo, —$NH_2$, —$N(C_{1-4}$ alkyl$)_2$, $C_{1-4}$ alkoxy, $C_{1-4}$ haloalkoxy, —C(=O)O($C_{1-4}$ alkyl), —C(=O)($C_{1-4}$ alkyl), —C(=O)OH, —CON($C_{1-4}$ alkyl$)_2$, —S(O)$_{1-2}$($C_{1-4}$ alkyl$)_2$, and cyano.

Some compounds of the present disclosure can exist in a tautomeric form that is also intended to be encompassed within the scope of the present disclosure. "Tautomers" are compounds whose structures differ markedly in the arrangement of atoms, but which exist in easy and rapid equilibrium. It is to be understood that compounds of the present disclosure may be depicted as different tautomers. It should also be understood that when compounds have tautomeric forms, all tautomeric forms are intended to be within the scope of the disclosure, and the naming of the compounds does not exclude any tautomeric form.

The compounds and pharmaceutically acceptable salts of the present disclosure can exist in one or more tautomeric forms, including ketone-enol, amide-nitrile, lactam-lactim, amide-imidic acid (e.g., in the nucleobases guanine, thymine, and cytosine), amine-enamine and enamine-enamine and geometric isomers and mixtures thereof. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the compounds disclosed herein. The concept of tautomers that are interconvertible by tautomerizations is called tautomerism. In tautomerism, a simultaneous shift of electrons and a hydrogen atom occurs.

Tautomerizations catalyzed by a base occur by means of: 1) deprotonation; 2) formation of a delocalized anion (e.g. an enolate); and 3) protonation at a different position of the anion. Tautomerizations catalyzed by an acid occur by means of 1) protonation; 2) formation of a delocalized cation; and 3) deprotonation at a different position adjacent to the cation.

As used herein, "protecting group," refers to a labile chemical moiety which is known in the art to prevent reactive groups (e.g., hydroxyl, amino, carboxyl, and sulfhydryl groups), from undergoing undesired reactions during synthetic procedures. Protecting groups are typically used selectively and/or orthogonally to protect sites during reactions at other reactive sites and can then be removed to leave the unprotected group as is or available for further reactions. In some embodiments, a "substituted" group or substituent group comprises a protecting group.

As used herein, the term "alkyl" refers to a saturated aliphatic hydrocarbon group, straight chain or branched, having from 1 to 10 carbon atoms unless otherwise specified. For example, "$C_1-C_6$ alkyl" includes alkyl groups having 1, 2, 3, 4, 5, or 6 carbons in a linear or branched arrangement. As used herein, the term "aminoalkyl" refers to an alkyl group as defined above, substituted at any position with one or more amino groups as permitted by normal valency. The amino groups may be unsubstituted, monosubstituted, or di-substituted.

As used herein, the term "cyclic functional group" is intended to mean a functional group that forms a ring structure. Cyclic functional groups include, but are not limited to, cycloalkyl, cycloalkenyl, cycloalkynyl, heterocyclyl, heteroaryl, and aryl.

As used herein, the term "cycloalkyl" means a saturated or unsaturated nonaromatic hydrocarbon ring group having from 3 to 14 carbon atoms, unless otherwise specified. Examples of cycloalkyl groups include, but are not limited to, cyclopropyl, methyl-cyclopropyl, 2,2-dimethyl-cyclobutyl, 2-ethyl-cyclopentyl, or cyclohexyl. Cycloalkyls may include multiple spiro- or fused rings. Cycloalkyl groups are optionally mono-, di-, tri-, tetra-, or penta-substituted on any position as permitted by normal valency.

As used herein, the term "alkenyl" refers to a non-aromatic hydrocarbon radical, straight or branched, containing at least one carbon-carbon double bond, and having from 2 to 10 carbon atoms unless otherwise specified. Up to five carbon-carbon double bonds may be present in such groups. For example, "$C_2-C_6$" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "$C_2-C_6$ alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may contain triple bonds as permitted by normal valency, and may be optionally mono-, di-, or tri-substituted on any position as permitted by normal valency.

As used herein, "alkoxyl" or "alkoxy" refers to an alkyl group as defined above with the indicated number of carbon atoms attached through an oxygen bridge. For example, $C_{1-6}$ alkoxy is intended to include $C_1$, $C_2$, $C_3$, $C_4$, $C_5$, and $C_6$ alkoxy groups. For example, $C_{1-8}$ alkoxy is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, hexanoyl), alkenoyl (e.g., acryloyl) alkynoyl (e.g., ethynoyl, propynoyl, butynoyl, pentynoyl, hexynoyl), aryloyl (e.g., benzoyl), heteroaryloyl (e.g., pyrroloyl, imidazoloyl, quinolinoyl, pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxycarbonyl.

As used herein, "aryl" means any stable monocyclic or polycyclic carbon ring of up to 7 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "heteroaryl" represents a stable monocyclic or polycyclic ring system of up to 7 atoms in each ring, wherein at least one ring is aromatic and contains from 1 to 4 heteroatoms selected from the group consisting of O, N and S. Examples of heteroaryl groups include, but are not limited to, acridinyl, carbazolyl, cinnolinyl, quinoxalinyl, pyrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, or di-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
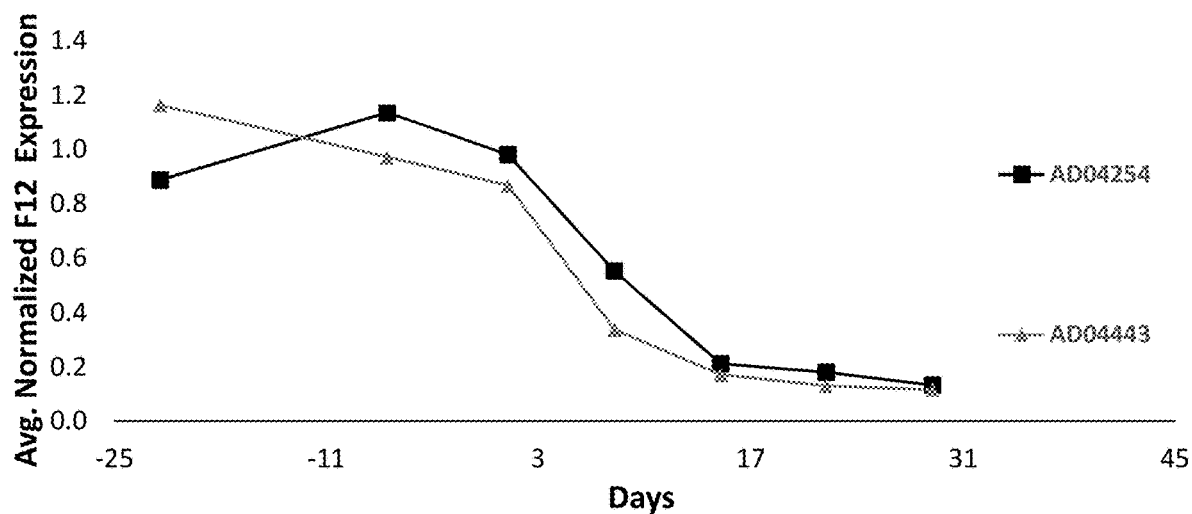
FIG. 1. Graph showing relative cF12 expression in cynomolgus monkeys after administration of RNAi agents having sequences directed to Factor 12. Only AD04443 included a 5'-cyclopropyl phosphonate modified nucleotide, which was positioned at the 5' terminus of the antisense strand.

Described herein are 5'-cyclo-phosphonate modified nucleotides, and RNAi agents (also referred to as RNAi triggers) containing 5'-cyclo-phosphonate modified nucleotides. In some embodiments, one or more 5'-cyclo-phosphonate modified nucleotides are linked to the terminus of an RNAi agent and form the terminal nucleotide of the RNAi agent. In some embodiments, the 5'-cyclo-phosphonate modified nucleotides are linked to the 5' terminus or 5' terminal end of an RNAi agent and form the terminal nucleotide on the 5' end of an RNAi agent. In some embodiments, the 5'-cyclo-phosphonate modified nucleotides are linked to the 5' terminus of the antisense strand of a double-stranded RNAi agent and form the terminal nucleotide on the 5' end of the antisense strand of a double-stranded RNAi agent.

The 5'-cyclo-phosphonate modified nucleotides disclosed herein have a cyclic group or cyclic moiety located at the 5' carbon of the sugar (or at a comparable position of a sugar surrogate replacement moiety) of the nucleotide.

In some embodiments, the 5' terminal nucleotide of an RNAi agent comprises or is a 5'-cyclo-phosphonate modified nucleotide. In some embodiments, the 5' terminal nucleotide of the antisense strand of a double-stranded RNAi agent comprises or is a 5'-cyclo-phosphonate modified nucleotide. In some embodiments, a 5'-cyclo-phosphonate modified nucleotide located at the terminal 5' end of an oligomeric compound, such as a single-stranded RNAi agent or on the antisense strand of a double-stranded RNAi agent, facilitates the loading of the oligomeric compound to which it is attached into RISC to undergo the RNAi mechanism.

In some embodiments, one or more 5'-cyclo-phosphonate modified nucleotides are linked to the terminus of a single-stranded antisense oligonucleotide and form the terminal nucleotide of the single-stranded antisense oligonucleotide. In some embodiments, the 5'-cyclo-phosphonate modified nucleotides are linked to the 5' terminus of a single-stranded antisense oligonucleotide and form the terminal nucleotide on the 5' end of a single-stranded antisense oligonucleotide.

In some embodiments, the disclosed compounds have the structure represented by Formula A, set forth in the Summary section above.

In some embodiments, the disclosed compounds of Formula A have the 5'-cyclo-phosphonate structure represented by Formula I:

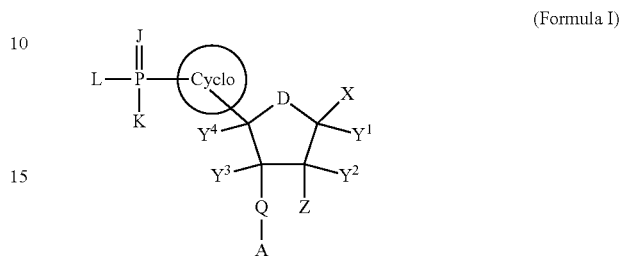

(Formula I)

wherein:

Cyclo is an optionally substituted divalent cyclic moiety having 2, 3, 4, 5, 6, 7, 8, 9, or 10 carbon atoms, such as cycloalkyl (e.g., cyclopropyl, cyclobutyl, cyclopentyl, cyclohexyl, or cycloheptyl), cycloalkenyl (e.g., cyclopentenyl, cyclobutenyl, cyclopentenyl, cyclohexenyl, or cycloheptenyl), aryl (e.g., phenyl), heteroaryl (e.g., pyridyl, pyrimidinyl, pyridazinyl, pyrrole, pyrazole, imidazole, thiophene, benzothiophene, thiazole, benzothiazole, furan, oxazole, isoxazole, benzofuran, indole, indazole, benzimidazole, oxadiazole, 1,2,3-triazole, 1,2,4-triazole, tetrazole, quinolinyl, isoquinolinyl, or quinoxalinyl), or heterocyclyl (e.g., tetrahydrofuran, tetrahydropyran, piperidine, pyrrolidine, dioxane, or dioxolane);

D is O, S, $CH_2$—$CH_2$, CH=CH, $OCH_2$, $N(R^1)$, $C(R^2)(R^3)$, $C(R^2)(R^3)C(R^4)(R^2)$, $C(R^2)$=$C(R^4)$, $OC(R^2)(R^3)$, $OC(H)(X^3)$ or $OC(R^2)(X^3)$;

$R^1$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

$R^2$, $R^3$, and $R^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

when D is O, S, $CH_2$—$CH_2$, CH=CH, $OCH_2$, $N(R^1)$, $C(R^2)(R^3)$, $C(R^2)(R^3)C(R^4)(R^2)$, $C(R^2)$=$C(R^4)$, $OC(R^2)(R^3)$, then X is a heterocyclic base moiety;

when D is $OC(H)(X^3)$ or $OC(R^2)(X^3)$, X is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl and $X^3$ is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C$(=O)—$N(H)CH_3$, —$OCH_2C$(=O)—$N(H)$—$(CH_2)_2$—$N(CH_3)_2$, —$O(CH_2)_2$—$N(H)$—$C$(=$NH$)($NH_2$), —$O(CH_2)_3$—$N(R^5)(R^6)$, —$O(CH_2)_2$—$ON(R^5)(R^6)$, —$O(CH_2)_2$—$O(CH_2)_2$—$N(R^5)(R^6)$, —$OCH_2C$(=O)—$N(R^5)(R^6)$, —$OCH_2C$(=O)—$N(R^7)$—$(CH_2)_2$—$N(R^5)(R^6)$—$O(CH_2)_2$—$N(R^7)$—$C$(=$R^8$)[$N(R^5)(R^6)$], optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

$Y^1$, $Y^2$, $Y^3$, and $Y^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl; or, alternatively, $Y^4$ is linked to one of $Y^1$ or $Y^2$, wherein the linkage comprises a divalent group selected from O, S, $NR^9$, $C(R^{10})(R^{11})$, $C(R^{10})=C(R^{11})$, $C[=C(R^{10})(R^{11})]$ and $C(=O)$, and the other two of $Y^1$, $Y^2$, and $Y^3$, are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein each $R^9$, $R^{10}$ and $R^{11}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

J is O, S, $NR^{12}$, $N-N(R^{13})_2$, or $N-OR^{13}$, wherein:

$R^{12}$ is H, OH, halogen, $C_1$-$C_{10}$ alkyl, $C_2$-$C_6$ alkenyl, $C_2$-$C_6$ alkynyl, aryl, or

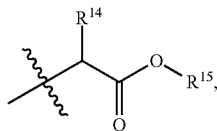

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)NH$_2$, wherein $R^{15}$ is selected from H, $C_1$-$C_{18}$ alkyl, or aryl;

wherein $R^{13}$ is H, $C_1$-$C_{10}$ alkyl, $C_2$-$C_6$ alkenyl, $C_2$-$C_6$ alkynyl, aryl, or

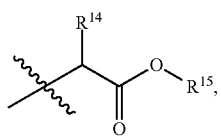

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)NH$_2$, and wherein $R^{15}$ is selected from H, $C_1$-$C_{18}$ alkyl, or aryl; and K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

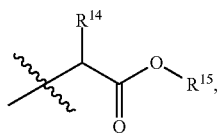

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo or —NH—C=(NH)NH$_2$, and $R^{15}$ is selected from H, $C_1$-$C_{18}$ alkyl, or aryl;

Q is a divalent moiety selected from O, S, $N(R^{30})$, or $C(R^{30})$, or $C(R^{31})(R^{32})$, wherein $R^{30}$ is H, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, and $R^{31}$ and $R^{32}$ are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl; and A is (i) an internucleoside linkage that links the 5'-cyclo-phosphonate modified nucleotide of Formula I to the remainder of the RNAi agent, or (ii) a phosphoramidite group.

In some embodiments, when A is a phosphoramidite group, A is linked to Q in Formula I by coupling Q with a phosphoramidite forming reagent, thereby forming a phosphoramidite compound.

In some embodiments, Q in Formula I is O.

In some embodiments, the disclosed compounds have the 5'-cyclo-phosphonate structure represented by Formula II:

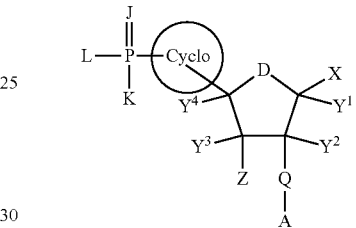

(Formula II)

wherein, Cyclo, D, X, Z, $Y^1$, $Y^2$, $Y^3$, $Y^4$, J, K, L, Q and A are each as defined in connection with Formula I, above.

In some embodiments, $Y^1$, $Y^2$, $Y^3$, and $Y^4$ in the structure Formula I and Formula II are each H.

In some embodiments, Cyclo in the structure of Formula I and Formula II is a cycloalkyl comprising 3, 4, 5, 6 or 7 carbon atoms.

In some embodiments, Cyclo in the structure of Formula I and Formula II is a cycloalkenyl comprising 4, 5, 6, or 7 carbon atoms.

In some embodiments, Cyclo in the structure of Formula I and Formula II is a cycloalkynyl comprising 5, 6, or 7 carbon atoms.

In some embodiments, Cyclo in the structure of Formula I and Formula II is aryl comprising 3, 4, 5, 6, or 7 carbon atoms.

In some embodiments, Cyclo in the structure of Formula I and Formula II is a heterocyclyl group comprising 2, 3, 4, 5 or 6 carbon atoms and one or more non-carbon atoms.

In some embodiments, Cyclo in the structure of Formula I and Formula II is an aryl or a heterocyclyl group comprising 2, 3, 4, 5, or 6 carbon atoms and one or more non-carbon atoms.

In some embodiments, Cyclo in the structure of Formula I and Formula II is a bicyclic group.

In some embodiments, Cyclo in the structure of Formula I and Formula II is selected from the group consisting of:

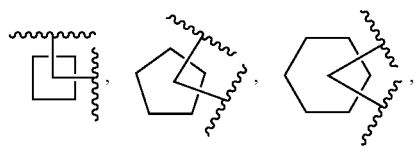

-continued

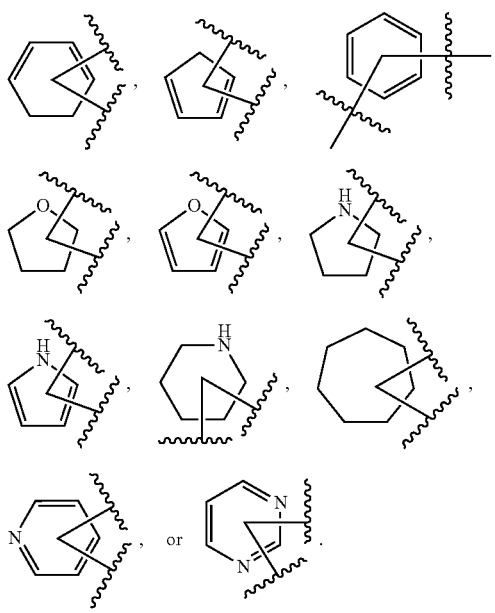

In some embodiments, Cyclo in the structure of Formula I and Formula II is a cyclic functional group in which the cyclic functional group is linked to the phosphonate moiety and the sugar ring of Formulas I and II at the following positions of the cyclic functional group, denoted using standard IUPAC nomenclature: 1,2; 1,3; 1,4; 1,5; 1,6; 1,7; 2,3; 2,4; 2,5; 2,6; 2,7; 3,4; 3,5; 3,6; 3,7; 4,5; 4,6; 4,7; 5,6; 5,7; or 6,7.

In some embodiments, Cyclo in the structure of Formula I and Formula II is selected from the group consisting of:

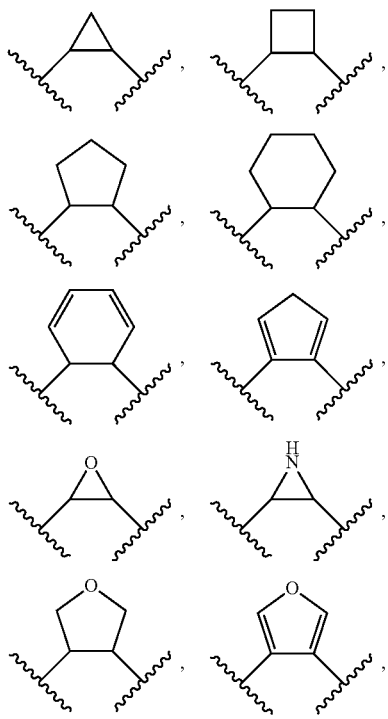

-continued

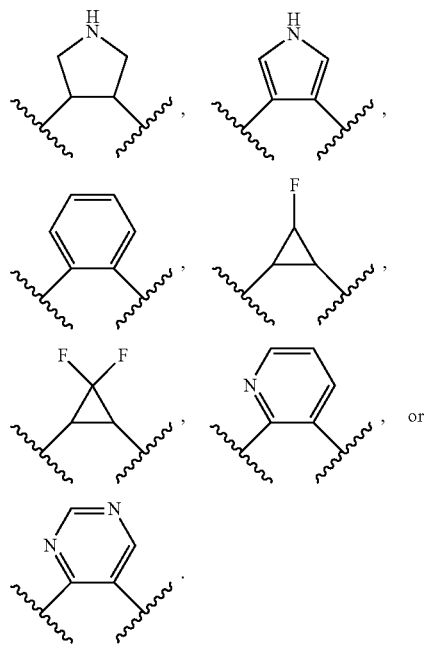

In some embodiments, Cyclo in the structure of Formula I and Formula II is substituted. In some embodiments, Cyclo in the structure of Formula I and Formula II is a substituted cyclic moiety linked to the phosphonate moiety and the sugar ring of Formula I and Formula II at the following positions of the substituted cyclic functional group, denoted using standard IUPAC nomenclature: 1,2; 1,3; 1,4; 1,5; 1,6; 1,7; 2,3; 2,4; 2,5; 2,6; 2,7; 3,4; 3,5; 3,6; 3,7; 4,5; 4,6; 4,7; 5,6; 5,7; or 6,7.

In some embodiments, Cyclo in the structure of Formula I and Formula II is a cyclopropyl group having a specific stereochemistry, such as:

In some embodiments, Cyclo in the structure of Formula I and Formula II is a substituted cyclopropyl functional group selected from the group consisting of:

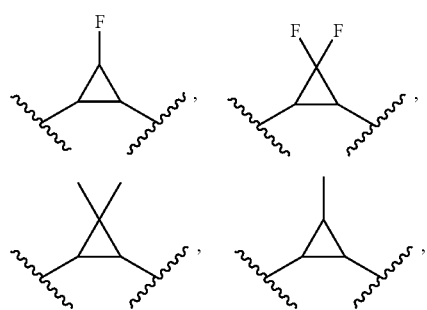

-continued

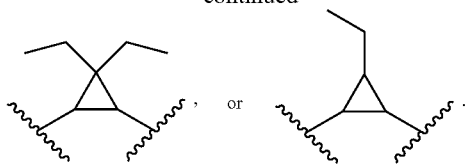

In some embodiments, the disclosed compounds have the structure represented by Formula I-a or Formula II-a:

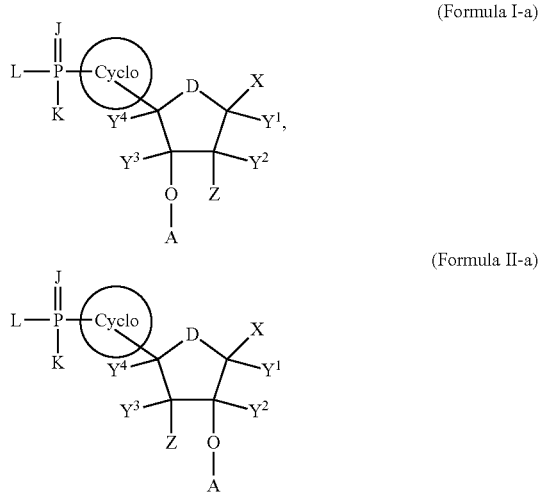

(Formula I-a)

(Formula II-a)

wherein, Cyclo, D, X, Z, $Y^1$, $Y^2$, $Y^3$, $Y^4$, J, K, L, and A are each as defined in connection with Formula I and Formula II, above.

As used herein, unless denoted otherwise, reference to Formula I includes reference to Formula I-a and Formula I-b, and reference to Formula II includes reference to Formula II-a and Formula II-b, provided that such reference would be understood as being applicable by the person of ordinary skill in the art in view of the disclosure herein.

In some embodiments, the heterocyclic base moiety (e.g., X in the structure of any of Formulas I-VIII (including all Formula subgroups or species (e.g., Formula I-b-5)) is a pyrimidine, substituted pyrimidine, purine, or substituted purine. In some embodiments, the heterocyclic base moiety is a naturally occurring purine or substituted purine. In some embodiments, the heterocyclic base moiety is a non-naturally occurring purine or substituted purine. In some embodiments, the heterocyclic base moiety is a naturally occurring pyrimidine or substituted pyrimidine. In some embodiments, the heterocyclic base moiety is a non-naturally occurring pyrimidine or substituted pyrimidine.

In some embodiments, the heterocyclic base moiety (e.g., X in the structure of any of Formulas I-VIII (including all Formula subgroups or species (e.g., Formula I-b-5)) is uracil, thymine, cytosine, 5-methylcytosine, adenine, guanine, or inosine.

In some embodiments, the heterocyclic base moiety (e.g., X in the structure of any of Formulas (including all Formula subgroups or species (e.g., Formula I-b-5)) is substituted uracil, substituted thymine, substituted cytosine, substituted 5-methylcytosine, substituted adenine, substituted guanine, or substituted inosine. In some embodiments, the substituted group is a protecting group.

In some embodiments, an isotope of hydrogen, such as deuterium or tritium, may be incorporated at one or more positions where hydrogen is present. In some embodiments, isotopes of other atoms are present (e.g., C, O, or F).

In some embodiments, the disclosed compounds have the 5'-cyclopropyl phosphonate structures represented by Formula I-b or Formula II-b:

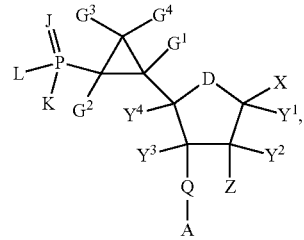

(Formula I-b)

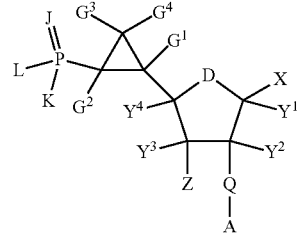

(Formula II-b)

wherein:
D is O, S, $CH_2$—$CH_2$, CH=CH, $OCH_2$, $N(R^1)$, $C(R^2)(R^3)$, $C(R^2)(R^3)C(R^4)(R^2)$, $C(R^2)$=$C(R^4)$, $OC(R^2)(R^3)$, $OC(H)(X^3)$ or $OC(R^2)(X^3)$;

$R^1$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

$R^2$, $R^3$, and $R^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

when D is O, S, $CH_2$—$CH_2$, CH=CH, $OCH_2$, $N(R^1)$, $C(R^2)(R^3)$, $C(R^2)(R^3)C(R^4)(R^2)$, $C(R^2)$=$C(R^4)$, $OC(R^2)(R^3)$, then X is a heterocyclic base moiety;

when D is $OC(H)(X^3)$ or $OC(R^2)(X^3)$, X is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl and $X^3$ is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C$(=O)—N(H)$CH_3$, —$OCH_2C$(=O)—N(H)—$(CH_2)_2$—N$(CH_3)_2$, —$O(CH_2)_2$—N(H)—C(=NH)(NH$_2$), —$O(CH_2)_3$—$N(R^5)(R^6)$, —$O(CH_2)_2$—$ON(R^5)(R^6)$, —$O(CH_2)_2$—O$(CH_2)_2$—$N(R^5)(R^6)$, —$OCH_2C$(=O)—$N(R^5)(R^6)$, —$OCH_2C$(=O)—$N(R^7)$—$(CH_2)_2$—$N(R^5)(R^6)$—$O(CH_2)_2$—$N(R^7)$—C(=$R^8$)[$N(R^5)(R^6)$], optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

$Y^1$, $Y^2$, $Y^3$, and $Y^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl; or, alternatively, $Y^4$ is linked to one of $Y^1$ or $Y^2$, wherein the linkage comprises a divalent group selected from O, S, $NR^9$, $C(R^{10})(R^{11})$, $C(R^{10})=C(R^{11})$, $C[=C(R^{10})(R^{11})]$ and $C(=O)$, and the other two of $Y^1$, $Y^2$, and $Y^3$, are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein each $R^9$, $R^{10}$ and $R^{11}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

J is O, S, $NR^{12}$, $N-N(R^{13})_2$, or $N-OR^{13}$, wherein:

$R^{12}$ is H, OH, halogen, $C_1$-$C_{10}$ alkyl, $C_2$-$C_6$ alkenyl, $C_2$-$C_6$ alkynyl, aryl, or

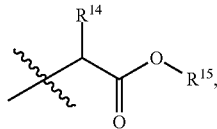

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)$NH_2$, wherein $R^{15}$ is selected from H, $C_1$-$C_{18}$ alkyl, or aryl;

wherein $R^{13}$ is H, $C_1$-$C_{10}$ alkyl, $C_2$-$C_6$ alkenyl, $C_2$-$C_6$ alkynyl, aryl, or

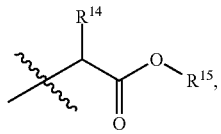

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)$NH_2$, and wherein $R^{15}$ is selected from H, $C_1$-$C_{18}$ alkyl, or aryl;

K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

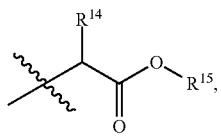

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo or —NH—C=(NH)$NH_2$, and $R^{15}$ is selected from H, $C_1$-$C_{18}$ alkyl, or aryl;

Q is a divalent moiety selected from O, S, $N(R^{30})$, or $C(R^{31})(R^{32})$, wherein $R^{30}$ is H, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, and $R^{31}$ and $R^{32}$ are each, independently, H, halogen, optionally substituted $C_1$-$C_6$ alkyl, optionally substituted $C_1$-$C_6$ alkyl alkoxy, optionally substituted $C_2$-$C_6$ alkenyl, or optionally substituted $C_2$-$C_6$ alkynyl;

$G^1$, $G^2$, $G^3$ and $G^4$ are each independently selected from the group consisting of H, F, halogen, $C_1$-$C_6$ alkyl, CN, $CH_2(R^{33})$, $CH_2$—O—$(R^{33})$, $C(=O)(R^{33})$, $C(=S)(R^{33})$, or $(R^{34})(R^{33})$, wherein $R^{33}$ is $O(R^{35})$, $S(R^{35})$, $N(R^{35})(R^{36})$, wherein $R^{34}$, $R^{35}$, and $R^{36}$ are each independently selected from H, halogen, or $C_1$-$C_6$ alkyl; and A is (i) an internucleoside linkage that links the 5-cyclophosphonate modified nucleotide of Formula I-b or Formula II-b to the remainder of the RNAi agent, or (ii) a phosphoramidite group.

As used herein, unless denoted otherwise, reference to Formula I-b includes reference to Formula I-b-1, Formula I-b-2, Formula I-b-3, Formula I-b-4, Formula I-b-5 and reference to Formula II-b includes reference to Formula II-b-1, Formula II-b-2, Formula II-b-3, Formula II-b-4, and Formula II-b-5, provided that such reference would be understood as being applicable by the person of ordinary skill in the art in view of the disclosure herein.

In some embodiments, the disclosed compounds have the 5'-cyclopropyl phosphonate structures represented by Formula I-b-1 or Formula II-b-1:

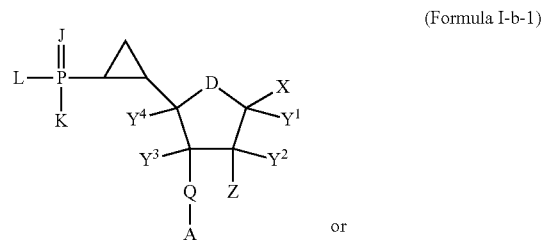

(Formula I-b-1)

or

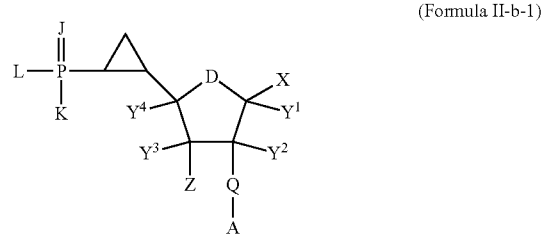

(Formula II-b-1)

wherein, D, X, Z, $Y^1$, $Y^2$, $Y^3$, $Y^4$, J, K, L, A and Q are each as defined in connection with Formula I-b and Formula II-b, above.

In some embodiments, the disclosed compounds have the structure represented by Formula I-b-2 or Formula II-b-2:

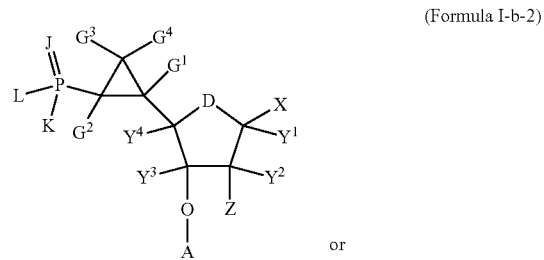

(Formula I-b-2)

or

-continued

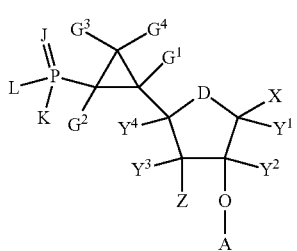
(Formula II-b-2)

wherein, D, X, Z, $Y^1$, $Y^2$, $Y^3$, $Y^4$, J, K, L, $G^1$, $G^2$, $G^3$, $G^4$ and A are each as defined in connection with Formula I-b and Formula II-b, above.

In some embodiments, the disclosed compounds have the structure represented by Formula I-b-3 or Formula II-b-3:

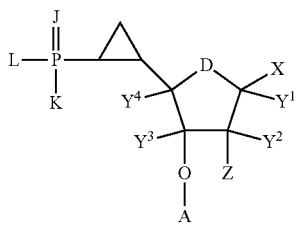
(Formula I-b-3)

or

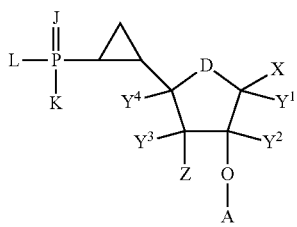
(Formula II-b-3)

wherein, D, X, Z, $Y^1$, $Y^2$, $Y^3$, $Y^4$, J, K, L, and A are each as defined in connection with Formula I-b and Formula II-b, above.

In some embodiments, the disclosed compounds have the structure represented by Formula I-b-4 or Formula II-b-4:

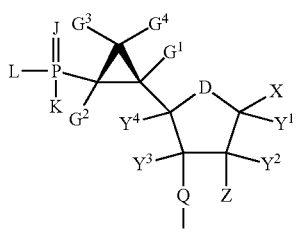
(Formula I-b-4)

or

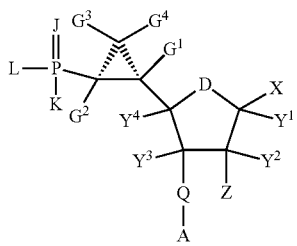
(Formula II-b-4)

wherein, D, X, Z, $Y^1$, $Y^2$, $Y^3$, $Y^4$, J, K, L, Q, A, $G^1$, $G^2$, $G^3$, and $G^4$ are each as defined in connection with Formula I-b and Formula II-b, above.

In some embodiments, the 5' terminus (or terminal nucleotide) of the antisense strand of a double-stranded RNAi agent is a 5'-cyclopropyl phosphonate modified nucleotide represented by the following Formula III or Formula IV:

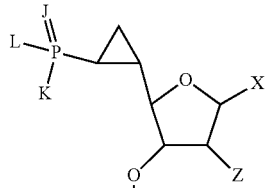
(Formula III)

or

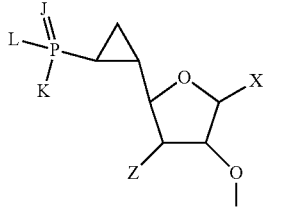
(Formula IV)

wherein:

X is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C$(=O)—N(H)$CH_3$, —$OCH_2C$(=O)—N(H)—$(CH_2)_2$—N$(CH_3)_2$, —$O(CH_2)_2$—N(H)—C(=NH)($NH_2$), —$O(CH_2)_3$—N($R^5$)($R^6$), —$O(CH_2)_2$—ON($R^5$)($R^6$), —$O(CH_2)_2$—O$(CH_2)_2$—N($R^5$)($R^6$), —$OCH_2C$(=O)—N($R^5$)($R^6$), —$OCH_2C$(=O)—N($R^7$)—$(CH_2)_2$—N($R^5$)($R^6$)—O$(CH_2)_2$—N($R^7$)—C(=$R^8$)[N($R^5$)($R^6$)], optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

J and J' are each independently, O or S;

L, L', and K are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

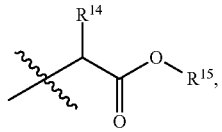

wherein $R^{14}$ is selected from H or $C_1$-$C_4$ alkyl optionally substituted with one to three substituents independently selected from SH, S—(C$_1$-C$_4$ alkyl), aryl optionally substituted with hydroxyl, heteroaryl optionally substituted with hydroxyl, amino, hydroxyl, oxo or —NH—C=(NH)NH$_2$, and R$^{15}$ is selected from H, C$_1$-C$_{18}$ alkyl, or aryl; and 〜〜〜 includes the remainder of the RNAi agent.

In some embodiments, the 5' terminus (or terminal nucleotide) of the antisense strand of a double-stranded RNAi agent is a 5'-cyclopropyl phosphonate modified nucleotide represented by the following Formula III-a or Formula IV-a:

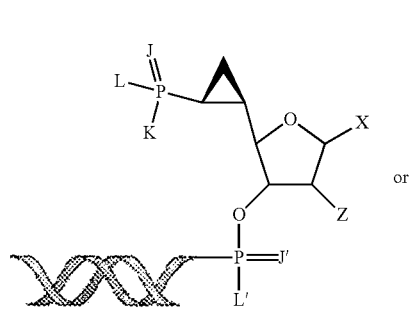

(Formula III-a)

or

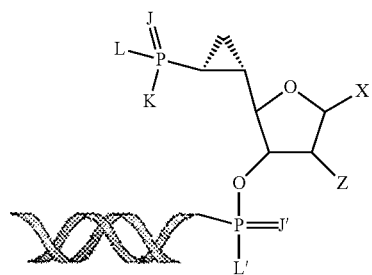

(Formula IV-a)

wherein, X, Z, J, K, L, J', L' and 〜〜〜 are each as defined in connection with Formula III and Formula IV, above.

In some embodiments, the 5' terminus (or terminal nucleotide) of the antisense strand of a double-stranded RNAi agent is a 5'-cyclopropyl phosphonate modified nucleotide represented by the following Formula III-b and Formula IV-b:

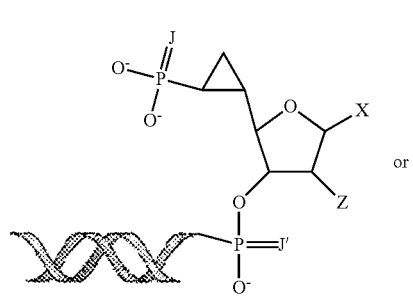

(Formula III-b)

or

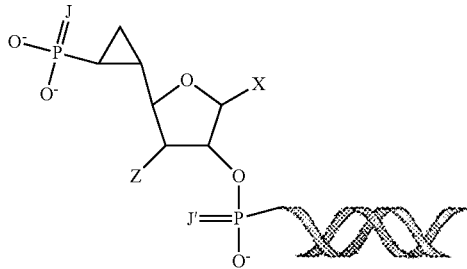

(Formula IV-b)

wherein, X, Z, J, J' and 〜〜〜 are each as defined in connection with Formula III and Formula IV, above.

In some embodiments, the 5' terminus (or terminal nucleotide) of the antisense strand of a double-stranded RNAi agent is a 5'-cyclopropyl phosphonate modified nucleotide, wherein the modified nucleotide includes a Thymine heterocyclic base moiety and a 2'-methoxyethyl (2'-O-2-methoxylethyl or "2'-MOE") modification (cPrpTMs), as represented by the following Structure i:

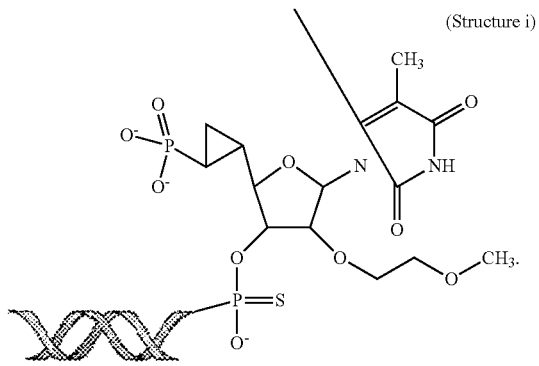

(Structure i)

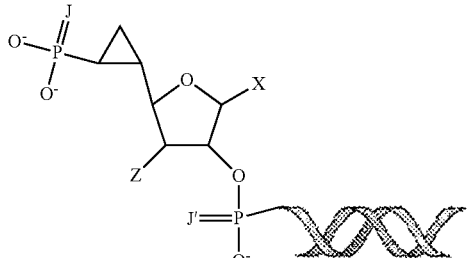

(Formula IV-b)

In some embodiments, the 5' terminus (or terminal nucleotide) of the antisense strand of a double-stranded RNAi agent is a 5'-cyclopropyl phosphonate modified nucleotide, wherein the modified nucleotide includes a Thymine heterocyclic base moiety and a 2'-methoxyethyl (2'-O-2-methoxylethyl or "2'-MOE") modification (cPrpTM), as represented by the following Structure ii:

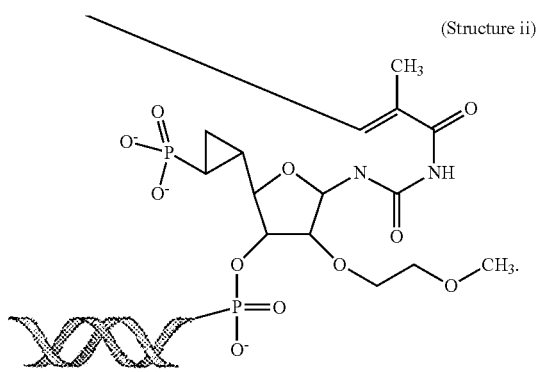

In some embodiments, the 5' terminus (or terminal nucleotide) of the antisense strand of a double-stranded RNAi agent is a 5'-cyclopropyl phosphonate modified nucleotide, wherein the modified nucleotide includes a Thymine heterocyclic base moiety and a 2'-H modification (cPrpdT), as represented by the following Structure iii:

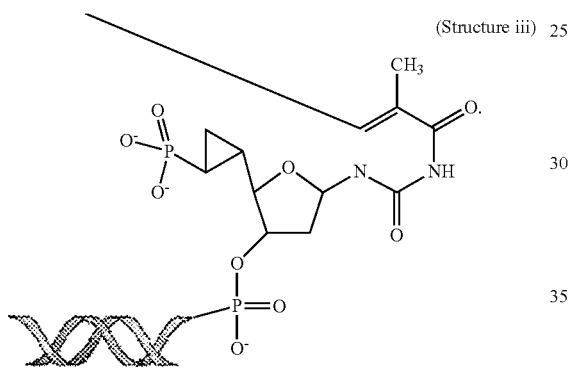

In some embodiments, the 5' terminus (or terminal nucleotide) of the antisense strand of a double-stranded RNAi agent is a 5'-cyclopropyl phosphonate modified nucleotide, wherein the modified nucleotide includes a Uracil heterocyclic base moiety and a 2'-methoxyethyl (2'-O-2-methoxylethyl or "2'-MOE") modification (cPrpUMs), represented by the following Structure iv:

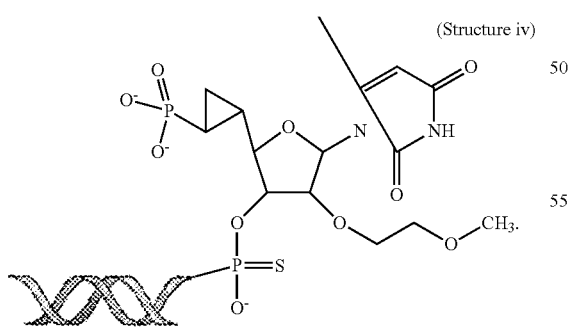

In some embodiments, the 5' terminus (or terminal nucleotide) of the antisense strand of a double-stranded RNAi agent is a 5'-cyclopropyl phosphonate modified nucleotide, wherein the modified nucleotide includes a Uracil heterocyclic base moiety and a 2'-O-methyl modification (cPrpu), represented by the following Structure v:

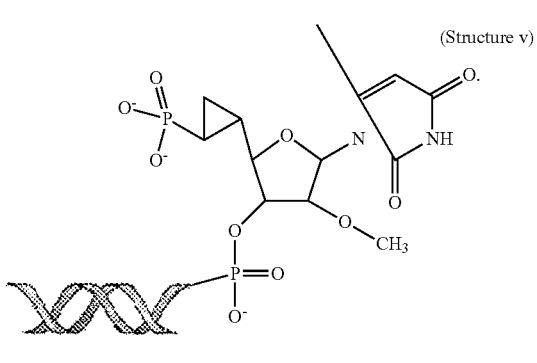

In some embodiments, the 5' terminus (or terminal nucleotide) of the antisense strand of a double-stranded RNAi agent is a 5'-cyclopropyl phosphonate modified nucleotide, wherein the modified nucleotide includes a Uracil heterocyclic base moiety and a 2'-O-methyl modification (cPrpus), represented by the following Structure vi:

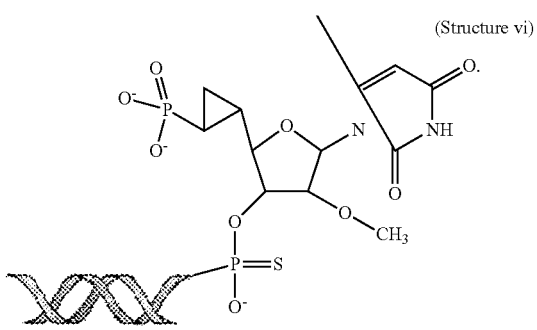

In some embodiments, the 5' terminus (or terminal nucleotide) of the antisense strand of a double-stranded RNAi agent is a 5'-cyclopropyl phosphonate modified nucleotide, wherein the modified nucleotide includes a Uracil heterocyclic base moiety and a 2'-deoxy modification (cPrpdU), represented by the following Structure vii:

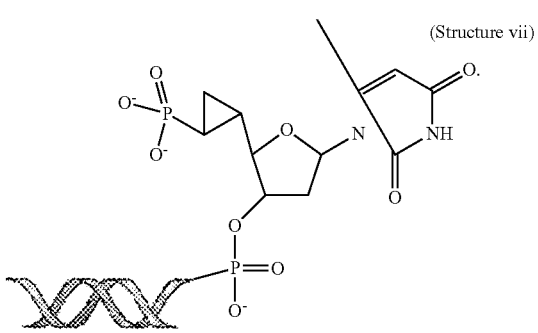

In some embodiments, the 5' terminus (or terminal nucleotide) of the anti sense strand of a double-stranded RNAi agent is a 5'-cyclopropyl phosphonate modified nucleotide, wherein the modified nucleotide includes a Uracil heterocyclic base moiety and a 2'-O-methyl modification (cPrpdUs), represented by the following Structure viii:

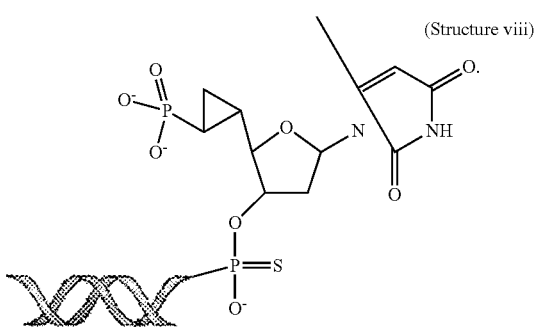

(Structure viii)

In some embodiments, the 5' terminus (or terminal nucleotide) of the antisense strand of a double-stranded RNAi agent is a 5'-cyclopropyl phosphonate modified nucleotide, wherein the modified nucleotide includes a Adenine heterocyclic base moiety and a 2'-O-methyl modification (cPrpa), represented by the following Structure ix:

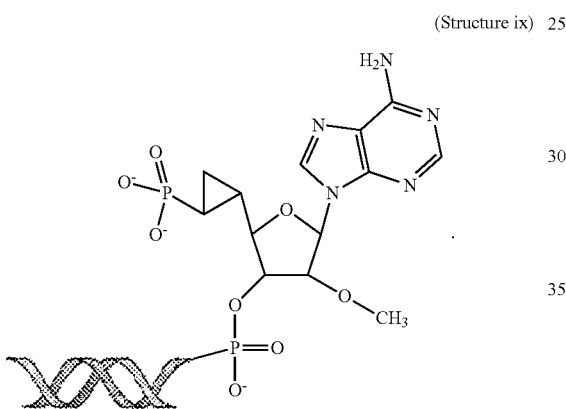

(Structure ix)

In some embodiments, the 5' terminus (or terminal nucleotide) of the anti sense strand of a double-stranded RNAi agent is a 5'-cyclopropyl phosphonate modified nucleotide, wherein the modified nucleotide includes a Adenine heterocyclic base moiety and a 2'-O-methyl modification (cPrpas), represented by the following Structure x:

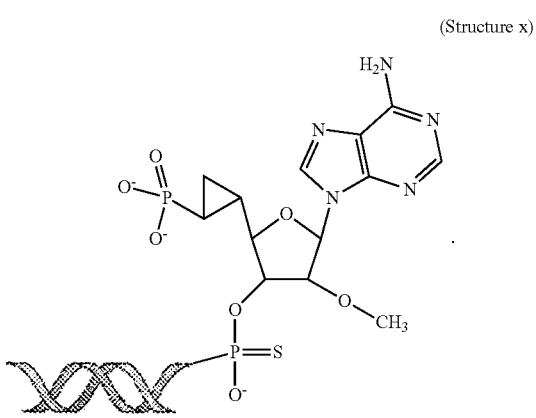 [SMILES: COC1C(OP(C)([O-])=S)C(C2CC2P(=O)([O-])[O-])OC1n1cnc2c(N)ncnc21]

(Structure x)

In some embodiments, Structure i, ii, iii, iv, v, vi, vii, viii, ix, or x may be positioned at the 5' terminus (terminal nucleotide) of the antisense strand of a double-stranded RNAi agent.

In some embodiments, Structure i, ii, iii, iv, v, vi, vii, viii, ix, or x may be positioned at the 5' terminus (terminal nucleotide) of a single-stranded antisense oligonucleotide.

Structures i-x are merely exemplary in nature. As discussed elsewhere herein, for example, a sugar surrogate replacement moiety may be used in connection with the above structures to change the 5-membered furanose ring to a different structure capable of replacing the 5-membered furanose ring, such as a morpholino, cyclohexenyl, cyclohexitol, or an acyclic structure. Such changes are contemplated and within the scope of the inventions disclosed herein.

In some embodiments, a 5'-phosphonate mimic, such as 5'-C-malonyl group, is to a cyclopropyl group, and the terminus (or terminal nucleotide) of the antisense strand of an RNAi agent is a 5'-cyclopropyl-C-malonyl modified nucleotide represented by the following Formula V and VI:

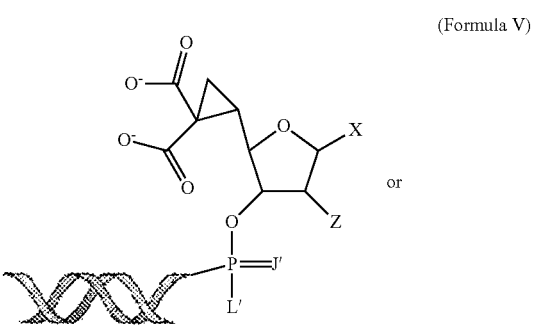

(Formula V)

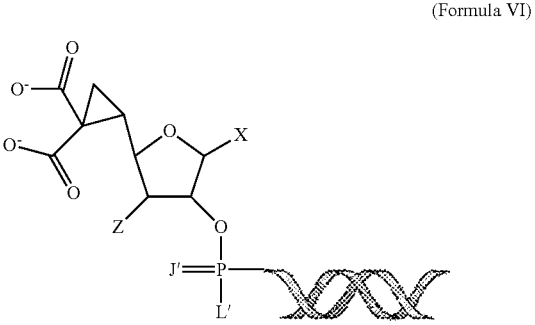

(Formula VI)

wherein:

X is a heterocyclic base moiety;

Z is H, —OH, F, $OCH_3$, —O—$(CH_2)_2$—$OCH_3$; halogen; —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$O(CH_2)_2$—$O(CH_2)_2$—$N(CH_3)_2$, —$OCH_2C$(=O)—N(H)$CH_3$, —$OCH_2C$(=O)—N(H)—$(CH_2)_2$—N$(CH_3)_2$, —$O(CH_2)_2$—N(H)—C(=NH)($NH_2$), —$O(CH_2)_3$—$N(R^5)(R^6)$, —$O(CH_2)_2$—$ON(R^5)(R^6)$, —$O(CH_2)_2$—$O$($CH_2)_2$—$N(R^5)(R^6)$, —$OCH_2C$(=O)—$N(R^5)(R^6)$, —$OCH_2C$(=O)—$N(R^7)$—$(CH_2)_2$—$N(R^5)(R^6)$—$O(CH_2)_2$—$N(R^7)$—C(=$R^8$)[$N(R^5)(R^6)$], optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein $R^5$, $R^6$, $R^7$ and $R^8$ are each, independently, H or $C_1$-$C_6$ alkyl;

J and J' are each independently O or S; and

L' is selected from OH, OR$^{16}$, SR$^{16}$, or NR$^{16}$, wherein R$^{16}$ is selected from H, $C_1$-$C_{10}$ alkyl, $C_2$-$C_6$ alkenyl, $C_2$-$C_6$ alkynyl, aryl, or

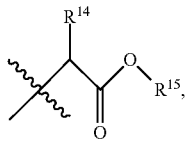

wherein R$^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo or —NH—C=(NH)NH$_2$, and R$^{15}$ is selected from H, $C_1$-$C_{18}$ alkyl, or aryl; and ⁀⁀⁀ includes the remainder of the RNAi agent.

The person of ordinary skill in the art would readily understand and appreciate that under sufficiently basic conditions, the protic groups of Formulas I, II, III, IV, V, VI, VII, and/or VIII (including Formula subgroups or species (e.g., Formula I-b-5)) and/or Structures i, ii, iii, iv, v, vi, vii, viii, ix, x, xi, xii, and/or xiii exist in a partially or fully deprotonated state. Likewise, under sufficiently acidic conditions, groups that include a basic site or atom are protonated. All such protonated and deprotonated versions of the groups disclosed herein are encompassed within the scope of the embodiments. For example, in instances where a carboxyl group is within the scope of an embodiment or claim, the corresponding carboxylate is also within the scope of the embodiment or claim. For example, in instances where an amino group is within the scope of an embodiment or claim, the corresponding ammonium group is also within the scope of the embodiment or claim.

In some embodiments, the disclosed compounds are phosphoramidite compounds having the structure represented by Formula I-b-5 or Formula II-b-5:

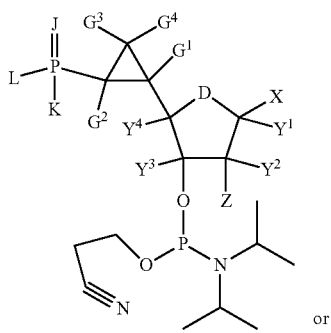

(Formula I-b-5)

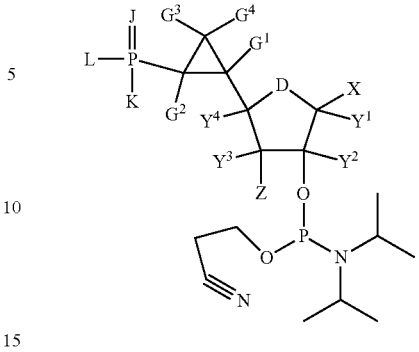

(Formula II-b-5)

wherein:

D is O, S, CH$_2$—CH$_2$, CH=CH, OCH$_2$, N(R$^1$), C(R$^2$)(R$^3$), C(R$^2$)(R$^3$)C(R$^4$)(R$^2$), C(R$^2$)=C(R$^4$), OC(R$^2$)(R$^3$), OC(H)(X$^3$) or OC(R$^2$)(X$^3$);

R$^1$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

R$^2$, R$^3$, and R$^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

when D is O, S, CH$_2$—CH$_2$, CH=CH, OCH$_2$, N(R$^1$), C(R$^2$)(R$^3$), C(R$^2$)(R$^3$)C(R$^4$)(R$^2$), C(R$^2$)=C(R$^4$), OC(R$^2$)(R$^3$), then X is a heterocyclic base moiety; when D is OC(H)(X$^3$) or OC(R$^2$)(X$^3$), X is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl and X$^3$ is a heterocyclic base moiety;

Z is H, —OH, F, OCH$_3$, —O—(CH$_2$)$_2$—OCH$_3$; halogen; —OCH$_2$F, —OCHF$_2$, —OCF$_3$, —OCH$_2$CH$_3$, —O(CH$_2$)$_2$F, —OCH$_2$CHF$_2$, —OCH$_2$CF$_3$, —OCH$_2$—CH=CH$_2$, —O(CH$_2$)$_2$—OCH$_3$, —O(CH$_2$)$_2$—SCH$_3$, —O(CH$_2$)$_2$—OCF$_3$, —O(CH$_2$)$_2$—O(CH$_2$)$_2$—N(CH$_3$)$_2$, —OCH$_2$C(=O)—N(H)CH$_3$, —OCH$_2$C(=O)—N(H)—(CH$_2$)$_2$—N(CH$_3$)$_2$, —O(CH$_2$)$_2$—N(H)—C(=NH)(NH$_2$), —O(CH$_2$)$_3$—N(R$^5$)(R$^6$), —O(CH$_2$)$_2$—ON(R$^5$)(R$^6$), —O(CH$_2$)$_2$—O(CH$_2$)$_2$—N(R$^5$)(R$^6$), —OCH$_2$C(=O)—N(R$^5$)(R$^6$), —OCH$_2$C(=O)—N(R$^7$)—(CH$_2$)$_2$—N(R$^5$)(R$^6$)—O(CH$_2$)$_2$—N(R$^7$)—C(=R$^8$)[N(R$^5$)(R$^6$)], optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein R$^5$, R$^6$, R$^7$ and R$^8$ are each, independently, H or $C_1$-$C_6$ alkyl;

Y$^1$, Y$^2$, Y$^3$, and Y$^4$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl; or, alternatively, Y$^4$ is linked to one of Y$^4$ or Y$^2$, wherein the linkage comprises a divalent group selected from O, S, NR$^9$, C(R$^{10}$)(R$^{11}$), C(R$^{10}$)=C(R$^{11}$), C[=C(R$^{10}$)(R$^{11}$)] and C(=O), and the other two of Y$^1$, Y$^2$, and Y$^3$, are each, independently, H, halogen, optionally substituted $C_1$-$C_6$ alkyl, optionally substituted $C_1$-$C_6$ alkoxy, optionally substituted $C_2$-$C_6$ alkenyl, or optionally substituted $C_2$-$C_6$ alkynyl, wherein each R$^9$, R$^{10}$ and R$^{11}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

J is O, S, $NR^{12}$, $N-N(R^{13})_2$, or $N-OR^{13}$, wherein:

$R^{12}$ is H, OH, halogen, $C_1$-$C_{10}$ alkyl, $C_2$-$C_6$ alkenyl, $C_2$-$C_6$ alkynyl, aryl, or

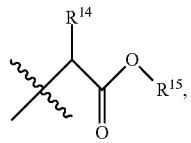

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)NH$_2$, wherein $R^{15}$ is selected from H, $C_1$-$C_{18}$ alkyl, or aryl;

wherein $R^{13}$ is H, $C_1$-$C_{10}$ alkyl, $C_2$-$C_6$ alkenyl, $C_2$-$C_6$ alkynyl, aryl, or

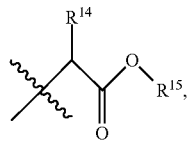

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo, or NH—C=(NH)NH$_2$, and wherein $R^{15}$ is selected from H, $C_1$-$C_{18}$ alkyl, or aryl;

K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

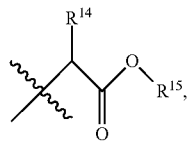

wherein $R^{14}$ is selected from H or $C_1$-$C_4$ alkyl optionally substituted with one to three substituents independently selected from SH, S—($C_1$-$C_4$ alkyl), aryl optionally substituted with hydroxyl, heteroaryl optionally substituted with hydroxyl, amino, hydroxyl, oxo or —NH—C=(NH)NH$_2$, and $R^{15}$ is selected from H, $C_1$-$C_{18}$ alkyl, or aryl; and $G^1$, $G^2$, $G^3$ and $G^4$ are each independently selected from the group consisting of H, F, halogen, $C_1$-$C_6$ alkyl, CN, $CH_2(R^{33})$, $CH_2$—O—$(R^{33})$, C(=O)$(R^{33})$, C(=S)$(R^{33})$, or $(R^{34})(R^{33})$, wherein $R^{33}$ is $O(R^{35})$, $S(R^{35})$, $N(R^{35})(R^{36})$, wherein $R^{34}$, $R^{35}$, and $R^{36}$ are each independently selected from H, halogen, or $C_1$-$C_6$ alkyl.

In some embodiments, X in Formula I-b-5 and Formula II-b-5 includes one or more protecting groups.

In some embodiments, the disclosed compounds represented by Formula I-b-5 and Formula II-b-5 have the following structures:

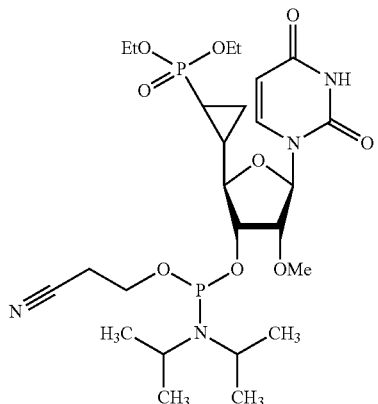

(Structure xi)

(2-cyanoethyl ((2R,3R,4R,5R)-2-(2-(diethoxyphosphoryl)cyclopropyl)-5-(2,4-dioxo-3,4-dihydropyrimidin-1(2H)-yl)-4-methoxytetrahydrofuran-3-yl) diisopropylphosphoramidite);

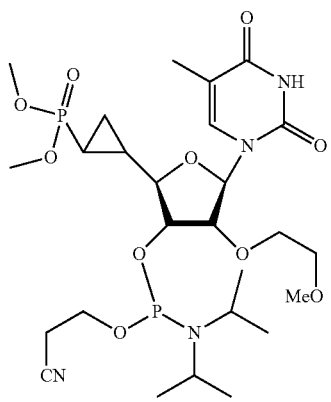

(Structure xii)

(Dimethyl [2-[(2R,3R,4R,5R)-3-([[bis(propan-2-yl)amino](2-cyanoethoxy)phosphanyl]oxy)-4-(2-methoxyethoxy)-5-(5-methyl-2,4-dioxo-1,2,3,4-tetrahydropyrimidin-1-yl)oxolan-2-yl]cyclopropyl]phosphonate); or

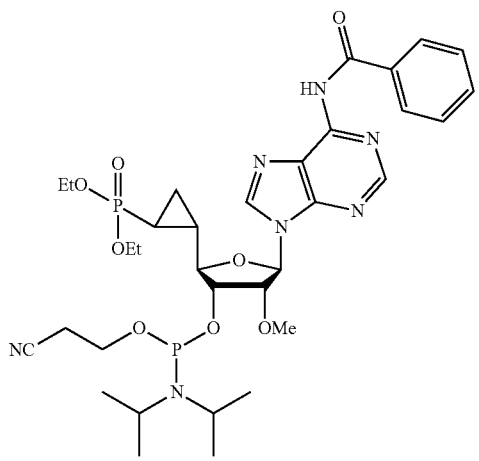

(Structure xiii)

(2R,3R,4R,5R)-5-(6-benzamido-9H-purin-9-yl)-2-(2-(diethoxyphosphoryl)cyclopropyl)-4-methoxytetrahydrofuran-3-yl (2-cyanoethyl)diisopropylphosphoramidite).

In some embodiments, Structure xi, xii, or xiii may be added to the 5' terminus (terminal nucleotide) of the antisense strand of a double-stranded RNAi agent.

In some embodiments, Structure xi, xii, or xiii may be added to the 5' terminus (terminal nucleotide) of a single-stranded antisense oligonucleotide.

Structures xi, xii, and xiii are merely exemplary in nature. As discussed elsewhere herein, for example, a sugar surrogate replacement moiety may be used in connection with the above structures to change the 5-membered furanose ring to a different structure capable of replacing the 5-membered furanose ring, such as a morpholino, cyclohexenyl, cyclohexitol, or an acyclic structure. Additionally, as discussed elsewhere herein, the modification at the 2' or 3' position of the modified nucleotide may be changed to the various modifications known in the art, and/or the heterocyclic base moiety may be modified from the specific structures depicted herein. Such changes are contemplated and within the scope of the inventions disclosed herein.

A 5'-cyclo-phosphonate modified nucleotide when in the form of a phosphoramidite compound as disclosed herein may be useful to attach the 5'-cyclo-phosphonate modified nucleotide, using methods generally known in the art for phosphoramidite synthesis of oligonucleotides. A 5'-cyclo-phosphonate modified nucleotide may be prepared as a phosphoramidite compound by linking the phosphorus atom of a phosphoramidite forming reagent through a coupling (e.g., phosphytylation) reaction, thereby forming a phosphoramidite compound.

In some embodiments, a 5'-cyclo-phosphonate modified nucleotide-phosphoramidite compound is used to link the 5'-cyclo-phosphonate modified nucleotide to the 5' terminal end of the antisense strand of a double-stranded RNAi agent. In some embodiments, a 5'-cyclo-phosphonate modified nucleotide-phosphoramidite compound is used to link the 5'-cyclo-phosphonate modified nucleotide to the 5' terminal end of a single-stranded RNAi agent.

As used herein, the RNAi agents and single-stranded antisense oligonucleotides comprising 5'-cyclopropyl phosphonate modified nucleotides described herein contain one or more asymmetric centers and thus give rise to enantiomers, diastereomers, and other stereoisomeric configurations. The configuration of any bonds appearing herein are selected solely for convenience and are not intended to limit a particular configuration, unless the text states otherwise.

In some embodiments, the disclosed compounds have the structure of Formula B represented by Formula IX or Formula X:

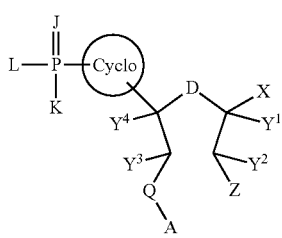

(Formula VII)

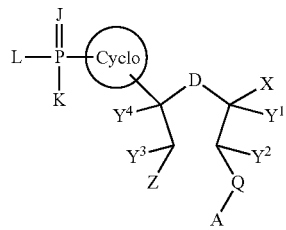

(Formula VIII)

wherein, Cyclo, D, X, Z, $Y^1$, $Y^2$, $Y^3$, $Y^4$, J, K, L, Q, and A are each as defined in connection with Formula I and Formula II, above.

RNAi Agents, Targeting Ligands, and Delivery Polymers

Oligomeric compounds having sequences at least partially complementary to a target nucleic acid, such as RNAi agents, have been shown to alter the function and activity of the target nucleic acid both in vitro and in vivo. As disclosed herein, an RNAi agent may include one or more 5'-cyclophosphonate modified nucleotides.

In some embodiments, the RNAi agents that include 5'-cyclo-phosphonate modified nucleotides disclosed herein are double-stranded. For double-stranded RNAi agents, the length of the herein described RNAi agent sense and antisense strands are independently 16 to 30 nucleotides in length. In some embodiments, a double-stranded RNAi agent includes a sense strand and an antisense strand that are at least partially complementary (at least 70% complementary) to each other. The antisense strand contains a region having a sequence that is perfectly complementary (100% complementary) or at least substantially complementary (at least 85% complementary) to a sequence in a target mRNA. The length of a double-stranded RNAi agent sense strand and antisense strand each can be 16 to 30 nucleotides in length. The sense and antisense strands can be either the same length or they can be different lengths. In some embodiments, the sense and antisense strands are each independently 17 to 26 nucleotides in length. In some embodiments, the sense and antisense strands are each independently 17-21 nucleotides in length. In some embodiments, both the sense and antisense strands are each 21-26 nucleotides in length. In some embodiments, the sense strand is about 19 nucleotides in length while the antisense strand is about 21 nucleotides in length. In some embodiments, the sense strand is about 21 nucleotides in length while the anti sense strand is about 23 nucleotides in length. In some embodiments, both the sense and antisense strands are each 26 nucleotides in length. In some embodiments, the RNAi agent sense and antisense strands are each independently 17, 18, 19, 20, 21, 22, 23, 24, 25, or 26 nucleotides in length. In some embodiments, a double-stranded RNAi agent has a duplex length of about 16, 17, 18, 19, 20, 21, 22, 23 or 24 nucleotides. This region of perfect or substantial complementarity between the sense strand and the antisense strand is typically 15-25 (e.g., 15, 16, 17, 18, 19, 20, 21, 22, 23, 24, or 25) nucleotides in length and occurs at or near the 5' end of the antisense strand (e.g., this region is separated from the 5' end of the antisense strand by 1, 2, 3, or 4 nucleotides that are not perfectly or substantially complementary). In some embodiments, a 5'-cyclophosphonate modified nucleotide is the terminal nucleotide on the 5' end of the antisense strand of a double-stranded RNAi agent.

In some embodiments, the RNAi agents that include 5'-cyclo-phosphonate modified nucleotides are single-stranded antisense oligonucleotides. In some embodiments, the length of single-stranded antisense oligonucleotides are each independently about 8 to about 40 nucleotides in length.

In some embodiments, the RNAi agents that include 5'-cyclo-phosphonate modified nucleotides are double-stranded molecules having a sense strand and an antisense strand. In some embodiments, the RNAi agents that include 5'-cyclo-phosphonate modified nucleotides are single-stranded antisense oligonucleotides.

In some embodiments, the 5'-cyclo-phosphonate modified nucleotides are linked to the terminus of an RNAi agent and enhance nuclease stability of the RNAi agent. In some embodiments, the RNAi agents disclosed herein that include a 5'-cyclo-phosphonate modified nucleotide at the teiminus, upon delivery to a cell, are able to inhibit or knockdown expression of the targeted gene in vitro or in vivo through the biological process of RNA interference (RNAi).

For double-stranded RNAi agents, the sense strand and/or the antisense strand may optionally and independently contain an additional 1, 2, 3, 4, 5, or 6 nucleotides (extension) at the 3' end, the 5' end, or both the 3' and 5' ends of the core sequences. The additional sense strand nucleotides, if present, may or may not be identical to the corresponding sequence in the targeted mRNA. The additional antisense strand nucleotides, if present, may or may not be complementary to the corresponding sense strand's additional nucleotides, if present. For single-stranded RNAi agents, additional nucleotides, if present, may or may not be complementary to the corresponding sequence in the targeted mRNA.

In some embodiments, the sense strand and the antisense strand of the double-stranded RNAi agents that include a terminal 5'-cyclophosphonate modified nucleotide described herein contain the same number of nucleotides. In some embodiments the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form a blunt end. In some embodiments, neither end of an RNAi agent is blunt-ended. As used herein, the term "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded trigger molecule in which the terminal nucleotides of the two annealed strands form a pair (i.e. do not form an overhang) but are not complementary (i.e. fouii a non-complementary pair). As used herein, an overhang is a stretch of one or more unpaired nucleotides at the end of one strand of a double stranded RNAi agent. The unpaired nucleotides may be on the sense strand or the antisense strand, creating either 3' or 5' overhangs. In some embodiments the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhand end, two frayed ends, or two blunt ends.

In some embodiments, the RNAi agent contains at least one nucleotide having a modified backbone (also referred to herein as an internucleoside linkage). In some embodiments, the modified backbone or internucleoside linkage is one or more phosphorothioate linkages.

In some embodiments, a sense strand of the RNAi agents contains 1 to 4 phosphorothioate linkages. In other embodiments, an antisense strand of the described RNAi agents contains 1 to 4 phosphorothioate linkages. In some embodiments, both the sense strand and the antisense strand contain 1 to 4 phosphorothioate linkages.

In some embodiments in which the RNAi agent is single-stranded, the RNAi agent contains phosphorothioate linkages for all or nearly all of the linkages of the nucleotides or modified nucleotides of the molecule.

In some embodiments, RNAi agents including 5'-cyclo-phosphonate modified nucleotides having the structure of Formula I, Formula II, Formula III, Formula IV, Formula V, Formula VI, Formula VII, and/or Formula VIII (including all Foi inula subgroups or species (e.g., Formula I-b-5)) and/or Structure i, Structure ii, Structure iii, Structure iv, Structure v, Structure vi, Structure vii, Structure viii, Structure ix, Structure x, Structure xi, Structure xii, and/or Structure xiii are double-stranded. Double-stranded RNAi agents can be for riled by annealing an anti sense strand with a sense strand. In some embodiments, RNAi agents including 5'-cyclo-phosphonate modified nucleotides having the structure of Formula I, Formula II, Formula III, Formula IV, Formula V, Formula VI, Formula VII, and/or Formula VIII (including all Formula subgroups or species (e.g., Formula I-b-5)) and/or Structure i, Structure ii, Structure iii, Structure iv, Structure v, Structure vi, Structure vii, Structure viii, Structure ix, Structure x, Structure xi, Structure xii, and/or Structure xiii are single-stranded oligonucleotides. The RNAi agents described herein are synthesized using methods commonly used in the art.

In some embodiments, an RNAi agent contains one or more modified nucleotides. As used herein, a "modified nucleotide" is a nucleotide other than a ribonucleotide (2'-hydroxyl nucleotide). As used herein, deoxy-ribonucleotides are considered a type of modified nucleotide. In some embodiments, at least 50%, (e.g., at least 60%, at least 70%, at least 80%, at least 90%, at least 95%, at least 97%, at least 98%, at least 99%, or 100% of the nucleotides of an RNAi agent are modified. As used herein, modified nucleotides include, but are not limited to, deoxy-ribonucleotides, nucleotide mimics, abasic nucleotides (represented herein as X, Ab), 2'-modified nucleotides, 3' to 3' linkages (inverted) nucleotides (represented herein as invdN, invN, invn, invX, invAb), non-natural base-comprising nucleotides, bridged nucleotides, peptide nucleic acids (PNAs), 2',3'-seco nucleotide mimics (unlocked nucleobase analogues, represented herein as $N_{UNA\ or}$ NUNA), locked nucleotides (represented herein as $N_{LNA}$ or NLNA), 3'-O-methoxy (2' internucleoside linked) nucleotides (represented herein as 3'-OMen), 2'-F-Arabino nucleotides (represented herein as NfANA or $Nf_{ANA}$), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e. a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O—2-methoxylethyl) nucleotides (represented herein as NM or 2'-MOE), 2'-amino nucleotides, and 2'-alkyl nucleotides. It is not necessary for all positions in a given compound to be uniformly modified. Conversely, more than one modification may be incorporated in a single RNAi agent or even in a single nucleotide thereof. The RNAi agents may be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and O-6 substituted purines, (e.g., 2-aminopropyladenine, 5-propynyluracil, or 5-propynylcytosine), 5-methylcytosine (5-me-C), 5-hydroxymethyl cytosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sultlnydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides.

In some embodiments, one or more nucleotides of an RNAi agent is a ribonucleotide. As used herein, ribonucleotides are represented herein as "N" (capital letter without further notation).

The nucleotides of an RNAi agent described herein may be linked by phosphate-containing or non-phosphate-containing covalent internucleoside linkages. Modified internucleoside linkages or backbones include, but are not limited to, 5'-phosphorothioate groups (represented herein as a lower case 's' before a nucleotide, as in sN, sn, sNf, or sdN), chiral phosphorothioates, thiophosphates, phosphorodithioates, phosphotriesters, aminoalkyl-phosphotriesters, alkyl phosphonates (e.g., methyl phosphonates or3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, an RNAi agent that includes a 5'-cyclo-phosphonate modified nucleotide inhibits expression of a target mRNA in a cell, group of cells, tissue, or subject. In some embodiments, a therapeutically effective amount of an RNAi agent that includes a 5'-cyclo-phosphonate modified nucleotide described herein is administered to a subject, thereby inhibiting the expression of a target mRNA in the subject.

In some embodiments, the described RNAi agents are used for treating, preventing, or managing clinical presentations associated with expression of a target mRNA. In some embodiments, a therapeutically or prophylactically effective amount of one or more RNAi agents is administered to a subject in need of such treatment, prevention or management.

The described RNAi agents that include 5'-cyclo-phosphonate modified nucleotides and methods can be used to treat or prevent at least one symptom in a subject having a disease or disorder that would benefit from reduction or inhibition in expression of a target mRNA. In some embodiments, the subject is administered a therapeutically effective amount of one or more RNAi agents thereby treating the at least one symptom. In other embodiments, the subject is administered a prophylactically effective amount of one or more of RNAi agents thereby preventing the at least one symptom.

In some embodiments, the gene expression level and/or mRNA level of a target in a subject to whom a described targeting ligand conjugated to an expression-inhibiting oligomeric compound is administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to administration or to a subject not receiving the targeting ligand conjugate. The gene expression level and/or mRNA level in the subject may be reduced in a cell, group of cells, and/or tissue of the subject. In some embodiments, the protein level in a subject to whom a described targeting ligand conjugated to an expression-inhibiting oligomeric compound has been administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to being administered the targeting ligand conjugate or to a subject not receiving the targeting ligand conjugate. The protein level in the subject may be reduced in a cell, group of cells, tissue, blood, and/or other fluid of the subject. A reduction in gene expression, mRNA, or protein levels can be assessed by any methods known in the art. Reduction or decrease in mRNA level and/or protein level are collectively referred to herein as inhibiting, decreasing, or reducing the expression of the targeted gene.

The RNAi agents disclosed herein that include 5'-cyclo-phosphonate modified nucleotides, and compositions comprising the RNAi agents described herein, can be delivered to a cell, group of cells, tumor, tissue, or subject using oligonucleotide delivery technologies known in the art. In general, any suitable method recognized in the art for delivering a nucleic acid molecule (in vitro or in vivo) can be adapted for use with an RNAi agent that includes one or more 5'-cyclo-phosphonate modified nucleotides as described herein. For example, delivery can be by local administration, (e.g., direct injection, implantation, or topical administering), systemic administration, or subcutaneous, intravenous, oral, intraperitoneal, or parenteral routes, including intracranial (e.g., intraventricular, intraparenchymal and intrathecal), intramuscular, transdermal, airway (aerosol), nasal, rectal, or topical (including buccal and sublingual) administration, In certain embodiments, the compositions are administered by subcutaneous or intravenous infusion or injection.

In some embodiments in which the RNAi agent is double stranded, the RNAi agent may contain a non-nucleotide group attached to the 3' or 5' end of either the sense strand or the antisense strand. In some embodiments, a targeting ligand or targeting group, a linking group, or a delivery vehicle is covalently linked to the sense strand. In some embodiments, the targeting ligand, linking group, and/or delivery vehicle is linked to the 3' end and/or the 5' end of the sense strand. In some embodiments, the targeting ligand, linking group, and/or delivery vehicle is linked to the 5' end of the sense strand. In some embodiments, a targeting ligand, linking group, and/or delivery vehicle is linked directly or indirectly via a linker to the 3' or 5' end of the sense strand. In some embodiments, a targeting ligand is linked to the RNAi agent via a labile, cleavable, or reversible bond or linker/spacer.

In some embodiments in which the RNAi agent is single-stranded, the RNAi agent may contain a targeting ligand or targeting group, linking group, or delivery vehicle attached to the end in which the terminal 5'-cyclo-phosphonate modified nucleotide is not present. In some embodiments in which the RNAi agent is single-stranded, the 5'-cyclophosphonate modified nucleotide is attached to the 5' terminus of the RNAi agent, and the targeting ligand, linking group, or delivery vehicle is attached to the 3' terminus of the RNAi agent.

In some embodiments, a delivery vehicle may be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide, a lipid, a reversibly modified polymer or peptide, or a reversibly modified membrane active polyamine.

The RNAi agents that include 5'-cyclo-phosphonate modified nucleotides can be combined with lipids, nanoparticles, polymers, liposomes, micelles, Dynamic Polyconjugates (DPC) or other delivery systems available in the art. The RNAi agents can also be chemically conjugated to targeting groups or targeting moieties, lipids (including, but not limited to cholesterol and cholesteryl derivative), nanoparticles, polymers, liposomes, micelles, DPCs (see, e.g., WO 2000/053722, WO 2008/0022309, WO 2011/104169, and WO 2012/083185, WO 2013/032829, WO 2013/158141, each of which is incorporated here by reference), or other delivery systems available in the art.

In some embodiments, one or more 5'-cyclo-phosphonate modified nucleotides linked to RNAi agents are included in pharmaceutical compositions for delivery to a cell in vivo. Such pharmaceutical compositions can include, but are not limited to, an RNAi agent that includes one or more 5'-cyclo-phosphonate modified nucleotides conjugated to delivery polymer to form an RNAi trigger-delivery polymer conjugate. In some embodiments, the delivery polymer is a membrane active polyamine. In some embodiments, the delivery polymer is a reversibly modified membrane active polyamine.

In some embodiments, the targeting ligand or targeting group is a galactose cluster, which is attached to an RNAi agent that includes one or more 5'-cyclo-phosphonate modified nucleotides. In some embodiments, an RNAi agent as described herein is linked to a galactose cluster. As used herein, a galactose cluster comprises a molecule having two to four terminal galactose derivatives. As used herein, the term galactose derivative includes both galactose and derivatives of galactose having affinity for the asialoglycoprotein receptor equal to or greater than that of galactose. A terminal galactose derivative is typically attached to a molecule through its C-1 carbon. In some embodiments, a galactose cluster has three terminal galactosamines or galactosamine derivatives (such as N-acetyl-galactosamine) each having affinity for the asialoglycoprotein receptor. In some embodiments, a galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, Cell, 1980, 22, 611-620; Connolly et al., J. Biol. Chem. 1982, 257, 939-945).

In some embodiments, a galactose cluster contains three galactose derivatives each linked to a central branch point. In some embodiments, a galactose cluster contains four galactose derivatives each linked to a central branch point. The galactose derivatives are attached to the central branch point through the C-1 carbons of the saccharides. In some embodiments, a galactose derivative is linked to the branch point via a linker or spacer.

In some embodiments, a galactose derivative comprises an N-acetyl-galactosamine (GalNAc or NAG). Other saccharides having affinity for the asialoglycoprotein receptor are selected from the list comprising: galactose, galactosamine, N-formyl-galactosamine, N-propionyl-galactosamine, N-n-butanoylgalactosamine, and N-iso-butanoyl-galactosamine. The affinities of numerous galactose derivatives for the asialoglycoprotein receptor have been studied (see for example: Iobst, S. T. and Drickamer, K. *J. B. C.* 1996, 271, 6686) or are readily determined using methods well known and commonly used in the art.

Known targeting ligands suitable for targeting RNAi agents that include 5'-cyclo-phosphonate modified nucleotides are known in the art, for example, in U.S. patent application Ser. Nos. 14/452,626, 15/452,324, 15/452,423 and 62/415,752, the entire contents of which are incorporated herein in their entirety.

Pharmaceutical Compositions and Formulations

The oligomeric compounds, such as RNAi agents, that include 5'-cyclo-phosphonate modified nucleotides disclosed herein, can be used to treat a subject (e.g., a human or animal, e.g., a mammal, such as an ape, monkey, pig, sheep, goat, cow, horse, dog, cat, rabbit, rat, or mouse) having a disease or disorder that would benefit from administration of the compound. In some embodiments, at least one of the described RNAi agents comprising 5'-cyclo-phosphonate modified nucleotides is used in the preparation of a pharmaceutical composition (i.e., medicament) for treatment of a subject that would benefit from reduction or inhibition in gene expression. These pharmaceutical compositions are useful in the inhibition of the expression of the gene in a cell, a tissue, or an organism. In some embodiments, the described pharmaceutical compositions are used to treat a subject having a disease or disorder that would benefit from reduction or inhibition of gene expression.

In some embodiments, the RNAi agents that include 5'-cyclo-phosphonate modified nucleotide(s) can be used to treat a subject (e.g., a human) having a disease or disorder that would benefit from reduction or inhibition in expression of the target mRNA. The subject is administered a therapeutically effective amount of any one or more RNAi agents. The subject can be a human, patient, or human patient. The subject may be an adult, adolescent, child, or infant. The described pharmaceutical compositions including a targeting ligand linked to an expression-inhibiting oligomeric compound can be used to provide methods for the therapeutic treatment of diseases. Such methods include administration of a pharmaceutical composition described herein to a human being or animal.

Accordingly, in some embodiments, the pharmaceutical compositions described herein may comprise one or more pharmaceutically acceptable excipients. In some embodiments, the pharmaceutical compositions described herein can be formulated for administration to a subject.

As used herein, a pharmaceutical composition or medicament comprises a pharmacologically effective amount of at least one of the RNAi agents and/or RNAi agent-conjugates described herein and one or more pharmaceutically acceptable excipients. Pharmaceutically acceptable excipients (excipients) are substances other than the Active Pharmaceutical ingredient (API, therapeutic product, e.g., RNAi agent or RNAi trigger) that have been appropriately evaluated for safety and are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance one or more of the overall safety, effectiveness, or delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

A pharmaceutical composition can contain other additional components commonly found in pharmaceutical compositions. Such additional components include, but are not limited to: anti-pruritics, astringents, local anesthetics, anti-inflammatory agents, or antihistamines (e.g., diphenhydramine, doxylamine, acrivastine, or cetirizine). It is also envisioned that cells, tissues or isolated organs that express or comprise the herein defined RNAi triggers comprising a 5'-cyclo-phosphonate modified nucleotide may be used as "pharmaceutical compositions". As used herein, "pharmacologically effective amount," "therapeutically effective amount," or simply "effective amount" refers to that amount of an RNAi agent that produces the intended pharmacological, therapeutic or preventive result.

In some embodiments, a described RNAi trigger is combined with one or more additional therapeutics or treatments including, but not limited to: a second RNAi trigger or other RNAi agent, a small molecule drug, an antibody, an antibody fragment, and/or a vaccine.

The described RNAi triggers comprising a 5'-cyclo-phosphonate modified nucleotide and pharmaceutical compositions comprising the RNAi triggers disclosed herein may be packaged or included in a kit, container, pack, or dispenser.

The RNAi triggers and pharmaceutical compositions comprising said RNAi triggers may be packaged in pre-filled syringes or vials.

Cells, tissues, and non-human organisms that include at least one of the RNAi triggers comprising a 5'-cyclo-phosphonate modified nucleotide described herein is contemplated. The cell, tissue, or non-human organism is made by delivering the RNAi trigger to the cell, tissue, or non-human organism by any means available in the art. In some embodiments, the cell is a mammalian cell, including, but not limited to, a human cell. The cell, tissue, or non-human organisms are useful for research or as research tools (e.g., drug testing or diagnoses).

In some embodiments, the RNAi agents comprising a 5'-cyclo-phosphonate modified nucleotide described herein are used to treat a subject having a disease or disorder that would benefit from reduction or inhibition of expression of the targeted gene. In some embodiments, the described RNAi agents are used to treat or prevent at least one symptom in a subject having a disease or disorder that would benefit from reduction or inhibition in expression of the targeted gene. The subject is administered a therapeutically effective amount of any one or more of the RNAi agents described herein, thereby treating the symptom.

In some embodiments, the RNAi agents comprising a 5'-cyclo-phosphonate modified nucleotide are used to treat or manage a clinical presentation wherein a subject in need of such treatment, prevention or management, is administered a therapeutically or prophylactically effective amount of one or more of the RNAi agents described herein. In some embodiments, the method comprises administering a composition comprising an RNAi trigger molecule described herein to a mammal, e.g., human, to be treated.

In some embodiments, an RNAi trigger comprising a 5'-cyclo-phosphonate modified nucleotide can be used to inhibit expression of the targeted gene in a cell, group of cells, or a tissue in a subject. In some embodiments, an RNAi trigger can be used to formulate a composition for inhibiting expression of the targeted gene in a cell, group of cells, or a tissue, e.g., in a subject. In some embodiments, a therapeutically effective amount of one type (or several different types) of RNAi agents as described herein is administered to a subject, thereby inhibiting expression of the targeted gene in the subject (e.g., an amount effective to inhibit expression of the targeted gene in the subject).

In some embodiments, the gene expression level and/or mRNA level of a target in a subject to whom a described RNAi trigger comprising a 5'-cyclo-phosphonate modified nucleotide is administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to administration or to a subject not receiving the RNAi trigger. The gene expression level and/or mRNA level in the subject may be reduced in a cell, group of cells, and/or tissue of the subject. In some embodiments, the protein level in a subject to whom a described RNAi trigger comprising a 5'-cyclo-phosphonate modified nucleotide has been administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to being administered the RNAi trigger or to a subject not receiving the RNAi trigger. The protein level in the subject may be reduced in a cell, group of cells, tissue, blood, and/or other fluid of the subject. A reduction in gene expression, mRNA, or protein levels can be assessed by any methods known in the art. Reduction or decrease in mRNA level and/or protein level are collectively referred to herein as inhibiting, decreasing or reducing the expression of the targeted gene or target mRNA.

The route of administration is the path by which an RNAi trigger comprising a 5'-cyclo-phosphonate modified nucleotide is brought into contact with the body. In general, methods of administering drugs and nucleic acids for treatment of a subject are well known in the art and can be applied to administration of the compositions described herein. The compounds described herein can be administered via any suitable route in a preparation appropriately tailored to the particular route. Thus, the compounds described herein can be administered by injection, for example, intravenously, intramuscularly, intracutaneously, subcutaneously, or intraperitoneally In some embodiments, the RNAi trigger molecules or compositions described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with an RNAi trigger comprising a 5'-cyclo-phosphonate modified nucleotide described herein. For example, delivery can be by local administration, (e.g., direct injection, implantation, or topical administering), systemic administration, or subcutaneous, intravenous, oral, intraperitoneal, or parenteral routes, including intracranial (e.g., intraventricular, intraparenchymal and intrathecal), intramuscular, transdermal, airway (i.e., aerosol), nasal, rectal, or topical (including buccal and sublingual) administration, In certain embodiments, the compositions are administered by subcutaneous or intravenous infusion or injection.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 3 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

For treatment of disease or for formation of a medicament or composition for treatment of a disease, the pharmaceutical compositions described herein including an expression-inhibiting oligomeric compound, such as an RNAi agent, including one or more 5'-cyclo-phosphonate modified nucleotides, can be combined with an excipient or with a second therapeutic agent or treatment including, but not limited to: a second or other expression-inhibiting oligomeric compound, a small molecule drug, an antibody, an antibody fragment, and/or a vaccine.

The described RNAi agents that include one or more 5'-cyclo-phosphonate modified nucleotides, when added to pharmaceutically acceptable excipients or adjuvants, can be packaged into kits, containers, packs, or dispensers. The pharmaceutical compositions described herein may be packaged in pre-filled syringes or vials.

The above provided embodiments and items are now illustrated with the following, non-limiting examples.

EXAMPLES

The following examples are not limiting and are intended to illustrate certain embodiments disclosed herein.

Some of the abbreviations used in the following experimental details of the synthesis of the examples are defined below: h or hr=hour(s); min=minute(s); mol=mole(s); mmol=millimole(s); M=molar; µM=micromolar; g=gram (s); µg=microgram(s); rt or RT=room temperature; L=liter (s); mL=milliliter(s); wt=weight; $Et_2O$=diethyl ether; THF=tetrahydrofuran; DMSO=dimethyl sulfoxide; EtOAc=ethyl acetate; Et3N or TEA=triethylamine; i-$Pr_2$NEt or DIPEA or DIEA=diisopropylethylamine; $CH_2Cl_2$ or DCM=methylene chloride; $CHCl_3$=chloroform; $CDCl_3$=deuterated chloroform; $CCl_4$=carbon tetrachloride; MeOH=methanol; EtOH=ethanol; DMF=dimethylformamide; BOC=t-butoxycarbonyl; CBZ=benzyloxycarbonyl; TBS=t-butyldimethylsilyl; TBSCl or TBDMSCl=t-butyldimethylsilyl chloride; TFA=trifluoroacetic acid; DMAP=4-dimethylaminopyridine; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; HCl=hydrogen chloride or hydrochloric acid; NMM=N-methylmorpholine; $H_2$=hydrogen gas; KF=potassium fluoride; EDC-HCl=N-(3-Dimethylaminopropyl)-N'-ethylcarbodiimide hydrochloride; MTBE=methyl-tert-butyl ether; MeOH=methanol; Ar=argon; $N_2$=nitrogen; $SiO_2$=silica; $R_T$=retention time.

Additionally, examples of RNAi agents suitable for use with the 5'-cyclo-phosphonate modified nucleotides disclosed herein are set forth in various Tables in the Examples that follow.

The following notations are used to indicate modified nucleotides for sequences set forth in the Tables disclosed herein. As the person of ordinary skill in the art would readily understand, that when present in an oligonucleotide, the monomers are mutually linked by 5'-3'-phosphodiester bonds unless otherwise indicated:

N=2'-OH (unmodified) ribonucleotide (capital letter without for d indication)
n=2'-OMe modified nucleotide
Nf=2'-fluoro modified nucleotide
dN=2'-deoxy nucleotides
$N_{UNA}$=2',3'-seco nucleotide mimics (unlocked nucleobase analogs)
$N_{LNA}$=locked nucleotide
$N_{fANA}$=2'-F-Arabino nucleotide
NM=2'-methoxyethyl nucleotide
X or Ab=abasic ribose
R=ribitol
(invdN)=inverted deoxyribonucleotide (3'-3' linked nucleotide)
(invAb)=inverted abasic nucleotide
(invX)=inverted abasic nucleotide
(invn)=inverted 2'-OMe nucleotide
s=phosphorothioate linked nucleotide
vpdN=vinyl phosphonate deoxyribonucleotide
(3'OMen)=3'-OMe nucleotide
(5Me-Nf)=5'-Me, 2'-fluoro nucleotide
cPrp=cyclopropyl phosphonate The compounds of the present disclosure can be made using synthetic chemical techniques known to those of skill in the art and as described herein.

Example 1. Synthesis of Compound 4 (dimethyl[2-[(2R,3R,4R,5R)-3-([[bis(propan-2-yl)amino](2-cyanoethoxy)phosphanyl]oxy)-4-(2-methoxyethoxy)-5-(5-methyl-2,4-dioxo-1,2,3,4-tetrahydropyrimidin-1-yl)oxolan-2-yl]cyclopropyl]phosphonate)

A. Synthesis of Compound 2 (dimethyl[2-[(2R,3R,4R,5R)-3-[(tert-butyldiphenylsilyl)oxy]-4-(2-methoxyethoxy)-5-(5-methyl-2,4-dioxo-1,2,3,4-tetrahydropyrimidin-1-yl)oxolan-2-yl]cyclopropyl]phosphonate)

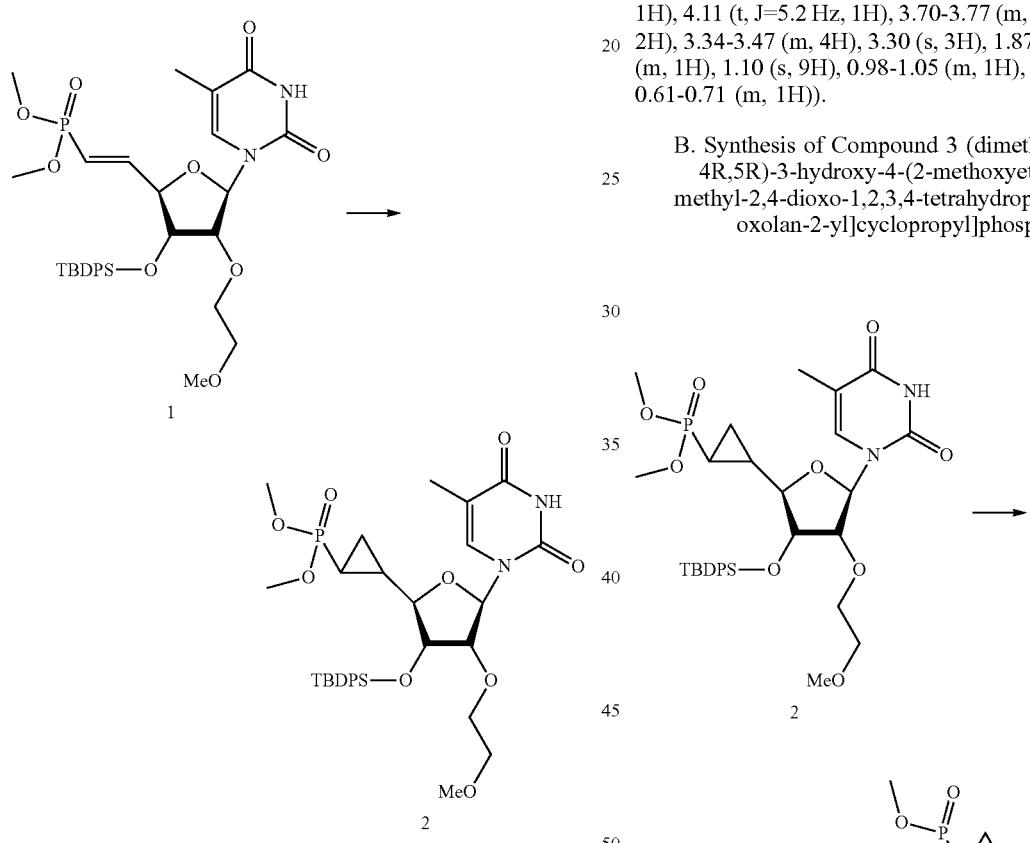

Compound 1 (Dimethyl [(E)-2-[(2R,3R,4R,5R)-3-[(tert-butyldiphenylsilyl)oxy]-4-(2-methoxyethoxy)-5-(5-methyl-2,4-dioxo-1,2,3,4-tetrahydropyrimidin-1-yl)oxolan-2-yl]ethenyl]phosphonate) was synthesized following a procedure similar to that in Whittaker, B. et al., *Tetrahedron Lett.* 49, 6984-6987 (2008) and Abbas, S. et al., *Org. Lett.*, 3(21), 3365-3367 (2001).

Into a 1000-mL 3-necked round-bottom flask purged and maintained with an inert atmosphere of nitrogen, was placed a solution of sodium hydride (8.2 g, 341.67 mmol, 3.00 equiv) in dimethyl sulfoxide (500 mL). This was followed by the addition of a solution of trimethylsulfoxonium iodide (45 g, 204.48 mmol, 3.00 equiv). The resulting solution was stirred for 0.5 h at 25° C. Then, a solution of compound 1 (45 g, 68.31 mmol, 1.00 equiv) in dimethyl sulfoxide (50 mL) was added dropwise with stirring at 25° C. The resulting solution was stirred for 20 h at 25° C. The reaction was then quenched by the addition of 50 mL of saturated aqueous ammonium chloride.

The resulting solution was extracted with 3×1000 mL of dichloromethane and the organic layers were combined. The combined organics were washed with 1×2000 mL of saturated aqueous sodium chloride. The organic layer was dried over anhydrous sodium sulfate, filtered, and concentrated under vacuum. The residue was flash chromatographed over silica gel and eluted with dichloromethane/methanol (100:1-10:1). This resulted in 4.4 g (10%) of compound 2 (dimethyl [2-[(2R,3R,4R,5R)-3-[(tert-butyldiphenylsilyl)oxy]-4-(2-methoxyethoxy)-5-(5-methyl-2,4-dioxo-1,2,3,4-tetrahydropyrimidin-1-yl)oxolan-2-yl]cyclopropyl]phosphonate) as a white solid. (H-NMR: (CDCl$_3$, 400 MHz, ppm): δ 8.55 (s, 1H), 7.71 (t, J=6.4 Hz, 2H), 7.66 (d, J=6.8 Hz, 2H), 7.38-7.64 (m, 6H), 7.03 (s, 1H), 5.86 (d, 3.6 Hz, 1H), 4.11 (t, J=5.2 Hz, 1H), 3.70-3.77 (m, 6H), 3.55-3.61 (m, 2H), 3.34-3.47 (m, 4H), 3.30 (s, 3H), 1.87 (s, 3H), 1.40-1.50 (m, 1H), 1.10 (s, 9H), 0.98-1.05 (m, 1H), 0.80-0.90 (m, 1H), 0.61-0.71 (m, 1H)).

B. Synthesis of Compound 3 (dimethyl[2-[(2R,3R,4R,5R)-3-hydroxy-4-(2-methoxyethoxy)-5-(5-methyl-2,4-dioxo-1,2,3,4-tetrahydropyrimidin-1-yl)oxolan-2-yl]cyclopropyl]phosphonate)

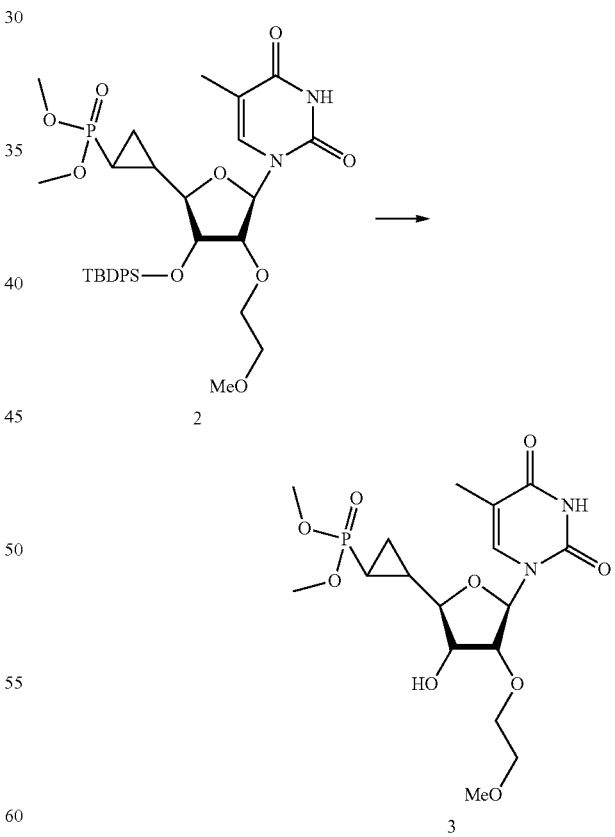

Into a 100-mL 3-necked round-bottom flask purged and maintained with an inert atmosphere of nitrogen, was placed a solution of compound 2 (dimethyl [2-[(2R,3R,4R,5R)-3-[(tert-butyldiphenylsilyl)oxy]-4-(2-methoxyethoxy)-5-(5-methyl-2,4-dioxo-1,2,3,4-tetrahydropyrimidin-1-yl)oxolan- 2-yl]cyclopropyl]phosphonate) (6.0 g, 8.92 mmol, 1.00 equiv) in tetrahydrofuran (60 mL) and triethylamine (4.18 g, 41.31 mmol, 3.00 equiv). This was followed by the addition of triethylamine trihydrofluoride (13.34 g, 82.86 mmol, 6.00 equiv) dropwise with stirring at 0° C. The resulting solution was stirred for 18 h at 25° C. The resulting mixture was concentrated under vacuum and diluted with 60 mL of dichloromethane.

The resulting solution was washed with 100 mL of saturated aqueous sodium bicarbonate and 100 mL of saturated aqueous sodium chloride. The organic solution was dried over sodium sulfate, filtered, and concentrated under vacuum. The residue was flash chromatographed over silica gel and eluted with dichloromethane/methanol (100:1-10:1). This resulted in 3 g (77%) of compound 3 (dimethyl [2-[(2R,3R,4R,5R)-3-hydroxy-4-(2-methoxyethoxy)-5-(5-methyl-2,4-dioxo-1,2,3,4-tetrahydropyrimidin-1-yl)oxolan-2-yl]cyclopropyl]phosphonate) as a white solid. (LC-MS: (ES, m/z): [M+H]$^+$=435. H-NMR: (CDCl$_3$, 300 MHz, ppm): δ 9.53 (s, 1H), 8.28 (s, 1H), 7.17 (s, 1H), 5.75 (s, 1H), 3.95-4.10 (m, 3H), 3.61-3.85 (m, 7H), 3.51-3.58 (m, 2H), 3.41 (s, 4H), 1.93 (s, 3H), 1.67-1.78 (m, 1H), 1.19-1.28 (m, 1H), 1.03-1.05 (m, 2H)).

C. Synthesis of Compound 4 (dimethyl [2-[(2R,3R,4R,5R)-3-([[bis(propan-2-yl)amino](2-cyanoethoxy)phosphanyl]oxy)-4-(2-methoxyethoxy)-5-(5-methyl-2,4-dioxo-1,2,3,4-tetrahydropyrimidin-1-yl)oxolan-2-yl]cyclopropyl]phosphonate)

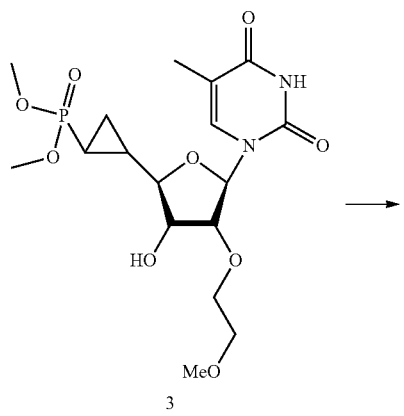

3

Into a 50-mL 3-necked round-bottom flask purged and maintained with an inert atmosphere of nitrogen, was placed a solution of compound 3 (dimethyl [2-[(2R,3R,4R,5R)-3-hydroxy-4-(2-methoxy ethoxy)-5-(5-methyl-2,4-dioxo-1,2,3,4-tetrahy dropyrimidin-1-yl)oxolan-2-yl]cyclopropyl] phosphonate) (2.5 g, 5.76 mmol, 1.00 equiv) in dichloromethane (50 mL) and 4,5-dicyanoimidazole (810 mg, 6.86 mmol, 1.20 equiv). This was followed by the addition of 3-(bis(diisopropylamino)phosphinooxy)propanenitrile (2.25 g, 7.46 mmol, 1.30 equiv) dropwise with stirring at 0° C. The resulting solution was stirred for 3 h at 25° C. The resulting solution was diluted with 25 mL of dichloromethane.

The resulting solution was washed with 2×50 mL of saturated aqueous sodium bicarbonate and 50 mL of saturated aqueous sodium chloride. The organic solution was dried over sodium sulfate, filtered, and concentrated under vacuum. The residue was flash chromatographed over silica gel and eluted with dichloromethane/ethyl acetate (5:1-1:5) (with 0.5% triethylamine). This resulted in 2.1 g (57%) of compound 4 (dimethyl [2-[(2R,3R,4R,5R)-3-([[bis(propan-2-yl)amino](2-cyanoethoxy)phosphanyl]oxy)-4-(2-methoxyethoxy)-5-(5-methyl-2,4-dioxo-1,2,3,4-tetrahydropyrimidin-1-yl)oxolan-2-yl]cyclopropyl]phosphonate) as a white solid. (LC-MS: (ES, m/z): [M+H]$^+$=635. H-NMR: (CD$_3$COCD$_3$, 400 MHz, ppm): δ 10.11 (s, 1H), 7.55-7.58 (m, 1H), 5.94-5.99 (m, 1H), 4.42-4.48 (m, 2H), 3.77-3.86 (m, 3H), 3.69-3.76 (m, 9H), 3.51-3.56 (m, 3H), 3.30 (d, J=2.8 Hz, 3H), 2.81-2.86 (m, 2H), 1.86 (s, 3H), 1.60-1.80 (m, 1H), 1.21-1.27 (m, 12H), 1.04-1.09 (m, 3H). P-NMR: (CD$_3$COCD$_3$, 161 MHz, ppm): δ 149.67, 149.51, 149.21, 31.59, 31.55, 31.41, 31.29.)

Compound 4, above, is a phosphoramidite compound that can be used to add a 5'-cyclopropyl phosphonate-2'-MOE modified nucleotide to form the terminus of a double-stranded RNAi agent and/or a single-stranded antisense oligonucleotide. As a general matter, a similar synthetic process may be used to make phosphoramidites that can be used for adding the 5'cyclo-phosphonate modified nucleotides disclosed herein to form the terminus of the disclosed double-stranded RNAi agents and/or single-stranded antisense oligonucleotides. For example, the person of ordinary skill in the art would appreciate and understand that compound 1 in Example 1 could be synthesized with a different group at the 2' position, such as a 2'-F, 2'-H, or 2'-O-methyl group. Similarly, as a non-limiting example, the person of ordinary skill in the art would appreciate that different heterocyclic base moieties (e.g., uracil, cytosine, guanine, 5-methycytosine, etc.) can be used instead of thymine, as shown in Example 1.

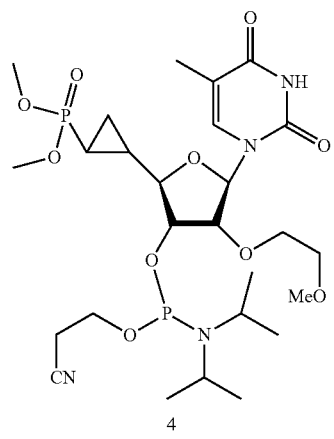

4

Example 2. Synthesis of Compound 15 (2-cyano-ethyl((2R,3R, 4R, 5R)-2-(2-(diethoxyphosphoryl)cyclopropyl)-5-(2,4-dioxo-3,4-dihydropyrimidin-1(2H)-yl)-4-methoxytetrahydrofuran-3-yl) diisopropylphosphoramidite)

A. Synthesis of Compound 6 (1-((2R,3R,4R,5R)-5-((bis(4-methoxyphenyl)(phenyl)methoxy)methyl)-4-hydroxy-3-methoxytetrahydrofuran-2-yl)pyrimidine-2,4(1H,3H)-dione)

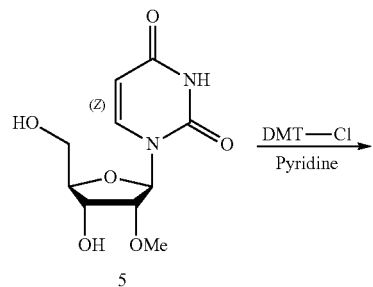

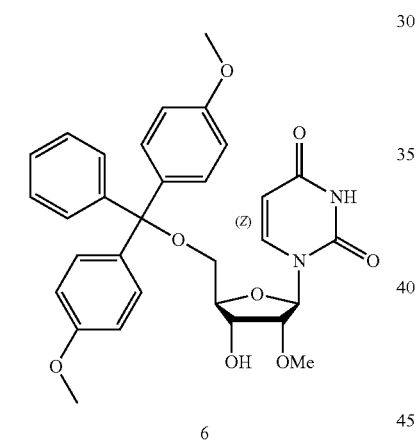

Compound 5 was purchased through commercially available channels. To a solution of compound 5 (200 g, 775 mmol) in pyridine (1.5 L) was added DMT-Cl (276 g, 813 mol). The reaction mixture was stirred at 25° C. for 8 h under $N_2$ atmosphere. TLC (Petroleum ether/Ethyl acetate=1/1, Rf=0.2) showed the reaction was complete. The solvent was removed under reduced pressure. The residue was diluted with EtOAc (4 L), washed with water (1 L×2) and brine (1 L), dried over $Na_2SO_4$, filtered and concentrated under reduced pressure. The final residue was purified by column chromatography ($SiO_2$, Petroleum ether/Ethyl acetate=5:1 to Ethyl acetate) to get compound 6 (448 g, contained EtOAc) as a light yellow gum. ($^1$H NMR: 400 MHz $CDCl_3$. 9.01 (br s, 1H), 8.05 (d, J=8.0 Hz, 1H), 7.36-7.42 (m, 2H), 7.27-7.34 (m, 6H), 7.22-7.27 (m, 1H), 6.81-6.89 (m, 4H), 5.98 (d, J=1.3 Hz, 1H), 5.28 (dd, J=1.9, 8.2 Hz, 1H), 4.48 (dt, J=5.3, 8.5 Hz, 1H), 4.00 (br d, J=8.0 Hz, 1H), 3.81 (d, J=0.8 Hz, 7H), 3.65 (s, 3H), 3.50-3.61 (m, 2H), 2.64 (br d, J=9.0 Hz, 1H)).

B. Synthesis of Compound 7 (1-((2R,3R,4R,5R)-5-((bis(4-methoxyphenyl)(phenyl)methoxy)methyl)-4-((tert-butyldimethylsilyl)oxy)-3-methoxytetrahydrofuran-2-yl)pyrimidine-2,4(1H,3H)-dione)

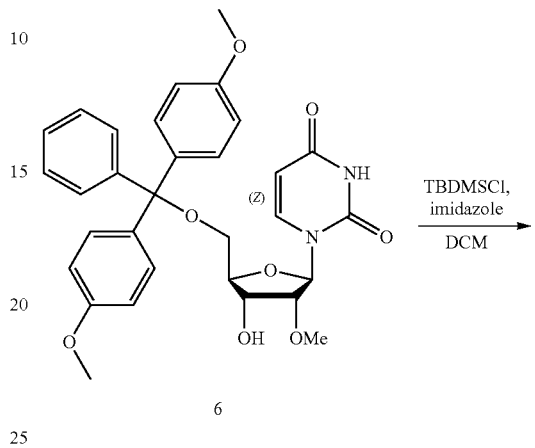

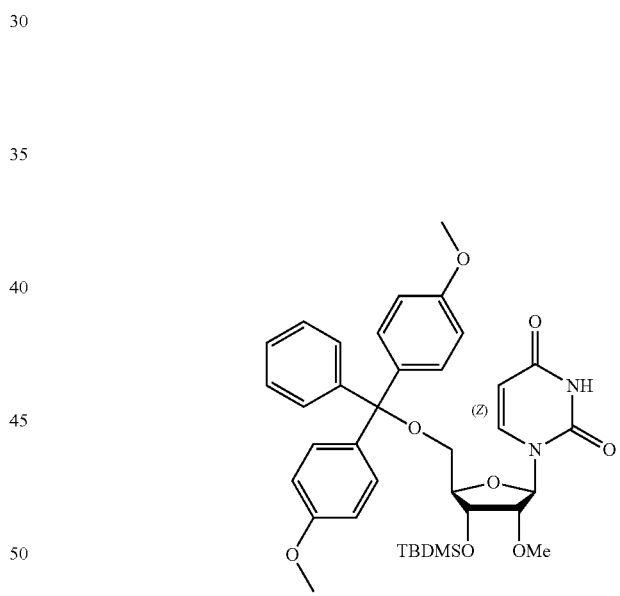

To a solution of compound 6 (448 g, 799 mmol) in DCM (2.8 L) was added imidazole (163 g, 2.4 mol) and TBSCl (241 g, 1.6 mol). The reaction mixture was stirred at 25° C. for 8 h. TLC (Petroleum ether/Ethyl acetate=1/1, Rf=0.8) showed the reaction was complete. The resulting mixture was diluted with water (4.5 L) and extracted with DCM (5 L×3). The combined organic layers were washed with brine (5 L), dried over $Na_2SO_4$, filtered and concentrated under reduced pressure to get compound 7 (620 g, crude) as a colorless gum. The crude product was used to the next step without further purification.

C. Synthesis of Compound 8 (1-((2R,3R,4R,5R)-4-((tert-butyldimethylsilyl)oxy)-5-(hydroxymethyl)-3-methoxytetrahydrofuran-2-yl)pyrimidine-2,4(1H,3H)-dione)

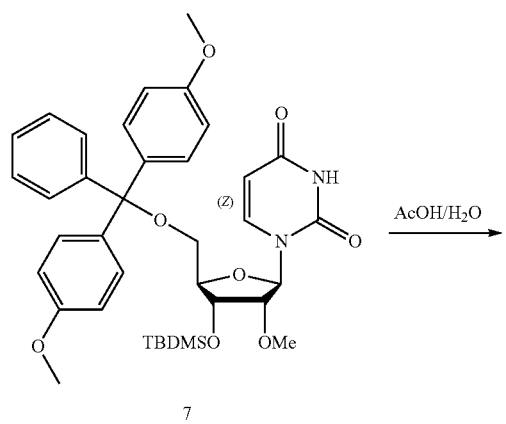

A mixture of compound 7 (620 g, 919 mmol) and AcOH (4 L) in H$_2$O (1 L) was degassed and purged with N$_2$ three times, and then the mixture was stirred at 25° C. for 16 h under N$_2$ atmosphere. TLC (Petroleum ether/Ethyl acetate=1/1, Rf=0.2) showed the reaction was complete. The reaction mixture was quenched by addition MeOH (50 mL) and Et$_3$SiH (25 mL). To the resulting mixture was added NaHCO$_3$ until the pH=7~8, and then extracted with EtOAc (5 L×3). The combined organic layer was washed with brine (5 L), dried over anhydrous Na$_2$SO$_4$, filtered concentrated under reduced pressure. The residue was purified by column chromatography (SiO$_2$, Petroleum ether/Ethyl acetate=5:1 to 1:1) to get compound 8 (296 g, 87% yield) as a white solid. ($^1$H NMR: 400 MHz CDCl$_3$. δ 9.27 (s, 1H), 7.72 (d, J=8.0 Hz, 1H), 5.74 (dd, J=1.3, 8.0 Hz, 1H), 5.69 (d, J=4.0 Hz, 1H), 4.36 (t, J=5.3 Hz, 1H), 4.04-4.09 (m, 1H), 3.93-4.03 (m, 2H), 3.75-3.76 (m, 1H), 3.49 (s, 3H), 2.85 (dd, J=3.5, 6.5 Hz, 1H), 0.92 (s, 9H), 0.11 (d, J=5.3 Hz, 6H)).

D. Synthesis of Compound 9 ((2S,3S,4R,5R)-3-((tert-butyldimethylsilyl)oxy)-5-(2,4-dioxo-3,4-dihydropyrimidin-1(2H)-yl)-4-methoxytetrahydrofuran-2-carbaldehyde)

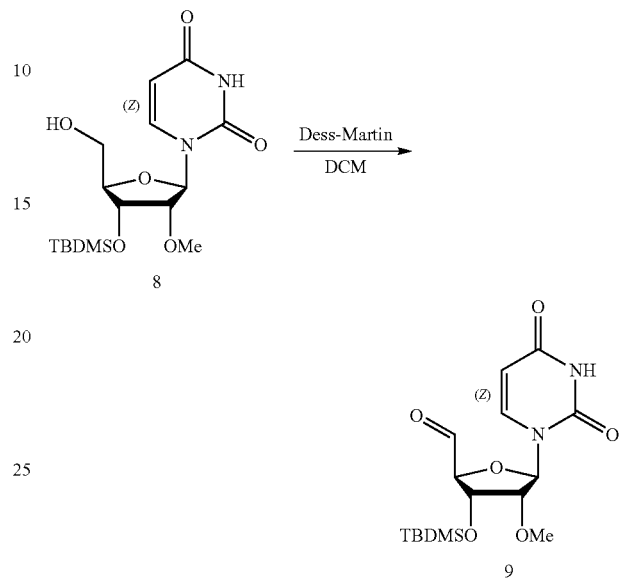

To a solution of compound 8 (60 g, 161 mmol) in DCM (3 L) was added Dess-Martin periodinane (95.7 g, 226 mmol) and NaHCO$_3$ (1.35 g 16.1 mmol) at 0° C. The reaction mixture was stirred at 0° C. for 1 h and then at 25° C. for 3 h. TLC (Petroleum ether/Ethyl acetate=1/1, Rf=0.16) showed the reaction was complete. The resulting mixture was quenched with 4 L solution of saturated Na$_2$S$_2$O$_3$ and saturated NaHCO$_3$ (1:1), and extracted with EtOAc (5 L×3). The combined organic layer was washed with brine (5 L), dried over anhydrous Na$_2$SO$_4$, filtered concentrated under reduced pressure to get compound 9 (48 g, crude) as an orange oil. The crude product was used into the next step without further purification.

E. Synthesis of Compound 10

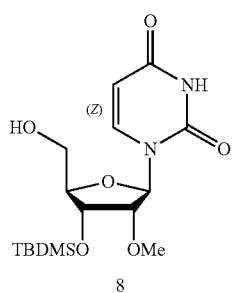

To a slurry of compound 10-1 (231 g, 647 mmol) in THF (2.4 L) was added LiHMDS (1 M in THF, 723 mL). The yellow solution was stirred at 25° C. for 15 min and then cooled to 5° C. The solution was treated with compound 10-2 (110 g, 583 mmol) and allowed to warm to 25° C. where it was held at this temperature. The solution was then cooled to 5° C. and treated with an additional of LiHMDS (1M in THF, 723 mL) and allowed to warm to 2° C. The solution was quenched by addition of H$_2$O (50 mL) at 5° C. and diluted with EtOAc (1.5 L). The organic later was separated, dried over Na$_2$SO$_4$, and concentrated under reduced pressure to get compound 10-3 as an oil. The crude oil was dissolved in THF (2.4 L) and cooled to 5° C. The solution was then treated with NaH (57 g, 1.43 mol, 60% dispersion in mineral oil) and allowed to warm to 25° C. The slurry was stirred for 18 h at 25° C. TLC (Petroleum ether/Ethyl acetate=1/1, Rf=0.3) showed the reaction was complete. The NaH was removed via celite pad and the cake was rinsed with THF (600 mL×2). The filtrate was concentrated to get compound 10 (250 g, crude) as a yellow oil.

F. Synthesis of Compound 11 (O,O-diethyl ((E)-2-((2R,3R,4R,5R)-3-((tert-butyldimethylsilyl)oxy)-5-(2,4-dioxo-3,4-dihydropyrimidin-1(2H)-yl)-4-methoxytetrahydrofuran-2-yl)cyclopropyl) phosphonothioate)

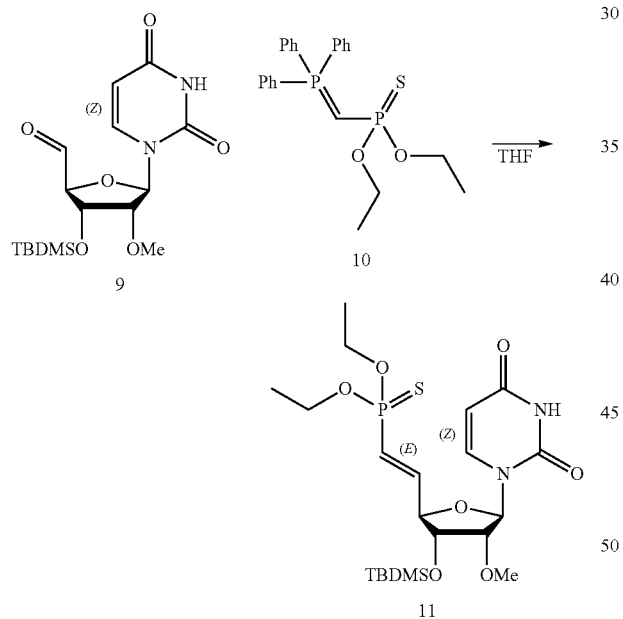

To a solution of compound 9 (165 g, 445 mmol) in THF (1.6 L) was added a solution of compound 10 (250 g, 583 mmol) in THF (0.8 L) drop-wise at 5° C. Then the reaction was allowed to warm to 25° C. and stirred for 1 h. TLC (Petroleum ether/Ethyl acetate=1/1, Rf=0.6) showed the reaction was complete. The reaction mixture was concentrated under reduced pressure. The residue was purified by column chromatography (SiO$_2$, Petroleum ether/Ethyl acetate=10:1 to 1:1) to get compound 11 (89 g, 85% purity; 72 g, 65% purity; 59 g, 48% purity, 65% yield) as a clear oil (the impurity was identified as triphenylphosphine oxide (Ph$_3$P=O)). ($^1$H NMR: 400 MHz CDCl$_3$. δ 8.46 (br s, 1H), 7.30 (d, J=8.3 Hz, 1H), 6.76-6.89 (m, 1H), 6.18-6.30 (m, 1H), 5.85 (d, J=2.0 Hz, 1H), 5.79 (d, J=8.3 Hz, 1H), 4.51-4.59 (m, 1H), 4.07-4.18 (m, 4H), 3.98 (dd, J=5.0, 7.5 Hz, 1H), 3.73 (dd, J=2.4, 5.1 Hz, 1H), 3.54 (s, 3H), 1.33 (dt, J=2.3, 7.0 Hz, 6H), 0.92 (s, 9H), 0.11 (s, 6H)).

G. Synthesis of Compound 12 (O,O-diethyl (2-((2R,3R,4R,5R)-3-((tert-butyldimethylsilyl)oxy)-5-(2,4-dioxo-3,4-dihydropyrimidin-1(2H)-yl)-4-methoxytetrahydrofuran-2-yl)cyclopropyl) phosphonothioate)

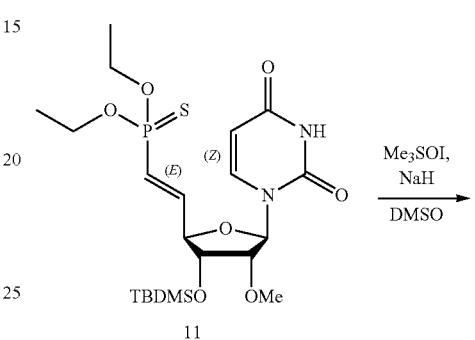

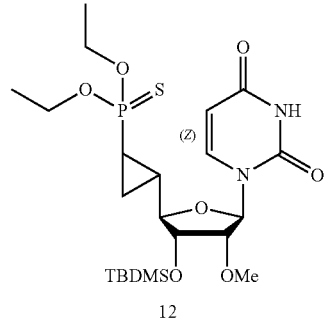

To a solution of Me$_3$SOI (95.9 g, 436 mmol) in DMSO (800 mL) was added sodium hydride (17.4 g, 436 mmol, 60% dispersion in mineral oil) as a THF slurry. The resulting white, foamy slurry was stirred at 25° C. for 15 minutes and the resulting white solution was charged to a flask containing compound 11 (89 g, 85% purity, 145 mmol). The temperature increased from 22° C. to 26° C. and the yellow solution was stirred for 2 hours, and then heated to 50° C. for 2 hours. LCMS showed the reaction was complete. The reaction mixture was cooled to 5° C. and quenched with ice, keeping the internal temperature under 30° C. The product was extracted with ethyl acetate (3 L) and the organic layer was washed with water (5×1 L). The organic layer was dried over Na$_2$SO$_4$, filtered, and concentrated under reduced pressure to get compound 12 (206 g, crude) as a white solid (The impurity was Ph$_3$P=O; the crude product was used into the next step without further purification.

H. Synthesis of Compound 13 (O,O-diethyl(2-((2R,3R,4R,5R)-5-(2,4-dioxo-3,4-dihydropyrimidin-1(2H)-yl)-3-hydroxy-4-methoxytetrahydrofuran-2-yl)cyclopropyl)phosphonothioate)

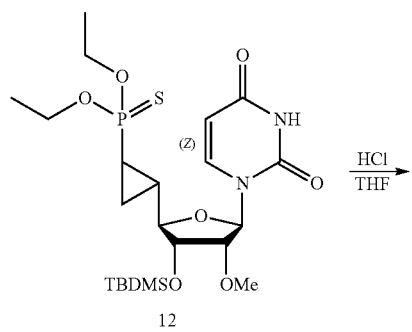

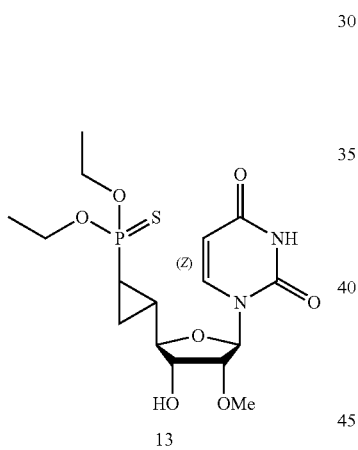

To a stirred solution of compound 12 (206 g, 385 mmol) in THF (1.3 L) was added drop-wise 12M HCl (340 mL, 4.1 mol). The resulting mixture was stirred at 25° C. for 1.5 h. TLC (DCM/Ethyl acetate=1/1, Rf=0.2) showed the reaction was complete. The reaction mixture was cooled with an ice bath and quenched with a saturated solution of sodium bicarbonate until pH=8. The product was extracted with EtOAc (3.9 L×2), and the combined organic layers were then washed with brine (1.3 L). The organic layer was dried over Na$_2$SO$_4$, filtered, and concentrated. The residue was purified by column chromatography (SiO$_2$, DCM/Ethyl acetate=DCM to 1:1) to get compound 13 (76 g, 47% yield) as a white solid. ($^1$H NMR: 400 MHz CDCl$_3$. δ 8.37 (br. s., 1H), 7.41 (d, J=8.0 Hz, 1H), 5.75-5.86 (m, 2H), 4.00-4.18 (m, 5H), 3.79-3.85 (m, 1H), 3.56-3.64 (m, 3H), 3.41-3.53 (m, 1H), 2.65-2.74 (m, 1H), 1.49-1.62 (m, 1H), 1.24-1.34 (m, 8H), 0.97-1.09 (m, 1H)).

I. Synthesis of Compound 14 (Diethyl(2-((2R,3R,4R,5R)-5-(2,4-Dioxo-3,4-Dihydropyrimidin-1(2H)-yl)-3-hydroxy-4-methoxytetrahydrofuran-2-yl)cyclopropyl)phosphonate)

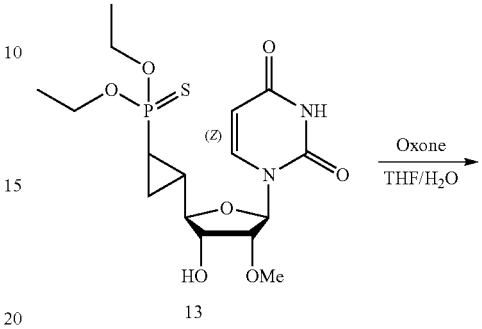

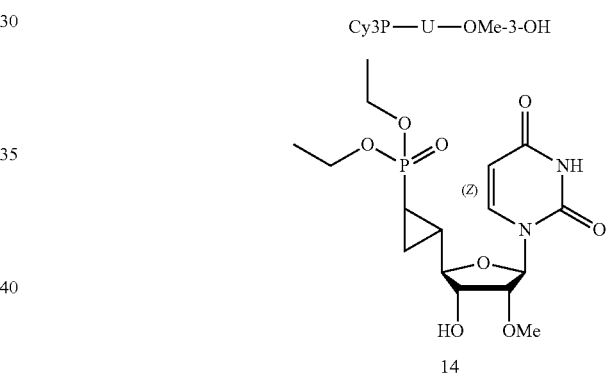

To a solution of compound 13 (76 g, 181 mmol) in 1.4 L THF:H$_2$O (1:1) cooled to 5° C. was added Oxone® (194 g, 316 mmol). The reaction mixture was stirred at 5° C. for 2 h. LCMS showed the reaction was complete. The reaction mixture was diluted with 200 mL H$_2$O and extracted with 2.5 L DCM. The organic layer was collected, and the aqueous layer was further extracted with DCM (2.5 L×4). The organic layers were combined then dried over Na$_2$SO$_4$, filtered, and concentrated. The residue was purified by column chromatography (SiO$_2$, DCM/MeOH=DCM to 10:1) to get compound 14 (Cy3P-U-OMe-3-OH) (40 g, crude) as a white solid. Finally, the crude product was purified by prep-HPLC (Gemini150*4.6 mm (Luna200*25 mm (C18, 10 um, 100 Å)+Gemini150*30 (c18, 5 um, 110 Å), 0.1% TFA/CH3CN/H2O, 20 mL/Min) to get compound 14 (20.02 g, 99% purity, 27% yield) as a clear solid. ($^1$H NMR: 400 MHz CDCl$_3$. δ 9.54 (br. s., 1H), 7.40-7.48 (m, 1H), 5.75-5.89 (m, 2H), 3.98-4.23 (m, 5H), 3.84 (dd, J=2.5, 5.3 Hz, 1H), 3.56-3.64 (m, 3H), 3.40 (td, J=7.9, 16.5 Hz, 1H), 1.58-1.70 (m, 1H), 1.30-1.40 (m, 6H), 1.20-1.29 (m, 1H), 0.92-1.09 (m, 2H)).

J. Synthesis of Compound 15 (2-cyanoethyl((2R, 3R,4R,5R)-2-(2-(diethoxyphosphoryl)cyclopropyl)-5-(2,4-dioxo-3,4-dihydropyrimidin-1(2H)-yl)-4-methoxytetrahydrofuran-3-yl) diisopropylphosphoramidite)

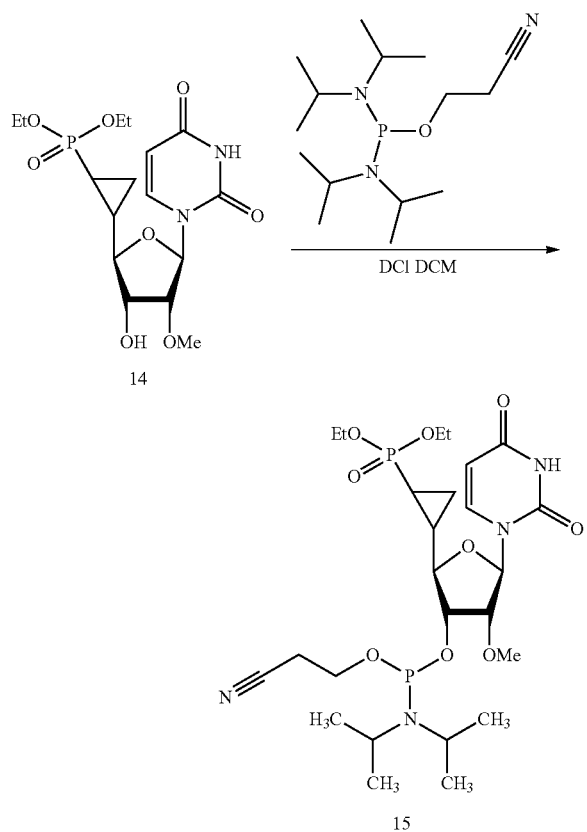

To a solution of compound 14 (463 mg, 1.1 mmol) in DCM (6 mL) was added 4,5-dicyanoimidazole (54 mg, 0.46 mmol) followed by a solution of 2-cyanoethyl N,N,N',N'-tetraisopropylphosphorodiamidite (518 mg, 1.7 mmol, 1.5 eq) in dichlormethane (3 mL). The reaction mixture was stirred overnight. After confirming all starting material was consumed by HPLC, the reaction mixture was concentrated under reduced pressure to a volume of ~2 mL. The crude solution was loaded on to a silica column and purified using an isocratic gradient (DCM: EtOAc: triethylamine: methanol (6:4:0.1:0.05), Rf=0.25). Yield: 421 mg (61%) as a mixture of cyclopropyl and phosphoramidite diastereomers (4 total). ($^1$H NMR: 400 MHz DMSO-d6. δ 11.41 (s, 1H), 7.82-7.72 (m, 1H), 5.73-5.64 (m, 1H), 5.82-5.76 (m, 1H), 4.49-4.18 (m, 2H), 4.11-3.91 (m, 4H), 3.88-3.50 (m, 4H), 3.42-3.32 (m, 4H), 2.79 (m, 2H), 1.73-1.53 (m, 1H), 1.30-1.11 (m, 18H), 1.10-0.79 (m, 3H)).

Compound 15, above, is a phosphoramidite compound that can be used to add a 5'-cyclopropyl phosphonate-2'-O-Me modified nucleotide to form the terminus of a double-stranded RNAi agent and/or a single-stranded antisense oligonucleotide. As a general matter, a similar synthetic process may be used to make phosphoramidites that can be used for adding the 5'cyclo-phosphonate modified nucleotides disclosed herein to form the terminus of the disclosed double-stranded RNAi agents and/or single-stranded antisense oligonucleotides. For example, the person of ordinary skill in the art would appreciate and understand that compound 5 in Example 2 could be synthesized with a different group at the 2' position, such as a 2'-F or 2'-deoxy group. Similarly, as a non-limiting example, the person of ordinary skill in the art would appreciate that different heterocyclic base moieties (e.g., thymine cytosine, guanine, 5-methycytosine, etc.) can be used instead of uracil, as shown in Example 2.

Example 3. RNAi Agent Synthesis

Synthesis of RNAi agents started from individual synthesis of the sense strand and antisense strand. The two complementary strands were first synthesized on solid support resin, then subjected to cleavage and deprotection, followed by purification with either reverse phase or ion exchange chromatography, and finally annealed to form the RNAi agent.

A) Solid phase synthesis. The RNAi agents were synthesized according to phosphoramidite technology on solid phase used in oligonucleotide synthesis. Depending on the scale, a commercially available automated oligosynthesizer was used, such as a MerMade96E® (Bioautomation), a MerMade12® (Bioautomation), or an AKTA Oligopilot (GE). The solid phase synthesis started from the 3' end of the sequence, and phosphoramidite building blocks were sequentially added over each synthetic cycle to grow the oligomer, following the required order. Each synthetic cycle included four chemical steps: 1) De-blocking or detritylation; 2) Coupling; 3) Oxidation; 4) Capping. The phosphoramidites were derived from nucleotides, either naturally occurring or chemically modified, or small molecules such as N-acetyl galactosamine targeting ligands. Syntheses were performed on a solid support made of controlled pore glass (CPG, 500 Å or 600 Å, obtained from Prime Synthesis, Aston, Pa., USA). All RNA and 2'-modified RNA phosphoramidites were purchased from Thermo Fisher Scientific (Milwaukee, Wis., USA). Specifically, the following 2'-O-methyl phosphoramidites were used: (5'-O-dimethoxytrityl-N$^6$-(benzoyl)-2'-O-methyl-adenosine-3'-O-(2-cyanoethyl-N,N-diisopropyl-amino) phosphoramidite, 5'-O-dimethoxy-trityl-N$^4$-(acetyl)-2'-O-methyl-cytidine-3'-O-(2-cyanoethyl-N,N-diisopropyl-amino) phosphoramidite, (5'-O-dimethoxytrityl-N$^2$-(isobutyryl)-2'-O-methyl-guanosine-3'-O-(2-cyano-ethyl-N, N-diisopropylamino)phosphoramidite, and 5'-O-dimethoxy-trityl-2'-O-methyl-uridine-3'-O-(2-cyanoethyl-N,N-diisopropylamino)phosphoramidite. The 2'-deoxy-2'-fluoro-phosphoramidites carried the same protecting groups as the 2'-O-methyl RNA amidites. Targeting ligand containing phosphoramidites were dissolved in anhydrous dichloromethane or anhydrous acetonitrile (50 mM), while all other amidites were dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, Mass., USA) in anhydrous Acetonitrile was employed.

B) Hydrolysis of 5'-Cyclopropyl Phosphonate Modified Nucleotides.

The hydrolysis of 5'-cyclopropyl phosphonate support-bound oligonucleotides was carried out on the AKTA Oligopilot (GE) synthesizer. A mixture of trimethylsilyl iodide/pyridine/acetonitrile (1:13:40 v/v) was passed through the reactor column at a flow rate of 2 mL/min for 30 minutes to 90 minutes depending on the reaction scale. The column was then washed with acetonitrile and removed from the synthesizer and the support-bound oligonucleotide was transferred into a funnel and washed with acetonitrile/water (1:1 v/v).

C) Cleavage and deprotection of support bound oligonucleotide. After finalization of the solid phase synthesis and deprotection of the 5'-cyclopropylphosphonate support-bound oligonucleotides, the dried solid support was treated with a 1:1 volume solution of 40 wt % aqueous methyl amine in water and 28 wt % aqueous ammonium hydroxide solution (Aldrich) for two hours at 30° C. The solution was evaporated and the solid residue was reconstituted in water (see below).

D) Purification. Crude oligonucleotides were purified by reverse phase HPLC or ion exchange chromatography. Product-containing fractions were pooled, and purity and identity of each single strand was confirmed by LCMS. The concentration and yields of oligonucleotides were assessed by UV (260 nm) with a theoretically derived extinction coefficient.

E) Annealing. Complementary strands were mixed by combining equimolar solutions of sense strands and antisense strands. These solutions were either left to stand at ambient temperature, or placed into a thermomixer at 70° C., heated to 95° C., held at 95° C. for 5 min, and cooled to room temperature slowly. Some RNAi agents were lyophilized and stored at −15 to −25° C. Duplex concentration was determined by measuring the solution absorbance at 260 nm on a UV-Vis spectrometer. Unless otherwise stated, all conversion factor was 0.037 mg/(mL·cm). For some experiments, a conversion factor was calculated from an experimentally determined extinction coefficient.

Example 4. Exemplary RNAi Agent Sequences Comprising 5'-Cyclo-Phosphonate Modified Nucleotides Targeting LP(a) (Human Apo(a) Gene)

The following sequences listed in Table 1, below, are exemplary only. The 5'-cyclo-phosphonate modified nucleotides disclosed herein can be incorporated into any RNAi agent or single-stranded antisense oligonucleotide targeting any gene.

TABLE 1

Modified RNAi agent sequences targeting LP(a) (human Apo(a) gene)

| Duplex ID | Sequence Identifier | SEQ ID NO: | Sequence Information (5' to 3') |
|---|---|---|---|
| AD03158 | Sense Strand: AM-05324-SS | 1 | (NAG)(invAb)GfcCfcCfu UfAfUfuGfuUfaUfaCfgau su(invAb) |
| | Antisense Strand: AM-05478-AS | 2 | usCfsgsUfaUfaAfCfAfau aAfgGfgGfcusu |
| AD03541 | Sense Strand: AM-05324-SS | 3 | (NAG)(invAb)GfcCfcCfu UfAfUfuGfuUfaUfaCfgau su(invAb) |
| | Antisense Strand: AM-05641-AS | 4 | cPrpTMsCfsgsUfaUfaAfC fAfauaAfgGfgGfcusu |

The RNAi agents in Table 1, above, were prepared according to the synthesis described in Example 3. As used in the Tables herein, 2'-O-methyl nucleotides are represented as a lower case letter 'n' in a nucleotide sequence; 2'-deoxy-2'-fluoro nucleotides are represented as Nf; 2'-deoxy nucleotides are represented herein as dN; 2'-methoxyethyl (2'-O-2-methoxylethyl) nucleotides are represented herein as NM; 3' to 3' linkages (inverted) nucleotides are represented herein as invdN, invN, invn, invX, or invAb; 5'-cyclopropyl phosphonates are represented herein as cPrp before a nucleotide, as in cPrpN, cPrpn, cPrpNf, cPrpdN, or cPrpNM; abasic nucleotides (represented herein as Ab); n-acetyl-galactosamine cluster targeting ligands are represented as NAG; and 5'-phosphorothioate groups are represented herein as a lower case 's' before a nucleotide, as in sN, sn, sNf, or sdN).

Example 5. In Vivo Analysis of RNAi Agents Targeting LP(a) (Human Apo(a) Gene) in Transgenic Mice A) To evaluate the efficacy of LP(a) RNAi agents in vivo, apo(a) transgenic mice were used (Frazer K A et al., Nature Genetics 9:424-431 (1995)). This mouse expresses human apo(a) from a YAC containing the full LPA gene (encoding apo(a) protein) with additional sequences both 5' and 3'. RNAi agents conjugated to an N-acetyl-galactosamine targeting ligand linked to the 5' terminal end of the sense strand were administered to mice on day 1. Each mouse received a single subcutaneous (SC) injection of either saline (n=4) or the respective treatment group (n=3 for all treatment groups). Control serum (pre-treatment) samples were taken from the mice pre-injection on day −1. Post injection serum samples were taken from the mice on days 8, 15, 22, 29, and 36.

B) Apo(a) protein levels. Human apo(a) protein levels in serum were monitored by assaying serum from the mice using an ELISA for apo(a) (Abcam). For normalization, apo(a) levels for each animal at a time point was divided by the pre-treatment level of expression in that animal (in this case at day −1) to determine the ratio of expression "normalized to day −1". Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group, as shown in Tables 2.

TABLE 2

Apo(a) Knockdown (KD) in Transgenic Mice with Single Dose of 0.5 mg/kg RNAi Agent Administered at Day 1.

| RNAi Agent | Day 8 Apo(a) KD % | Day 15 Apo(a) KD % | Day 22 Apo(a) KD % | Day 29 Apo(a) KD % | Day 36 Apo(a) KD % |
|---|---|---|---|---|---|
| AD03158 | 56% | 78% | 82% | 66% | 41% |
| AD03158 (Std. Dev.) | 0.249 | 0.154 | 0.067 | 0.127 | 0.292 |
| AD03541 (with 5'-cyclopropylphosphonate modified nucleotide) | 90% | 90% | 85% | 84% | 58% |
| AD03541 (Std. Dev.) | 0.064 | 0.063 | 0.013 | 0.006 | 0.044 |

As shown in Table 2, above, nadir for AD03541 was reached on day 8, while nadir was not reached until day 22 for AD03158. Further, AD03541 achieved greater knockdown across all time points.

Example 6. Factor 12 Knockdown (KD) in Cynomolgus Monkeys

RNAi agents having sequences directed to Factor 12 (F12) and linked to an N-acetyl-galactosamine targeting ligand at the 5' terminal end of the sense strand, were synthesized and combined in a pharmaceutically acceptable buffer as known in the art for subcutaneous (SC) injection.

On day 1, cynomolgus macaque (Macaca fascicularis) primates were injected subcutaneously with 3 mg/kg of either F12 RNAi agent AD04254 or AD04443. Two (2) monkeys were dosed with treatment group AD04443, and three (3) monkeys were dosed with treatment group AD04254.

TABLE 3

F12 RNAi Agents of Example 6.

| Duplex ID | Sequence Identifier | SEQ ID NO: | Sequence Information (5' to 3') |
|---|---|---|---|
| AD04254 | Sense Strand: AM-05324-SS | 5 | (NAG)sascucaauaAfAfG fugcuuugaaas(invAb) |
| | Antisense Strand: AM-05478-AS | 6 | usUfsusCfaAfaGfcAfcU fuUfaUfuGfaGfsu |
| AD04443 | Sense Strand: AM-05324-SS | 7 | (NAG)sascucaauaAfAfG fugcuuugaaas(invAb) |
| | Antisense Strand: AM-05641-AS | 8 | cPrpusUfsusCfaAfaGfc AfcUfuUfaUfuGfaGfsu |

As shown in Table 3, above, AD04254 and AD04443 are comprised of the identical sense strands, with the only differences in the RNAi agents being that the 5' terminal end of the antisense strand comprises either a 2'-O-methyl u modified nucleotide (AD04254), or a 5'-cyclopropyl phosphonate modified nucleotide that also includes 2'-O-methyl u modification (AD04443).

Serum samples from the treated cynomolgus monkeys were taken on days −29, −7 and day 1 (pre-dose), and on days 8, 15 and 22, and 29 to monitor knockdown. Knockdown was measured by quantifying circulating cyano F12 protein (cF12) levels in serum by a human F12 ELISA kit (Molecular Innovations). cF12 levels for each animal at a respective time point was divided by the pre-treatment level (average of day −29, day −7, and day 1) of expression in that animal to determine the ratio of expression "normalized to pre-dose".

Average normalized relative expression of cF12 is shown in FIG. 1. As shown in FIG. 1, based on single dose administration, the F12 RNAi agent that included a 5'-cyclopropylphosphonate modified nucleotide of the present invention at the 5' terminal end of the antisense strand of this sequences provided numerically increased potency and slightly faster knockdown as compared to the same F12 RNAi agent that did not include a 5'-cyclopropyl phosphonate modified nucleotide.

Example 7. Factor 12 Knockdown (KD) in Wild Type Mice

F12 double-stranded RNAi agents were prepared that were conjugated at the 5' terminal end of the sense strand to an N-acetyl-galactosamine targeting ligand. Each of the double-stranded RNAi agents were directed to F12 and were combined in a pharmaceutically acceptable buffer as known in the art for subcutaneous (SC) injection.

The F12 RNAi agents (AD04162 and AD04649) were delivered to wild type mice via SC injection. On day 1, a SC injection was administered into the loose skin on the back between the shoulders of 200 µl solution/20 g mouse containing either saline, a 0.5 mg/kg (mpk) dose of one of the RNAi agents in buffered saline, or a 1.0 mg/kg (mpk) dose of one of the RNAi agents in buffered saline. There were four (4) wild type mice per each of the five treatment groups.

TABLE 4

F12 RNAi agents of Example 7.

| Duplex ID | Sequence Identifier | SEQ ID NO: | Sequence Information (5' to 3') |
|---|---|---|---|
| AD04162 | Sense Strand: AM-05321-SS | 9 | (NAG)sasacucaauAfAfA fgugcuuugaas(invAb) |
| | Antisense Strand: AM-05331-AS | 10 | usUfscsAfaAfgCfaCfuU fuAfuUfgAfgUfsu |
| AD04649 | Sense Strand: AM-05321-SS | 11 | (NAG)sasacucaauAfAfA fgugcuuugaas(invAb) |
| | Antisense Strand: AM-05950-AS | 12 | cPrpdUsUfscsAfaAfgCf aCfuUfuAfuUfgAfgUfsu |

As shown in Table 4, above, AD04162 and AD04649 are comprised of identical sense strands, with the only difference between the RNAi agents being that the 5' terminal end of the antisense strand comprises either a 2'-O-methyl uracil modified nucleotide (AD04162), or a 5'-cyclopropyl phosphonate uracil modified nucleotide that has a 2'-deoxy modification (AD04649).

Serum samples from treated mice were taken on days −1 (pre-dose), 8, 15 and 22, and 29 to monitor knockdown. Knockdown was measured by quantifying circulating mouse F12 protein (mF12) levels in serum by an internally developed mF12 alphaLISA® (Perkin Elmer). mF12 levels for each animal at a respective time point was divided by the pre-treatment level of expression in that animal to determine the ratio of expression "normalized to pre-dose". Expression at a specific time point was then normalized to the saline control group by dividing the "normalized to day pre-dose" ratio for an individual animal by the mean "normalized to day pre-dose" ratio of all mice in the saline control group. This resulted in expression for each time point normalized to that in the control group. Experimental error is given as standard deviation, as shown in Table 5:

TABLE 5 mF12 Knockdown (KD) Percentage in Wild Type Mice with Single Dose of RNAi Agent Administered at Day 1.

| RNAi Agent | Day 8 mF12 KD % | Day 15 Apo(a) KD % | Day 22 Apo(a) KD % | Day 29 Apo(a) KD % |
|---|---|---|---|---|
| AD04162 (0.5 mg/kg) | 76.7% | 71.1% | 59.3% | 52.5% |
| (Std. Dev.) | 0.109 | 0.126 | 0.167 | 0.117 |
| AD04162 (1.0 mg/kg) | 90.2% | 82.6% | 73.8% | 65.1% |
| (Std. Dev.) | 0.058 | 0.078 | 0.143 | 0.144 |
| AD04649 (0.5 mg/kg) (with 5'-cyclopropylphosphonate modified nucleotide) | 83.9% | 69.1% | 70.9% | 46.0% |
| (Std. Dev.) | 0.019 | 0.049 | 0.023 | 0.065 |
| AD04649 (1.0 mg/kg) (with 5'-cyclopropylphosphonate modified nucleotide) | 93.1% | 90.0% | 89.9% | 84.0% |
| (Std. Dev.) | 0.013 | 0.037 | 0.058 | 0.172 |

As shown in Table 5, above, these data support that addition of a 5'-cyclo-phosphonate modified nucleotide of the present invention can provide for increased potency for these F12 RNAi agents in wild type mice, particularly at a 1.0 mg/kg dose.

Example 8. HBsAg Reduction in pHBV Model Mice pHBV model mice were used to assess HBV surface antigen (HBsAg) reduction. Six to eight week old female NOD.CB17-Prkdscid/NcrCrl (NOD-SCID) mice were transiently transfected in vivo with MC-HBV1.3 by hydrodynamic tail vein injection (Yang P L et al. "Hydrodynamic injection of viral DNA: a mouse model of acute hepatitis B virus infection," PNAS USA 2002 Vol. 99: p. 13825-13830), administered 30 to 45 days prior to administration of an HBV RNAi agent or control. MC-HBV1.3 is a plasmid-derived minicircle that contains the same terminally redundant human hepatitis B virus sequence HBV1.3 as in the HBV1.3.32 transgenic mice (GenBank accession #V01460) (Guidotti L G et al., "High-level hepatitis B virus replication in transgenic mice," J Virol 1995 Vol. 69, p 6158-6169.). 5 µg MC-HBV1.3 in Ringer's Solution in a total volume of 10% of the animal's body weight was injected into mice via tail vein to create pHBV model of chronic HBV infection. The solution was injected through a 27-gauge needle in 5-7 seconds as previously described (Zhang G et al., "High levels of foreign gene expression in hepatocytes after tail vein injection of naked plasmid DNA." Human Gene Therapy 1999 Vol. 10, p 1735-1737.). At day −1, Hepatitis B surface antigen (HBsAg) HBsAg expression levels in serum were measured by ELISA and the mice were grouped according to average HBsAg expression levels.
  i) Serum collection: Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C.
  ii) Serum Hepatitis B surface antigen (HBsAg) levels: Serum was collected and diluted 10 to 2000-fold in PBS containing 5% nonfat dry milk. Secondary HBsAg standards diluted in the nonfat milk solution were prepared from serum of ICR mice (Harlan Sprague Dawley) that had been transfected with 10 µg HBsAg-expressing plasmid pRc/CMV-HBs (Aldevron, Fargo, N.D.). HBsAg levels were determined with a GS HBsAg EIA 3.0 kit (Bio-Rad Laboratories, Inc., Redmond, Wash.) as described by the manufacturer. Recombinant HBsAg protein, ayw subtype, also diluted in nonfat milk in PBS, was used as a primary standard (Aldevron).

HBsAg expression for each animal was normalized to the control group of mice injected with saline in order to account for the non-treatment related decline in expression of MC-HBV1.3. First, the HBsAg level for each animal at a time point was divided by the pre-treatment level of expression in that animal (Day −1) in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal saline control group.

At day 1, each mouse was administered a single subcutaneous administration of 200 µl containing 2 mg/kg (mpk) of an HBV double-stranded RNAi agent linked to an N-acetyl-galactosamine targeting ligand on the 5' terminal end of the sense strand, or 200 µl of phosphate buffered saline without an HBV RNAi agent to be used as a control. The HBV RNAi agents administered included AD04580 (which included a 5'-cyclopropyl phosphonate uracil modified nucleotide having a 2'-O-methyl modification, located at the 5' terminal end of the antisense strand) and AD04178 (which included a 2'-O-methyl uracil modified nucleotide located at the 5' terminal end of the antisense strand) formulated in phosphate buffered saline. The RNAi agents AD04580 and AD04178 were otherwise identical; the only difference between these two RNAi agents is the inclusion of a 5'-cyclopropyl phosphonate moiety in AD04580 at the 5' terminal end of the antisense strand, while AD04178 had a phosphate group at the 5' terminal end of the antisense strand common to standard nucleotides.

The injections were performed between the skin and muscle (i.e. subcutaneous injections) into the loose skin over the neck and shoulder area. Three (3) mice in each group were tested (n=3). Serum was collected on day 8, day 15, day 22, and day 29, and serum Hepatitis B surface antigen (HBsAg) levels were determined.

Figure 2:
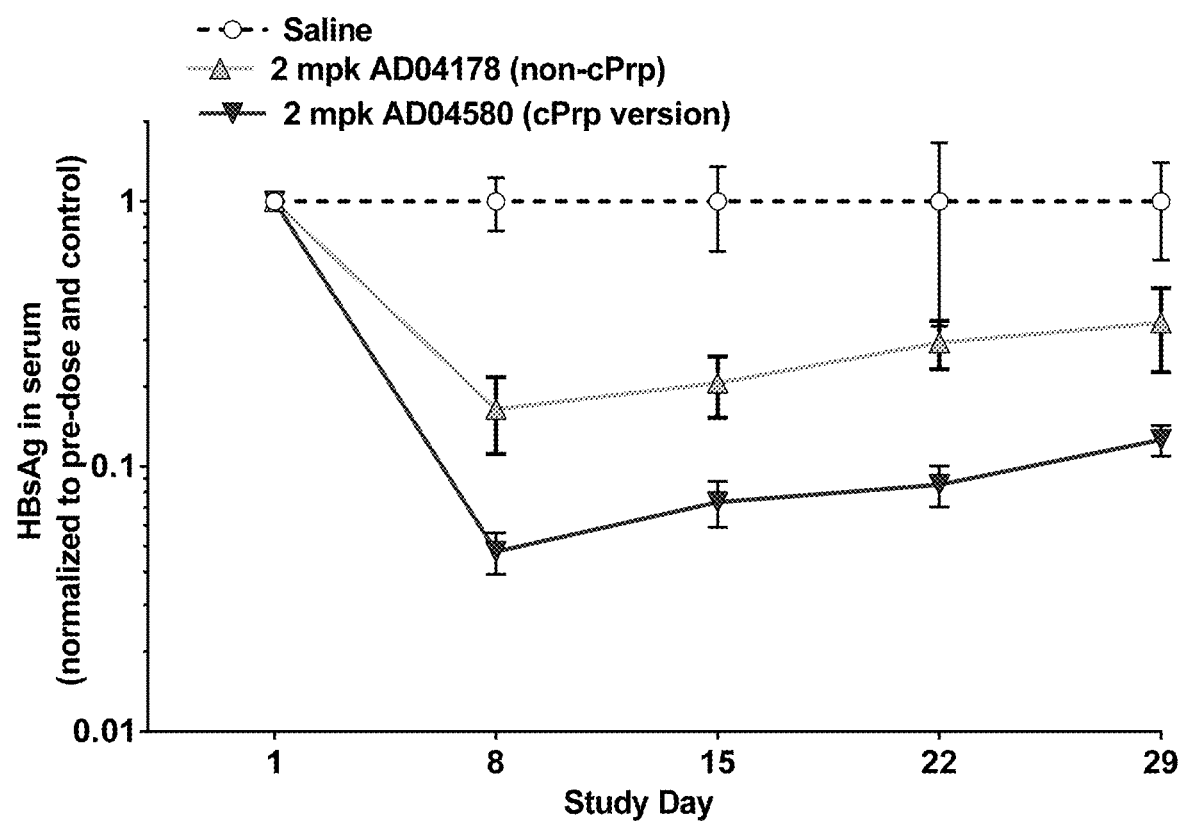
FIG. 2. Graph showing average HBsAg normalized to pre-treatment and saline control in pHBV model mice after administration of RNAi agents having sequences directed to HBV. Only AD04580 included a 5'-cylcopropyl phosphonate modified nucleotide, which was positioned at the 5' terminus of the antisense strand.

Data from the experiment is shown in FIG. 2, with Average HBsAg reflecting the normalized average value of HBsAg. As shown in FIG. 2, the RNAi agent that included a 5'-cylcopropyl phosphonate modified nucleotide (AD04580) significantly outperformed the RNAi agent without the modification (AD04178) in the pHBV model mice.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A compound having Formula A:

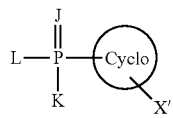

(Formula A)

wherein:

Cyclo is

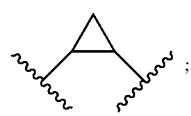 [SMILES: *C1CC1*]

X' is

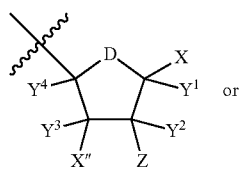

(s-i)

or

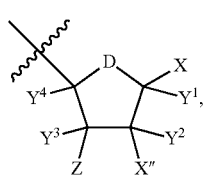

(s-ii)

X" comprises a substituent derived from a phosphate or phosphorothioate moiety of an RNAi agent;

D is O or S;

X is a 9-purinyl or 1-pyrimidinyl base;

Z is H, —OH, F, OCH$_3$, —O—(CH$_2$)$_2$—OCH$_3$ or halogen;

$Y^1$, $Y^2$, $Y^3$, and $Y^4$ are each, independently, H, halogen, C$_1$-C$_6$ alkyl, C$_1$-C$_6$ alkoxy, C$_2$-C$_6$ alkenyl, or C$_2$-C$_6$ alkynyl, J is O or S; and K and L are each independently selected from OH, OR$^{16}$, SR$^{16}$, or NR$^{16}$, wherein R$^{16}$ is selected from H, C$_1$-C$_{10}$ alkyl, C$_2$-C$_6$ alkenyl, C$_2$-C$_6$ alkynyl, aryl, or

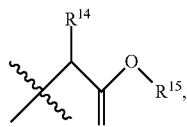

wherein R$^{14}$ is selected from H or C$_1$-C$_4$ alkyl optionally substituted with one to three substituents independently selected from SH, S—(C1-C4 alkyl), amino, hydroxyl, oxo or —NH—C=(NH)NH$_2$, and R$^{15}$ is selected from H, or C$_1$-C$_{18}$ alkyl.

2. The compound of claim 1, having Formula I or Formula II:

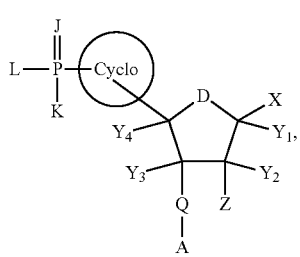

(Formula I)

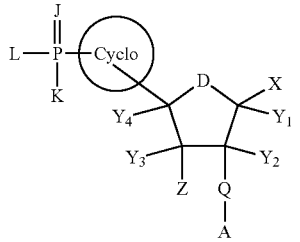

(Formula II)

wherein,

Q is a divalent moiety selected from O, S, N(R$^{30}$), or C(R$^{31}$)(R$^{32}$), wherein R$^{30}$ is H, C$_1$-C$_6$ alkyl, C$_1$-C$_6$ alkoxy, C$_2$-C$_6$ alkenyl, or C$_2$-C$_6$ alkynyl, and R$^{31}$ and R$^{32}$ are each, independently, H, halogen, C$_1$-C$_6$ alkyl, C$_1$-C$_6$ alkoxy, C$_2$-C$_6$ alkenyl, or C$_2$-C$_6$ alkynyl; and A a substituent derived from a phosphate or phosphorothioate moiety of an RNAi agent.

3. The compound of claim 2 wherein Q is O.

4. The compound of claim 1, wherein Cyclo is:

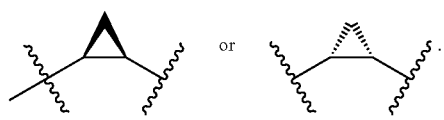 [SMILES: *[C@@H]1C[C@@H]1* ; *[C@@H]1C[C@@H]1*]

5. The compound of claim 1, wherein the RNAi agent is double-stranded.

6. The compound of claim 1, wherein X is 1-uracilyl, 1-thyminyl, 1-cytosinyl, 5-methyl-1-cytosinyl, 9-adeninyl, 9-guaninyl, or 9-inosinyl.

7. A composition comprising the compound of claim 1.

8. A composition comprising an RNAi agent, wherein the RNAi agent comprises the compound of claim 1.

9. The composition of claim 8, wherein the RNAi agent is double stranded.

10. A compound having the structure of Formula I-b or Formula II-b:

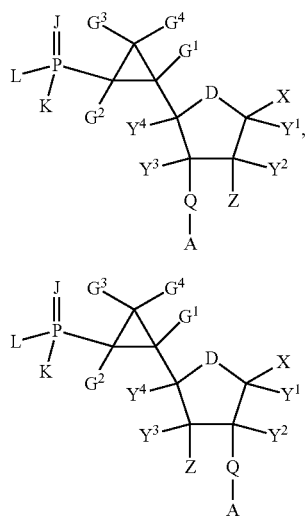

(Formula I-b)

(Formula II-b)

wherein,

D is O or S;

X is a 9-purinyl or 1-pyrimidinyl base;

Z is H, —OH, F, $OCH_3$, —O—$(CH_2)_2$—$OCH_3$ or halogen;

$Y^1$, $Y^2$, $Y^3$, and $Y^4$ are each, independently, H, halogen, $C_1$-$C_6$ alkyl, $C_1$-$C_6$ alkoxy, $C_2$-$C_6$ alkenyl, or $C_2$-$C_6$ alkynyl, J is O or S;

K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

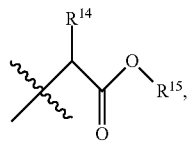

wherein $R^{14}$ is selected from H or $C_1$-$C_4$ alkyl optionally substituted with one to three substituents independently selected from SH, S—(C1-C4 alkyl), amino, hydroxyl, oxo or —NH—C=$(NH)NH_2$, and $R^{15}$ is selected from H, or $C_1$-$C_{18}$ alkyl;

Q is a divalent moiety selected from O, S, $N(R^{30})$, or $C(R^{31})(R^{32})$, wherein $R^{30}$ is H, $C_1$-$C_6$ alkyl, $C_1$-$C_6$ alkoxy, $C_2$-$C_6$ alkenyl, or $C_2$-$C_6$ alkynyl, and $R^{31}$ and $R^{32}$ are each, independently, H, halogen, $C_1$-$C_6$ alkyl, $C_1$-$C_6$ alkoxy, $C_2$-$C_6$ alkenyl, or $C_2$-$C_6$ alkynyl; and A comprises a substituent derived from a phosphate or phosphorothioate moiety of an RNAi agent; and $G^1$, $G^2$, $G^3$ and $G^4$ are each H.

11. The compound of claim 10, wherein Q is O.

12. A compound having Formula I-b-5 or Formula II-b-5:

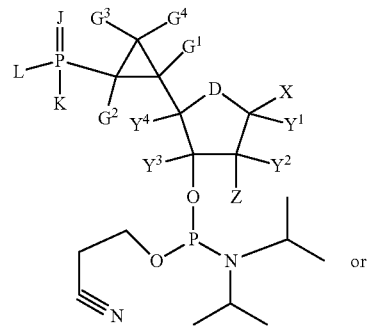

(Formula I-b-5)

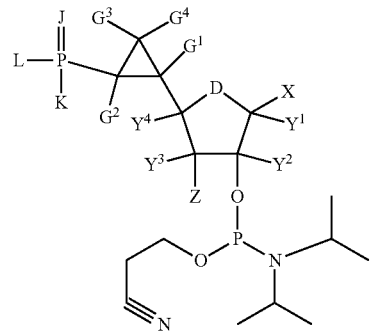

(Formula II-b-5)

wherein,

D is O or S,

X is a 9-purinyl or 1-pyrimidinyl base;

Z is H, —OH, F, $OCH_3$, —O—$(CH_2)_2$—$OCH_3$ or halogen;

$Y^1$, $Y^2$, $Y^3$, and $Y^4$ are each, independently, H, halogen, $C_1$-$C_6$ alkyl, $C_1$-$C_6$ alkyl, $C_1$-$C_6$ alkoxy, $C_1$-$C_6$ alkoxy, $C_2$-$C_6$ alkenyl, $C_2$-$C_6$ alkenyl, $C_2$-$C_6$ alkynyl, or $C_2$-$C_6$ alkynyl;

J is O or S;

K and L are each independently selected from OH, $OR^{16}$, $SR^{16}$, or $NR^{16}$, wherein $R^{16}$ is selected from H, $C_1$-$C_{10}$ alkyl, $C_2$-$C_6$ alkenyl, $C_2$-$C_6$ alkynyl, aryl, or

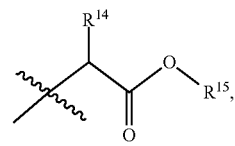

wherein $R^{14}$ is selected from H or $C_1$-$C_4$ alkyl optionally substituted with one to three substituents independently selected from SH, S—(C1-C4 alkyl), amino, hydroxyl, oxo or —NH—C=$(NH)NH_2$, and $R^{15}$ is selected from H, or $C_1$-$C_{18}$ alkyl; and $G^1$, $G^2$, $G^3$ and $G^4$ are each independently selected from the group consisting of H, F, halogen, $C_1$-$C_6$ alkyl, CN, $CH_2(R^{33})$, $CH_2$—O—$(R^{33})$, C(=O)$(R^{33})$, C(=S)$(R^{33})$, or $(R^{34})(R^{33})$, wherein $R^{33}$ is O$(R^{35})$, S$(R^{35})$, or $N(R^{35})(R^{36})$, wherein $R^{34}$, $R^{35}$, and $R^{36}$ are each independently selected from H, halogen, or $C_1$-$C_6$ alkyl.

13. The compound of claim 12, wherein the compound has the following structure:

(Structure xi)

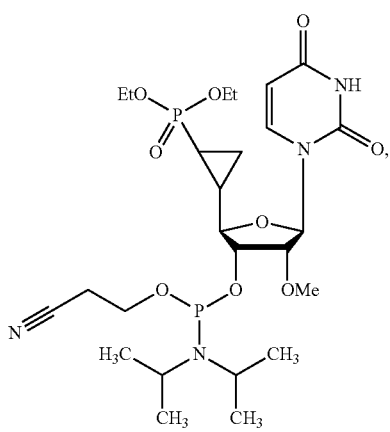

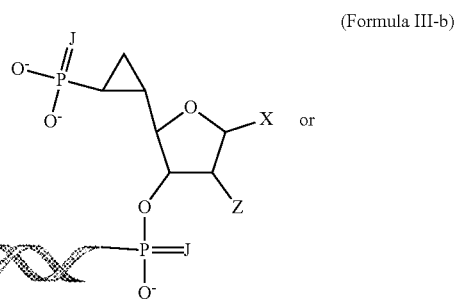

14. A compound having Formula III-b or Formula IV-b:

(Formula III-b)

(Formula IV-b)

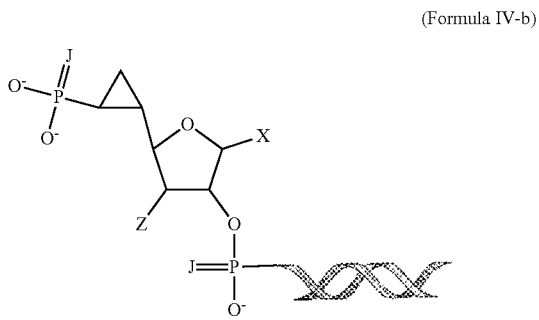

(Structure xii)

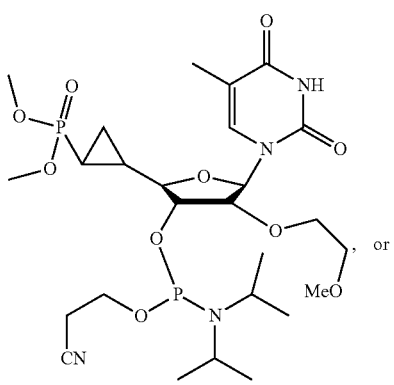

wherein:

X is a 9-purinyl or 1-pyrimidinyl base;

Z is H, —OH, F, OCH$_3$, —O—(CH$_2$)$_2$—OCH$_3$ or halogen;

J and J' are each independently O or S; and

〰 comprises a substituent derived from an RNAi agent.

15. The compound of claim 1, wherein the compound has the formula selected from the group consisting of:

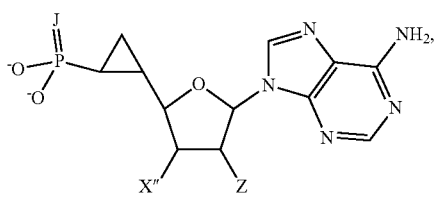

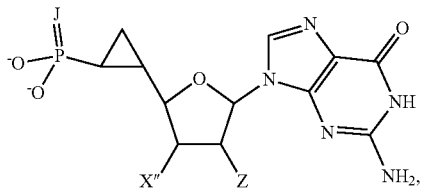

(Structure xiii)

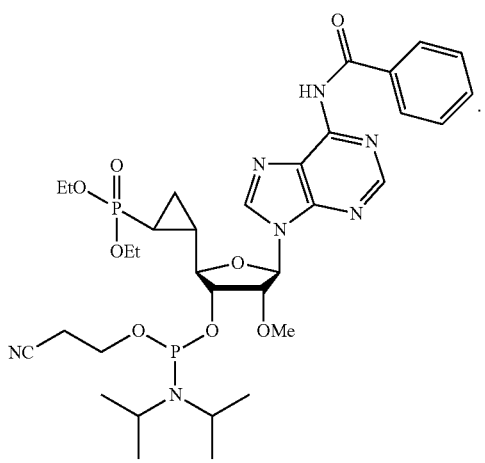

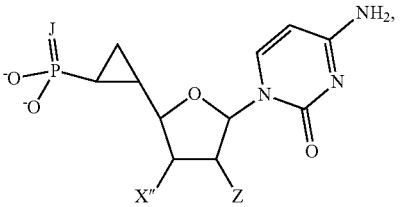

-continued

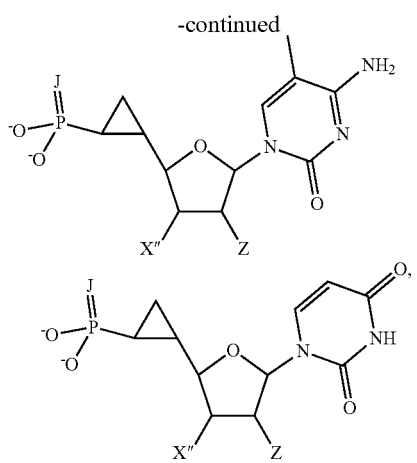

or a pharmaceutically acceptable salt thereof.

16. A composition comprising the RNAi agent of claim 1 and a pharmaceutically acceptable excipient.

17. A method of inhibiting expression of a target nucleic acid in a subject in need thereof, the method comprising administering to the subject a therapeutic amount of an RNAi agent of claim 1.

18. A method of treating a disease or disorder in a subject in need thereof, the method comprising administering a therapeutic amount of the composition of claim 8 to a subject in need of treatment thereof.

19. A method of inhibiting expression of a target nucleic acid in a subject in need thereof, the method comprising administering to the subject a therapeutic amount of a composition of claim 8.

* * * * *